US012269801B2

(12) United States Patent
Stafford et al.

(10) Patent No.: US 12,269,801 B2
(45) Date of Patent: Apr. 8, 2025

(54) MODIFIED AMINO ACIDS

(71) Applicant: SUTRO BIOPHARMA, INC., South San Francisco, CA (US)

(72) Inventors: Ryan Stafford, Foster City, CA (US); Christopher D. Thanos, Tiburon, CA (US); Wenjin Yang, Foster City, CA (US)

(73) Assignee: SUTRO BIOPHARMA, INC., South San Francisco, CA (US)

( * ) Notice: Subject to any disclaimer, the term of this patent is extended or adjusted under 35 U.S.C. 154(b) by 166 days.

(21) Appl. No.: 18/067,709

(22) Filed: Dec. 17, 2022

(65) Prior Publication Data
US 2023/0139442 A1 May 4, 2023

Related U.S. Application Data

(60) Continuation of application No. 16/984,152, filed on Aug. 4, 2020, now Pat. No. 11,548,852, which is a continuation of application No. 16/173,968, filed on Oct. 29, 2018, now Pat. No. 10,730,837, which is a continuation of application No. 15/600,632, filed on May 19, 2017, now Pat. No. 10,112,900, which is a division of application No. 14/015,893, filed on Aug. 30, 2013, now Pat. No. 9,682,934.

(60) Provisional application No. 61/696,087, filed on Aug. 31, 2012.

(51) Int. Cl.
| C07D 213/55 | (2006.01) |
| C07C 247/04 | (2006.01) |
| C07C 271/20 | (2006.01) |
| C07C 275/14 | (2006.01) |
| C07K 14/00 | (2006.01) |
| C07K 16/00 | (2006.01) |

(52) U.S. Cl.
CPC .......... *C07D 213/55* (2013.01); *C07C 247/04* (2013.01); *C07C 271/20* (2013.01); *C07C 275/14* (2013.01); *C07K 14/00* (2013.01); *C07K 16/00* (2013.01)

(58) Field of Classification Search
None
See application file for complete search history.

(56) References Cited

U.S. PATENT DOCUMENTS

| 4,542,225 A | 9/1985 | Blattler et al. |
| 4,618,492 A | 10/1986 | Blattler et al. |
| 4,625,014 A | 11/1986 | Senter et al. |
| 4,671,958 A | 6/1987 | Rodwell et al. |
| 5,643,575 A | 7/1997 | Martinez et al. |
| 5,932,462 A | 8/1999 | Harris et al. |
| 7,026,440 B2 | 4/2006 | Bentley et al. |
| 7,045,337 B2 | 5/2006 | Schultz et al. |
| 7,083,970 B2 | 8/2006 | Schultz et al. |
| 7,332,571 B2 | 2/2008 | Miao et al. |
| 7,338,789 B2 | 3/2008 | Swartz et al. |
| 7,696,312 B2 | 4/2010 | Miao et al. |
| 7,736,653 B2 | 6/2010 | Kim et al. |
| 7,887,809 B1 | 2/2011 | Garen et al. |
| 7,993,872 B2 | 8/2011 | Deiters et al. |
| 8,008,443 B2 | 8/2011 | Dall'Acqua et al. |
| 8,008,453 B2 | 8/2011 | Gegg et al. |
| 8,030,074 B2 | 10/2011 | Schultz et al. |
| 8,124,094 B2 | 2/2012 | Kim et al. |
| 8,216,804 B2 | 7/2012 | Schultz et al. |
| 8,263,740 B2 | 9/2012 | Miao et al. |
| 8,476,411 B2 | 7/2013 | Miao et al. |
| 8,618,257 B2 | 12/2013 | Sheffer et al. |
| 8,715,958 B2 | 5/2014 | Goerke et al. |
| 9,682,934 B2 | 6/2017 | Stafford et al. |
| 10,112,900 B2 | 10/2018 | Stafford et al. |
| 10,730,837 B2 | 8/2020 | Stafford et al. |
| 2003/0082575 A1 | 5/2003 | Schultz et al. |
| 2003/0108885 A1 | 7/2003 | Schultz et al. |
| 2003/0143596 A1 | 7/2003 | Bentley et al. |
| 2007/0148170 A1 | 6/2007 | Desjarlais et al. |
| 2008/0085277 A1 | 4/2008 | Cho et al. |
| 2008/0233611 A1 | 9/2008 | Schultz et al. |
| 2008/0317670 A1 | 12/2008 | Miao et al. |
| 2009/0035836 A1 | 2/2009 | Datta et al. |
| 2009/0093405 A1 | 4/2009 | Wallen, III et al. |
| 2009/0110662 A1 | 4/2009 | Breitenkamp et al. |
| 2009/0117100 A1 | 5/2009 | Mao et al. |
| 2010/0093082 A1 | 4/2010 | Tian et al. |
| 2010/0098630 A1 | 4/2010 | Miao |

(Continued)

FOREIGN PATENT DOCUMENTS

| WO | WO 2002/085923 A3 | 10/2002 |
| WO | WO 2004/016778 A1 | 2/2004 |

(Continued)

OTHER PUBLICATIONS

Axup et al., Synthesis of site-specific antibody-drug conjugates using unnatural amino acids (2012) *Proc. Nat. Acad. Sci. USA* 109(40):16101-16106.

(Continued)

*Primary Examiner* — Zinna Northington Davis

(74) *Attorney, Agent, or Firm* — Squire Patton Boggs (US) LLP

(57) ABSTRACT

Provided herein are modified amino acids comprising an azido group, polypeptides, antibodies and conjugates comprising the modified amino acids, and methods of producing the polypeptides, antibodies and conjugates comprising the modified amino acids. The polypeptides, antibodies and conjugates are useful in methods of treatment and prevention, methods of detection and methods of diagnosis.

17 Claims, 4 Drawing Sheets

Specification includes a Sequence Listing.

(56) References Cited

U.S. PATENT DOCUMENTS

| | | |
|---|---|---|
| 2012/0077948 A1 | 3/2012 | Nguyen et al. |
| 2012/0100140 A1 | 4/2012 | Reyes et al. |
| 2014/0046030 A1 | 2/2014 | Thanos et al. |
| 2014/0127209 A1 | 5/2014 | Grabstein et al. |

FOREIGN PATENT DOCUMENTS

| | | |
|---|---|---|
| WO | WO 2005/047337 A1 | 5/2005 |
| WO | WO 2006/069246 A2 | 6/2006 |
| WO | WO 2006/116260 A2 | 11/2006 |
| WO | WO 2007/041635 A2 | 4/2007 |
| WO | WO 2008/030558 A2 | 3/2008 |
| WO | WO 2008/066583 A2 | 6/2008 |
| WO | WO 2008/134761 A2 | 11/2008 |
| WO | WO 2009/052249 A1 | 4/2009 |
| WO | WO 2009/148554 A1 | 12/2009 |
| WO | WO 2010/051056 A2 | 5/2010 |
| WO | WO 2010/139948 A2 | 12/2010 |
| WO | WO 2011/044255 A1 | 4/2011 |
| WO | WO 2012/032181 A2 | 3/2012 |
| WO | WO 2013/068874 A1 | 5/2013 |

OTHER PUBLICATIONS

Balog et al., Synthesis of new 2,2,5,5-Tetramethyl-2,5-dihydro-1H-pyrrol-1-yloxyl Radicals and 2-Substituted-2,5,5-trimethylpyrrolidin-1-yloxyl Radicals Based α-Amino Acids (2004) *SYNLETT* 14:2591-2593.

Bazewicz et al. "Sensitive, Site-Specific, and Stable Vibrational Probe of Local Protein Environments: 4-Azidomethyl-L-Phenylalanine," *J. Phys. Chem. B*, 2013, 117 (30), pp. 8987-8993.

Brewer et al., Expanding the Utility of 4-Cyano-L-Phenylalanine As a Vibrational Reporter of Protein Environments, *The Journal of Physical Chemistry B*. 2012 (published on web on Aug. 22, 2012), vol. 35, p. 10825.

Bundy et al., "Site-Specific Incorporation of p-Propargyloxyphenylalanine in a Cell-Free Environment for Direct Pro-tein-Protein Click Conjugation", Bioconjugate Chem. 2010, vol. 21, pp. 255-263.

Carlson et al., "Cell-Free Protein Synthesis: Applications Come of Age", *Biotechnol Adv.*, 2012, vol. 30, No. 5, pp. 1185-1194.

Carter, Introduction to current and future protein therapeutics: A protein engineering perspective *Experimental Cell Research* (2011) 317(9):1261-1269.

Chen et al., N-Benzylpyroglutamyl-L-phenylalanine Derivatives as VCAM/VLA-4 Antagonists (2000) *Bioorg. & Med. Chem. Let.* 10:729-733.

Chin et al., Addition of p-azido-L-phenylalanine to the genetic code of *Escherichia coli* (2002) *J. Am. Chem. Soc.* 124:9026-9027.

Chin et al., An Expanded Eukaryotic Genetic Code (2003) *Science* 301:964-967.

Chu, KC. et al., "Pattern recognition and structure-activity relation studies. Computer-assisted prediction of antitumor activity in structurally diverse drugs in an experimental mouse brain tumor system", Journal of Medicinal Chemistry, 1975, vol. 18, p. 543.

Dewald et al., "Some New Esters of Serine with Various Acids", Journal of the American Chemical Society, Aug. 20, 1959, vol. 81, pp. 4367-4370.

Delgado et al., The uses and properties of PEG-linked proteins (1992) *Critical Reviews in Therapeutic Drug Carrier Systems* 9:249-304.

Gerber et al., The antibody-drug conjugate: an enabling modality for natural product-based cancer therapeutics (2013) Nat. Prod. Rep. 30:625-639.

Harris, Laboratory synthesis of polyethylene glycol derivatives (1985) *Macronol. Chem. Phys.* C25:325-373.

Howard et al., "Inhibitory Effects of Histidine Analogues on Growth and Protein Synthesis by Plasmodium Falciparum in VITRO", Biochemical Pharmacology, 1986, vol. 35, No. 9, pp. 1589-1596.

Hutchins et al., Site-Specific Coupling and Sterically Controlled Formation of Multimeric Antibody Fab Fragments with Unnatural Amino Acids (2011) *J. Mol. Biol.* 406:595-603.

International Search Report and Written Opinion, mailed Dec. 20, 2013, in PCT/US2013/057677, 13 pages.

International Search Report and Written Opinion, mailed Oct. 24, 2013, in PCT/US2013/047838, 17 pages.

Jeong et al., Site-Specific $^{99m}$Tc-Labeling of Antibody Using Dihydrazinophthalazine (DHZ) Conjugation to Fc Region of Heavy Chain (2004) *Arch Pharm Res* 27:961-967.

Johansson et al., Azide- and Alkyne-Derivatised α-Amino Acids (2012) *Eur. J. Org. Chem.* 23:4267-4281.

Kaneko et al., Optimizing Therapeutic Antibody Function (2011) *Biodrugs* 25:1-11.

Katayama, H. et al., Pyrrolysine Analogs as Substrates for Bacterial Pyrrolysyl-tRNA Synthetase in Vitro and in Vivo. Bioscience, Biotechnology, and Biochemistry, 2012, vol. 76, p. 206.

Kazane et al., Self-Assembled Antibody Multimers through Peptide Nucleic Acid Conjugation (2013), *J. Am. Chem. Soc.* 135:340-346.

Kazane et al., Site-specific DNA-antibody conjugates for specific and sensitive immuno-PCR (2012), *PNAS* 109:3731-3736.

Kiick et al., Incorporation of azides into recombinant proteins for chemoselective modification by the Staudinger ligation (2002) *Proc. Nat. Acad. Sci. USA* 99:19-24.

Merrifield, "Solid Phase Peptide Synthesis. I. The Synthesis of a Tetrapeptide", Jul. 20, 1963, *J. Am. Chem. Soc*, vol. 85, pp. 2149-2154.

Mesas, JM. et al., "Characterization and partial purification of L-asparaginase from Corynebacterium glutamicum", Journal of General Microbiology, 1990, vol. 136, p. 515.

Nguyen et al., Genetic Encoding and Labeling of Aliphatic Azides and Alkynes in Recombinant Proteins via a Pyrrolysyl-tRNA Synthetase/ tRNA$_{CUA}$ Pair and Click Chemistry (2009) *J. Am. Chem. Soc.* 131:8720-8721.

Patel et al., "Cell-free production of Gaussia princeps luciferase—antibody fragment bioconjugates for ex vivo detection of tumor cells", Biochem Biophys Res Commun. Dec. 18, 2009, 390(3): 971-976; doi:10.1016/j.bbrc.2009.10.087.

Reichert, Antibody-based therapeutics to watch in 2011 (2011) *mABS* 3(1):76-99.

Santi et al., "Predictable and tunable half-life extension of therapeutic agents by controlled chemical release from macromolecular conjugates", (2012) *PNAS* 109(16):6211-6216.

Saxon et al., Cell surface engineering by a modified Staudinger reaction (2000) *Science* 287:2007-2010.

Scouten, A survey of enzyme coupling techniquesMethods in Enzymology (1987), *Methods in Enzymology*, vol. 135, pp. 30-65.

Strohl W., Optimization of Fc-mediated effector functions of monoclonal antibodies (2009) *Current Opinion in Biotechnology* 20:685-691.

Strop et al., Location Matters: Cite of Conjugation Modulates Stability and Pharmacokinetics of Antibody Drug Conjugates (2013) *Chem. & Biol.* 20:161-167.

Wang et al., Bioconjugation by copper(I)-catalyzed azide-alkyne [3+2] cycloaddition.(2003) *J. Am. Chem. Soc.* 125:3192-3193.

Wong et al., Chemical crosslinking and the stabilization of proteins and enzymes (1992) *Enzyme Microb. Technol.* 14:866-874.

Yin et al., Aglycosylated antibodies and antibody fragments produced in a scalable in vitro transcription-translation system (2012) *mAbs* 4:217-225.

Young et al., An Evolved Aminoacyl-tRNA Synthetase with Atypical Polysubstrate Specificity, (2011) *Biochem.* 50:1894-1900.

Zalevsky et al., Enhanced antibody half-life improves in vivo activity (2010) Nature Biotechnology 28:157-159.

Zalipsky, Functionalized poly(ethylene glycol) for preparation of biologically relevant conjugates, (1995) *Bioconjug. Chem.* 6:150-165.

Zawada et al., Microscale to Manufacturing Scale-up of Cell-Free Cytokine Production—A New Approach for Shortening Protein Production Development Timelines (2011) *Biotechnol. Bioeng.* 108(7):1570-1578.

SEQUENCE LISTING

```
Sequence total quantity: 2
SEQ ID NO: 1            moltype = AA  length = 449
FEATURE                 Location/Qualifiers
REGION                  1..449
                        note = Synthetic polypeptide
source                  1..449
                        mol_type = protein
                        organism = synthetic construct
SEQUENCE: 1
EVQLVESGGG LVQPGGSLRL SCAASGFNIK DTYIHWVRQA PGKGLEWVAR IYPTNGYTRY   60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                   449

SEQ ID NO: 2            moltype = AA  length = 214
FEATURE                 Location/Qualifiers
REGION                  1..214
                        note = Synthetic polypeptide
source                  1..214
                        mol_type = protein
                        organism = synthetic construct
SEQUENCE: 2
DIQMTQSPSS LSASVGDRVT ITCRASQDVN TAVAWYQQKP GKAPKLLIYS ASFLYSGVPS   60
RFSGSRSGTD FTLTISSLQP EDFATYYCQQ HYTTPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214
```

MODIFIED AMINO ACIDS

CROSS-REFERENCE TO RELATED APPLICATION

This application is a continuation of U.S. Ser. No. 16/984,152, filed Aug. 4, 2020, which is a continuation of U.S. Ser. No. 16/173,968, filed Oct. 29, 2018, which is a continuation of U.S. Ser. No. 15/600,632, filed May 19, 2017, now U.S. Pat. No. 10,112,900, which is a divisional application of U.S. application Ser. No. 14/015,893, filed Aug. 30, 2013, now U.S. Pat. No. 9,682,934 which claims the benefit of, and priority to, U.S. provisional patent application Ser. No. 61/696,087 entitled "MODIFIED AMINO ACIDS" filed Aug. 31, 2012. The contents of the foregoing applications are incorporated by reference herein in their entireties.

REFERENCE TO ELECTRONIC SEQUENCE LISTING

This application contains a sequence listing which has been submitted electronically in .XML format and is hereby incorporated by reference in its entirety. Said .XML copy, created on Dec. 23, 2022, is named "108843_00437_ST26.xml" and is 3,954 bytes in size which is a copy of the sequence listing as filed in U.S. application Ser. No. 16/984,152. The sequence listing contained in this XML file is part of the specification and is hereby incorporated by reference herein in its entirety.

FIELD

Provided herein are modified amino acids comprising an azido group, polypeptides, antibodies and conjugates comprising the modified amino acids, and methods of producing the polypeptides, antibodies and conjugates comprising the modified amino acids. The polypeptides, antibodies and conjugates are useful in methods of treatment and prevention, methods of detection and methods of diagnosis.

BACKGROUND

Engineered polypeptides are used widely in therapy and diagnostic applications. Therapeutic antibodies have been useful for many years in, for example, treatment of cancer and inflammatory conditions. Therapeutic polypeptides are also used to treat and prevent blood conditions and viral infections. Diagnostic polypeptides have been used successfully to identify healthy and diseased cells and tissues in vivo.

Many polypeptides can provide targeting functionality to specific cells. The selective affinity of certain polypeptides can be used to target nearly any cell or tissue desired, for example a cell expressing an antigen. A polypeptide can carry a molecular payload to slow or destroy the target cell or tissue. Polypeptides have thus found use in therapy for conditions such as cancer, inflammatory diseases, autoimmune diseases and transplant rejection.

In certain applications therapeutic polypeptides are linked to molecular shields to increase their lifetime within an organism. Polypeptides have also found use as diagnostics. These polypeptides can carry a label to indicate the presence of a target receptor on a cell or in a tissue. These labels are typically linked to the polypeptides by covalent bonds.

To date, techniques for linking polypeptides to molecular entities such as molecular payloads, including molecular shields and labels, have been limited by their heterogeneity in degree and location of linking to the polypeptides, by their low yields and by losses in activity. Typical conjugation sites include random locations on polypeptide chains, e.g. random amines on amino acid side chains, and the N-terminus of certain polypeptide chains. In such techniques, some polypeptides might be linked to the conjugate at one location while some polypeptides are linked to the same conjugate at another location, and some polypeptides might not be linked at all.

There is a need, therefore, for polypeptides modified at site-specific positions optimized for uniformity, yield and/or activity to further the promising use of polypeptides in, for example, therapy and diagnostics.

SUMMARY

Provided herein are modified amino acids comprising an azido group, polypeptides, antibodies and conjugates comprising the modified amino acids, and methods of producing the polypeptides, antibodies and conjugates comprising the modified amino acids. The polypeptides, antibodies and conjugates are useful in methods of treatment and prevention, methods of detection and methods of diagnosis.

In one aspect a compound according to formula I is provided:

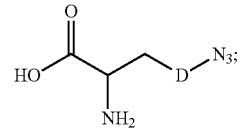

Formula I or a salt thereof, wherein: D is —Ar—$W_3$— or —$W_1$—$Y_1$—C(O)—$Y_2$—$W_2$—; Ar is

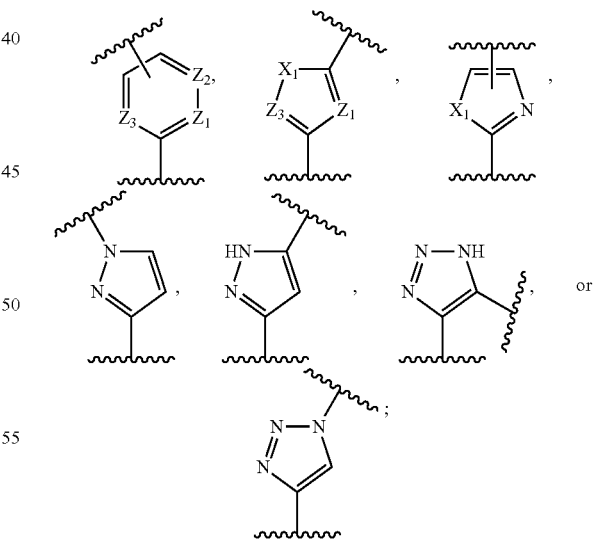

each of $W_1$, $W_2$, and $W_3$ is independently a single bond or lower alkylene; each $X_1$ is independently —NH—, —O—, or —S—; each $Y_1$ is independently a single bond, —NH—, or —O—; each $Y_2$ is independently a single bond, —NH—, —O—, or an N-linked or C-linked pyrrolidinylene; and one of $Z_1$, $Z_2$, and $Z_3$ is —N— and the others of $Z_1$, $Z_2$, and $Z_3$ are independently —CH—.

In a further aspect, polypeptides and antibodies comprising an amino acid residue corresponding to a compound of formula I are provided. In particular embodiments, conjugates of the polypeptides and payloads are provided. In further embodiments, conjugates of the antibodies and payloads are provided.

In another aspect, an orthogonal tRNA is provided aminoacylated with an amino acid residue corresponding to a compound of formula I. In a related aspect, a method of producing a polypeptide is provided, comprising contacting a polypeptide with an orthogonal tRNA aminoacylated with an amino acid residue corresponding to a compound of formula I.

The compounds of formula I described herein can be incorporated into any polypeptide known to those of skill in the art. Such polypeptides include, but are not limited to, proteins, antibodies, antibody fragments, enzymes, and nucleic acids.

BRIEF DESCRIPTION OF THE FIGURES

In FIG. 2, $k_{obs}$ is plotted on the vertical axis in units of $sec^{-1}$ from 0 to 0.006 and [Azide] is plotted on the horizontal axis in units of mM from 0 to 3. In FIG. 2, results for compound (30) are provided as open circles, results for compound (40) are provided as filled triangles, and results for compound (50) are provided as filled circles. As provided in FIG. 2, compounds (30) and (40) exhibited a first order rate constant of 1.4 $M^{-1}$ $sec^{-1}$, approximately 7-fold higher than first order rate constant of 0.2 $M^{-1}$ $sec^{-1}$ for compound (50).

In FIG. 3, RFU is plotted on the vertical axis from 0 to 400000 and time is plotted on the horizontal axis in units of minutes from 0 to 600. In FIG. 3, results for turboGFP are provided as filled squares (top), results for pCNFRS D286R pAMF are provided as filled diamonds (middle), and results for Y50TAG are provided as filled triangles (bottom). As provided in FIG. 3, turboGFP is approximately 250,000 RFU at 200 minutes, pCNFRS D286R pAMF is approximately 130,000 RFU at 200 minutes, and Y50TAG is approximately 0 RFU at 200 minutes. As provided in FIG. 3, turboGFP is approximately 340,000 RFU at 400 minutes, pCNFRS D286R pAMF is approximately 160,000 RFU at 400 minutes, and Y50TAG is approximately 0 RFU at 400 minutes. As provided in FIG. 3, turboGFP is approximately 370,000 RFU at 600 minutes, pCNFRS D286R pAMF is approximately 170,000 RFU at 600 minutes, and Y50TAG is approximately 0 RFU at 600 minutes.

In FIG. 4, the fraction of $DBCO-NH_2$ (61) remaining is plotted on the vertical axis in a unitless value from 0 to 1.2 and time is plotted on the horizontal axis in units of 0 hours to 20 hours. In FIG. 4, the results for compound (30) are provided as filled diamonds, the results for compound (1) are provided as filled squares, and the results for compound (2) are provided as filled triangles. As provided in FIG. 4, compounds (1) and (30) reacted with compound (61) at comparable rates, while the reaction rate between compound (2) and compound (61) was two- to four-fold slower than the reaction rate between compounds (1) and (61) and compounds (30) and (61).

DESCRIPTION OF EXEMPLARY EMBODIMENTS

Figure 1:
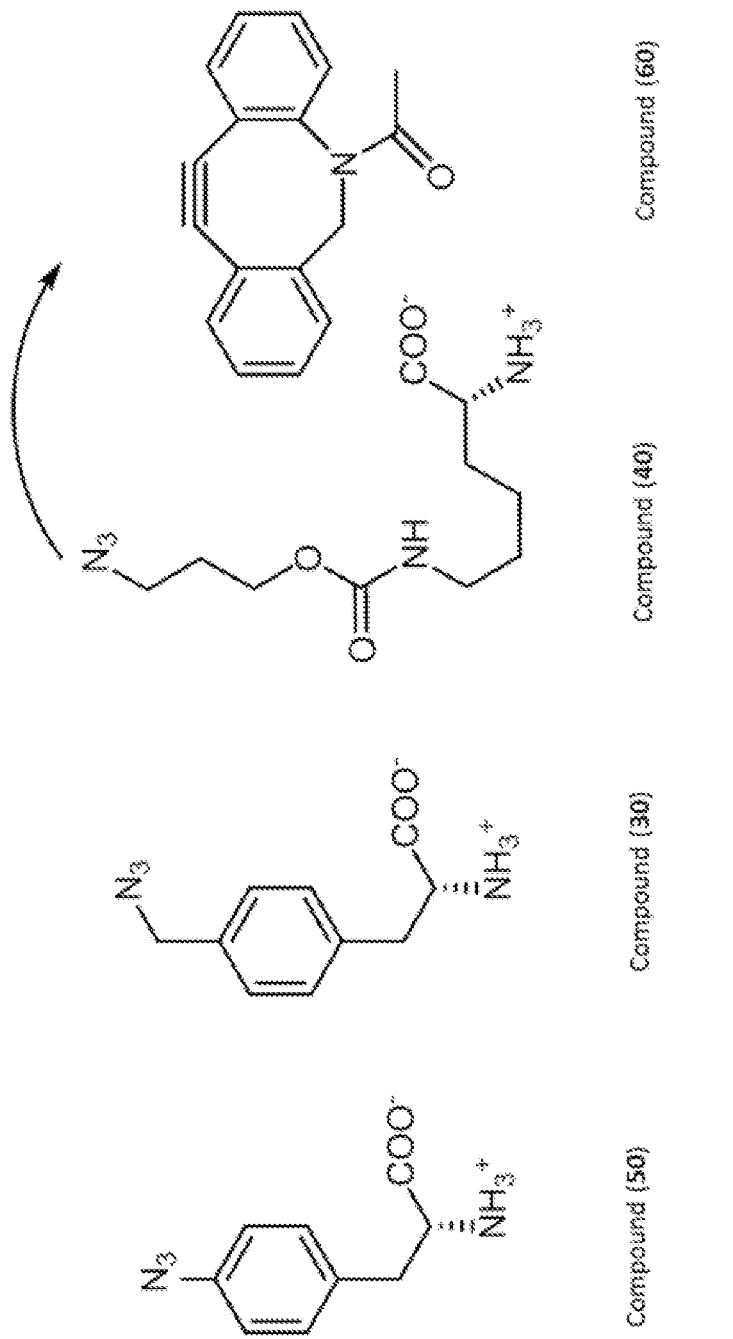
FIG. 1 provides A schematic of the reaction of compounds (30), (40), and (50) with compound (60).

Provided herein are compounds of formula I, polypeptides, antibodies and conjugates comprising the amino acid residues corresponding to the compounds of formula I, and methods of producing the polypeptides, antibodies and conjugates comprising the modified amino acid residues corresponding to the compounds of formula I.

Definitions

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

The term "alkyl," as used herein, unless otherwise specified, refers to a saturated straight or branched hydrocarbon. In certain embodiments, the alkyl group is a primary, secondary, or tertiary hydrocarbon. In certain embodiments, the alkyl group includes one to ten carbon atoms, i.e., $C_1$ to $C_{10}$ alkyl. In certain embodiments, the alkyl group is selected from the group consisting of methyl, $CF_3$, $CCl_3$, $CFCl_2$, $CF_2Cl$, ethyl, $CH_2CF_3$, $CF_2CF_3$, propyl, isopropyl, butyl, isobutyl, secbutyl, t-butyl, pentyl, isopentyl, neopentyl, hexyl, isohexyl, 3-methylpentyl, 2,2-dimethylbutyl, and 2,3-dimethylbutyl. The term includes both substituted and unsubstituted alkyl groups, including halogenated alkyl groups. In certain embodiments, the alkyl group is a fluorinated alkyl group. Non-limiting examples of moieties with which the alkyl group can be substituted are selected from the group consisting of halogen (fluoro, chloro, bromo or iodo), hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991, hereby incorporated by reference.

The term "lower alkyl," as used herein, and unless otherwise specified, refers to a saturated straight or branched hydrocarbon having one to six carbon atoms, i.e., $C_1$ to $C_6$ alkyl. In certain embodiments, the lower alkyl group is a primary, secondary, or tertiary hydrocarbon. The term includes both substituted and unsubstituted moieties.

The term "cycloalkyl," as used herein, unless otherwise specified, refers to a saturated cyclic hydrocarbon. In certain embodiments, the cycloalkyl group may be a saturated, and/or bridged, and/or non-bridged, and/or a fused bicyclic group. In certain embodiments, the cycloalkyl group includes three to ten carbon atoms, i.e., $C_3$ to $C_{10}$ cycloalkyl. In some embodiments, the cycloalkyl has from 3 to 15 ($C_{3-15}$), from 3 to 10 ($C_{3-10}$), or from 3 to 7 ($C_{3-7}$) carbon atoms. In certain embodiments, the cycloalkyl group is cyclopropyl, cyclobutyl, cyclopentyl, cyclohexyl, cyclohexylmethyl, cycloheptyl, bicyclo[2.1.1]hexyl, bicyclo[2.2.1]heptyl, decalinyl or adamantyl. The term includes both substituted and unsubstituted cycloalkyl groups, including halogenated cycloalkyl groups. In certain embodiments, the cycloalkyl group is a fluorinated cycloalkyl group. Non-limiting examples of moieties with which the cycloalkyl group can be substituted are selected from the group consisting of halogen (fluoro, chloro, bromo or iodo), hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary.

"Alkylene" refers to divalent saturated aliphatic hydrocarbon groups particularly having from one to eleven carbon atoms which can be straight-chained or branched. In certain embodiments, the alkylene group contains 1 to 10 carbon atoms. The term includes both substituted and unsubstituted moieties. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like. The term includes halogenated alkylene groups. In certain embodiments, the alkylene group is a fluorinated alkylene group. Non-limiting examples of moieties with which the alkylene group can be substituted are selected from the group consisting of halogen (fluoro, chloro, bromo or iodo), hydroxyl, carbonyl, sulfanyl, amino, alkylamino, alkylaryl, arylamino, alkoxy, aryloxy, nitro, cyano, sulfonic acid, sulfate, phosphonic acid, phosphate, and phosphonate, either unprotected, or protected as necessary.

"Alkenyl" refers to monovalent olefinically unsaturated hydrocarbon groups, in certain embodiment, having up to about 11 carbon atoms, from 2 to 8 carbon atoms, or from 2 to 6 carbon atoms, which can be straight-chained or branched and having at least 1 or from 1 to 2 sites of olefinic unsaturation. The term includes both substituted and unsubstituted moieties. Exemplary alkenyl groups include ethenyl (i.e., vinyl, or —CH=CH$_2$), n-propenyl (—CH$_2$CH=CH$_2$), isopropenyl (—C(CH$_3$)=CH$_2$), and the like. The term includes halogenated alkenyl groups. In certain embodiments, the alkenyl group is a fluorinated alkenyl group. Non-limiting examples of moieties with which the alkenyl group can be substituted are selected from the group consisting of halogen (fluoro, chloro, bromo or iodo), hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary.

The term "cycloalkenyl," as used herein, unless otherwise specified, refers to an unsaturated cyclic hydrocarbon. In certain embodiments, cycloalkenyl refers to mono- or multicyclic ring systems that include at least one double bond. In certain embodiments, the cycloalkenyl group may be a bridged, non-bridged, and/or a fused bicyclic group. In certain embodiments, the cycloalkyl group includes three to ten carbon atoms, i.e., C$_3$ to C$_{10}$ cycloalkyl. In some embodiments, the cycloalkenyl has from 3 to 7 (C$_{3-10}$), or from 4 to 7 (C$_{3-7}$) carbon atoms. The term includes both substituted and unsubstituted cycloalkenyl groups, including halogenated cycloalkenyl groups. In certain embodiments, the cycloalkenyl group is a fluorinated cycloalkenyl group. Non-limiting examples of moieties with which the cycloalkenyl group can be substituted are selected from the group consisting of halogen (fluoro, chloro, bromo or iodo), hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary.

"Alkenylene" refers to divalent olefinically unsaturated hydrocarbon groups, in certain embodiments, having up to about 11 carbon atoms or from 2 to 6 carbon atoms which can be straight-chained or branched and having at least 1 or from 1 to 2 sites of olefinic unsaturation. This term is exemplified by groups such as ethenylene (—CH=CH—), the propenylene isomers (e.g., —CH=CHCH$_2$— and —C(CH$_3$)=CH— and —CH=C(CH$_3$)—) and the like. The term includes both substituted and unsubstituted alkenylene groups, including halogenated alkenylene groups. In certain embodiments, the alkenylene group is a fluorinated alkenylene group. Non-limiting examples of moieties with which the alkenylene group can be substituted are selected from the group consisting of halogen (fluoro, chloro, bromo or iodo), hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary.

"Alkynyl" refers to acetylenically unsaturated hydrocarbon groups, in certain embodiments, having up to about 11 carbon atoms or from 2 to 6 carbon atoms which can be straight-chained or branched and having at least 1 or from 1 to 2 sites of alkynyl unsaturation. Non-limiting examples of alkynyl groups include acetylenic, ethynyl (—C≡CH), propargyl (—CH$_2$C≡CH), and the like. The term includes both substituted and unsubstituted alkynyl groups, including halogenated alkynyl groups. In certain embodiments, the alkynyl group is a fluorinated alkynyl group. Non-limiting examples of moieties with which the alkynyl group can be substituted are selected from the group consisting of halogen (fluoro, chloro, bromo or iodo), hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary.

The term "aryl," as used herein, and unless otherwise specified, refers to phenyl, biphenyl or naphthyl. The term includes both substituted and unsubstituted moieties. An aryl group can be substituted with any described moiety, including, but not limited to, one or more moieties selected from the group consisting of halogen (fluoro, chloro, bromo or iodo), alkyl, haloalkyl, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

"Alkoxy" refers to the group —OR' where R' is alkyl or cycloalkyl. Alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkoxycarbonyl" refers to a radical —C(O)-alkoxy where alkoxy is as defined herein.

"Amino" refers to the radical —NH$_2$.

"Carboxyl" or "carboxy" refers to the radical —C(O)OH.

The term "alkylamino" or "arylamino" refers to an amino group that has one or two alkyl or aryl substituents, respectively. In certain embodiments, the alkyl substituent is lower alkyl. In another embodiment, the alkyl or lower alkyl is unsubstituted.

"Halogen" or "halo" refers to chloro, bromo, fluoro or iodo.

"Thioalkoxy" refers to the group —SR' where R' is alkyl or cycloalkyl.

The term "heterocyclyl" or "heterocyclic" refers to a monovalent monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. Heterocyclyl groups are bonded to the rest of the molecule through the non-aromatic ring. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic radicals include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, O-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted as described herein.

The term "heteroaryl" refers to refers to a monovalent monocyclic aromatic group and/or multicyclic aromatic group that contain at least one aromatic ring, wherein at least one aromatic ring contains one or more heteroatoms independently selected from O, S and N in the ring. Heteroaryl groups are bonded to the rest of the molecule through the aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl and xanthenyl. In certain embodiments, heteroaryl may also be optionally substituted as described herein.

The term "alkylaryl" refers to an aryl group with an alkyl substituent. The term "aralkyl" or "arylalkyl" refers to an alkyl group with an aryl substituent.

The term "protecting group" as used herein and unless otherwise defined refers to a group that is added to an oxygen, nitrogen or phosphorus atom to prevent its further reaction or for other purposes. A wide variety of oxygen and nitrogen protecting groups are known to those skilled in the art of organic synthesis.

"Pharmaceutically acceptable salt" refers to any salt of a compound provided herein which retains its biological properties and which is not toxic or otherwise undesirable for pharmaceutical use. Such salts may be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) base addition salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Pharmaceutically acceptable salts further include, by way of example only and without limitation, sodium, potassium, calcium, magnesium, ammonium, tetraalkylammonium and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

The term "acyl" or "O-linked ester" refers to a group of the formula C(O)R', wherein R' is alkyl or cycloalkyl (including lower alkyl), carboxylate reside of amino acid, aryl including phenyl, alkaryl, arylalkyl including benzyl, alkoxyalkyl including methoxymethyl, aryloxyalkyl such as phenoxymethyl; or substituted alkyl (including lower alkyl), aryl including phenyl optionally substituted with chloro, bromo, fluoro, iodo, $C_1$ to $C_4$ alkyl or $C_1$ to $C_4$ alkoxy, sulfonate esters such as alkyl or arylalkyl sulphonyl including methanesulfonyl, the mono, di or triphosphate ester, trityl or monomethoxy-trityl, substituted benzyl, alkaryl, arylalkyl including benzyl, alkoxyalkyl including methoxymethyl, aryloxyalkyl such as phenoxymethyl. Aryl groups in the esters optimally comprise a phenyl group. In particular, acyl groups include acetyl, trifluoroacetyl, methylacetyl, cyclpropylacetyl, propionyl, butyryl, hexanoyl, heptanoyl, octanoyl, neo-heptanoyl, phenylacetyl, 2-acetoxy-2-phenylacetyl, diphenylacetyl, α-methoxy-α-trifluoromethyl-phenylacetyl, bromoacetyl, 2-nitrobenzeneacetyl, 4-chloro-benzeneacetyl, 2-chloro-2,2-diphenylacetyl, 2-chloro-2-phenylacetyl, trimethylacetyl, chlorodifluoroacetyl, perfluoroacetyl, fluoroacetyl, bromodifluoroacetyl, methoxyacetyl, 2-thiopheneacetyl, chlorosulfonylacetyl, 3-methoxyphenylacetyl, phenoxyacetyl, tert-butylacetyl, trichloroacetyl, monochloro-acetyl, dichloroacetyl, 7H-dodecafluoro-heptanoyl, perfluoroheptanoyl, 7H-dodeca-fluoroheptanoyl, 7-chlorododecafluoro-heptanoyl, 7-chloro-dodecafluoro-heptanoyl, 7H-dodecafluoro-heptanoyl, 7H-dodeca-fluoroheptanoyl, nona-fluoro-3,6-dioxa-heptanoyl, nonafluoro-3,6-dioxaheptanoyl, perfluoroheptanoyl, methoxybenzoyl, methyl 3-amino-5-phenylthiophene-2-carboxyl, 3,6-dichloro-2-methoxybenzoyl, 4-(1,1,2,2-tetrafluoro-ethoxy)-benzoyl, 2-bromo-propionyl, omega-aminocapryl, decanoyl, n-pentadecanoyl, stearyl, 3-cyclopentyl-propionyl, 1-benzene-carboxyl, O-acetylmandelyl, pivaloyl acetyl, 1-adamantane-carboxyl, cyclohexane-carboxyl, 2,6-pyridinedicarboxyl, cyclopropane-carboxyl, cyclobutane-carboxyl, perfluorocyclohexyl carboxyl, 4-methylbenzoyl, chloromethyl isoxazolyl carbonyl, perfluorocyclohexyl carboxyl, crotonyl, 1-methyl-1H-indazole-3-carbonyl, 2-propenyl, isovaleryl, 1-pyrrolidinecarbonyl, 4-phenylbenzoyl.

The term "amino acid" refers to naturally occurring and synthetic α, β γ or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In certain embodiments, the amino acid is in the L-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a modified amino acid. Additionally, such "polypeptides," "peptides" and "proteins" include amino acid chains of any length, including full length proteins, wherein the amino acid residues are linked by covalent peptide bonds.

The term "substantially free of" or "substantially in the absence of" with respect to a nucleoside composition refers to a nucleoside composition that includes at least 85 or 90% by weight, in certain embodiments 95%, 98%, 99% or 100% by weight, of the designated enantiomer of that nucleoside. In certain embodiments, in the methods and compounds provided herein, the compounds are substantially free of enantiomers.

Similarly, the term "isolated" with respect to a nucleoside composition refers to a nucleoside composition that includes at least 85, 90%, 95%, 98%, 99% to 100% by weight, of the nucleoside, the remainder comprising other chemical species or enantiomers.

"Solvate" refers to a compound provided herein or a salt thereof, that further includes a stoichiometric or non-stoichiometric amount of solvent bound by non-covalent intermolecular forces. Where the solvent is water, the solvate is a hydrate.

"Isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen," the position is understood to have hydrogen at its natural isotopic composition.

"Isotopic enrichment" refers to the percentage of incorporation of an amount of a specific isotope at a given atom in a molecule in the place of that atom's natural isotopic abundance. For example, deuterium enrichment of 10% at a given position means that 10% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

"Isotopically enriched" refers to an atom having an isotopic composition other than the natural isotopic composition of that atom. "Isotopically enriched" may also refer to a compound containing at least one atom having an isotopic composition other than the natural isotopic composition of that atom.

As used herein, "alkyl," "cycloalkyl," "alkenyl," "cycloalkenyl," "alkynyl," "aryl," "alkoxy," "alkoxycarbonyl," "amino," "carboxyl," "alkylamino," "arylamino," "thioalkyoxy," "heterocyclyl," "heteroaryl," "alkylheterocyclyl," "alkylheteroaryl," "acyl," "aralkyl," "alkaryl," "purine," "pyrimidine," "carboxyl" and "amino acid" groups optionally comprise deuterium at one or more positions where hydrogen atoms are present, and wherein the deuterium composition of the atom or atoms is other than the natural isotopic composition.

Also as used herein, "alkyl," "cycloalkyl," "alkenyl," "cycloalkenyl," "alkynyl," "aryl," "alkoxy," "alkoxycarbonyl," "carboxyl," "alkylamino," "arylamino," "thioalkyoxy," "heterocyclyl," "heteroaryl," "alkylheterocyclyl," "alkylheteroaryl," "acyl," "aralkyl," "alkaryl," "purine," "pyrimidine," "carboxyl" and "amino acid" groups optionally comprise carbon-13 at an amount other than the natural isotopic composition.

As used herein, $EC_{50}$ refers to a dosage, concentration or amount of a particular test compound that elicits a dosedependent response at 50% of maximal expression of a particular response that is induced, provoked or potentiated by the particular test compound.

As used herein, the $IC_{50}$ refers to an amount, concentration or dosage of a particular test compound that achieves a 50% inhibition of a maximal response in an assay that measures such response.

The term "host," as used herein, refers to any unicellular or multicellular organism in which a virus can replicate, including cell lines and animals, and in certain embodiments, a human. Alternatively, a host can be carrying a part of a viral genome, whose replication or function can be altered by the compounds and compositions described herein. The term host specifically includes infected cells, cells transfected with all or part of a viral genome and animals, in particular, primates (including chimpanzees) and humans. In most animal applications, the host is a human patient. Veterinary applications, in certain indications, however, are clearly anticipated by the present disclosure (such as chimpanzees).

As used herein, the terms "subject" and "patient" are used interchangeably herein. The terms "subject" and "subjects" refer to an animal, such as a mammal including a non-primate (e.g., a cow, pig, horse, cat, dog, rat, and mouse) and a primate (e.g., a monkey such as a cynomolgous monkey, a chimpanzee and a human), and for example, a human. In certain embodiments, the subject is refractory or non-responsive to current treatments for hepatitis C infection. In another embodiment, the subject is a farm animal (e.g., a horse, a cow, a pig, etc.) or a pet (e.g., a dog or a cat). In certain embodiments, the subject is a human.

As used herein, the terms "therapeutic agent" and "therapeutic agents" refer to any agent(s) which can be used in the treatment or prevention of a disorder or one or more symptoms thereof. In certain embodiments, the term "therapeutic agent" includes a compound provided herein. In certain embodiments, a therapeutic agent is an agent which is known to be useful for, or has been or is currently being used for the treatment or prevention of a disorder or one or more symptoms thereof.

"Therapeutically effective amount" refers to an amount of a compound or composition that, when administered to a subject for treating a disease, is sufficient to effect such treatment for the disease. A "therapeutically effective amount" can vary depending on, inter alia, the compound, the disease and its severity, and the age, weight, etc., of the subject to be treated.

"Treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying the onset of the disease or disorder.

As used herein, the terms "prophylactic agent" and "prophylactic agents" as used refer to any agent(s) which can be used in the prevention of a disorder or one or more symptoms thereof. In certain embodiments, the term "prophylactic agent" includes a compound provided herein. In certain other embodiments, the term "prophylactic agent" does not refer a compound provided herein. For example, a prophylactic agent is an agent which is known to be useful for, or has been or is currently being used to prevent or impede the onset, development, progression and/or severity of a disorder.

As used herein, the phrase "prophylactically effective amount" refers to the amount of a therapy (e.g., prophylactic agent) which is sufficient to result in the prevention or reduction of the development, recurrence or onset of one or more symptoms associated with a disorder (or to enhance or improve the prophylactic effect(s) of another therapy (e.g., another prophylactic agent).

The term "substantially pure" with respect to a composition comprising a modified amino acid residue refers to a composition that includes at least 80, 85, 90 or 95% by weight or, in certain embodiments, 95, 98, 99 or 100% by weight, e.g. dry weight, of the modified amino acid residue relative to the remaining portion of the composition. The weight percentage can be relative to the total weight of protein in the composition or relative to the total weight of modified amino acid residues in the composition. Purity can be determined by techniques apparent to those of skill in the art.

The term "antibody" refers to any macromolecule that would be recognized as an antibody by those of skill in the art. Antibodies share common properties including binding and at least one polypeptide chain that is substantially identical to a polypeptide chain that can be encoded by any of the immunoglobulin genes recognized by those of skill in the art. The immunoglobulin genes include, but are not limited to, the κ, λ, α, γ (IgG1, IgG2, IgG3, and IgG4), δ, ε and μ constant region genes, as well as the immunoglobulin variable region genes. The term includes full-length antibodies and antibody fragments recognized by those of skill in the art, and variants thereof.

The term "antibody fragment" refers to any form of an antibody other than the full-length form. Antibody fragments herein include antibodies that are smaller components that exist within full-length antibodies, and antibodies that have been engineered. Antibody fragments include but are not limited to Fv, Fc, Fab, and $(Fab')_2$, single chain Fv (scFv), diabodies, triabodies, tetrabodies, bifunctional hybrid antibodies, CDR1, CDR2, CDR3, combinations of CDR's, variable regions, framework regions, constant regions, and the like (Maynard & Georgiou, 2000, *Annu. Rev. Biomed. Eng.* 2:339-76; Hudson, 1998, *Curr. Opin. Biotechnol.* 9:395-402).

The term "immunoglobulin (Ig)" refers to a protein consisting of one or more polypeptides substantially encoded by one of the immunoglobulin genes, or a protein substantially identical thereto in amino acid sequence. Immunoglobulins include but are not limited to antibodies. Immunoglobulins may have a number of structural forms, including but not limited to full-length antibodies, antibody fragments, and individual immunoglobulin domains including but not limited to $V_H$, Cγ1, Cγ2, Cγ3, $V_L$, and $C_L$.

The term "immunoglobulin (Ig) domain" refers to a protein domain consisting of a polypeptide substantially encoded by an immunoglobulin gene. Ig domains include but are not limited to $V_H$, $Cγ_1$, $Cγ_2$, $Cγ_3$, $V_L$, and $C_L$.

The term "variable region" of an antibody refers to a polypeptide or polypeptides composed of the $V_H$ immunoglobulin domain, the $V_L$ immunoglobulin domains, or the $V_H$ and $V_L$ immunoglobulin domains. Variable region may refer to this or these polypeptides in isolation, as an Fv fragment, as a scFv fragment, as this region in the context of a larger antibody fragment, or as this region in the context of a full-length antibody or an alternative, non-antibody scaffold molecule.

The term "variable" refers to the fact that certain portions of the variable domains differ extensively in sequence among antibodies and are responsible for the binding specificity of each particular antibody for its particular antigen. However, the variability is not evenly distributed through the variable domains of antibodies. It is concentrated in three segments called Complementarity Determining Regions (CDRs) both in the light chain and the heavy chain variable domains. The more highly conserved portions of the variable domains are called the framework regions (FR). The variable domains of native heavy and light chains each comprise four FR regions, largely adopting a β-sheet configuration, connected by three or four CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat et al., Sequences of Proteins of Immunological Interest, 5th Ed. Public Health Service, National Institutes of Health, Bethesda, Md. (1991)).

The constant domains are not typically involved directly in binding an antibody to an antigen, but exhibit various effector functions. Depending on the amino acid sequence of the constant region of their heavy chains, antibodies or immunoglobulins can be assigned to different classes. There are five major classes of immunoglobulins: IgA, IgD, IgE, IgG and IgM, and several of these may be further divided into subclasses (isotypes), e.g. IgG1, IgG2, IgG3, and IgG4; IgA1 and IgA2. The heavy chain constant regions that correspond to the different classes of immunoglobulins are called α, δ, ε, γ and μ, respectively. Of the various human immunoglobulin classes, only human IgG1, IgG2, IgG3 and IgM are known to activate complement.

The term "conjugate" refers to any moiety that can be connected to a modified amino acid residue as described herein. In some embodiments, the terms "conjugate" and "payload" are used interchangeably. A conjugate can be a small molecule or a macromolecule. In some embodiments, the conjugate is a bioactive molecule including, but not limited to, a protein, a peptide, a nucleic active or a hybrid thereof. In some embodiments, the conjugate is a polymer such as polyethylene glycol. In some embodiments, a conjugate is a therapeutic agent, including a commercially available drug. In some embodiments, a conjugate is a label that can recognize and bind to specific targets, such as a molecular payload that is harmful to target cells or a label useful for detection or diagnosis. In some embodiments, the conjugate is connected to a modified amino acid residue via a linker. In some embodiments, the conjugate is directly connected to a modified amino acid residue without a linker.

The term "variant protein sequence" refers to a protein sequence that has one or more residues that differ in amino acid identity from another similar protein sequence. Said similar protein sequence may be the natural wild type protein sequence, or another variant of the wild type sequence. Variants include proteins that have one or more amino acid insertions, deletions or substitutions. Variants also include proteins that have one or more post-translationally modified amino acids.

The term "parent antibody" refers to an antibody known to those of skill in the art that is modified according to the description provided herein. The modification can be physical, i.e., chemically or biochemically replacing or modifying one or more amino acids of the parent antibody to yield an antibody within the scope of the present description. The modification can also be conceptual, i.e., using the sequence of one or more polypeptide chains of the parent antibody to design an antibody comprising one or more site-specific modified amino acids according to the present description. Parent antibodies can be naturally occurring antibodies or antibodies designed or developed in a laboratory. Parent antibodies can also be artificial or engineered antibodies, e.g., chimeric or humanized antibodies.

The term "conservatively modified variant" refers to a protein that differs from a related protein by conservative substitutions in amino acid sequence. One of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

See, e.g., Creighton, *Proteins: Structures and Molecular Properties*, W H Freeman & Co.; 2nd edition (December 1993).

The terms "identical" or "identity," in the context of two or more polypeptide sequences, refer to two or more sequences or subsequences that are the same. Sequences are "substantially identical" if they have a percentage of amino acid residues or nucleotides that are the same (i.e., about 60% identity, optionally about 65%, about 70%, about 75%, about 80%, about 85%, about 90%, or about 95% identity over a specified region), when compared and aligned for maximum correspondence over a comparison window, or designated region as measured using one of the following sequence comparison algorithms or by manual alignment and visual inspection. The identity can exist over a region that is at least about 50 amino acids or nucleotides in length, or over a region that is 75-100 amino acids or nucleotides in length, or, where not specified, across the entire sequence or a polypeptide. In the case of antibodies, identity can be measured outside the variable CDRs. Optimal alignment of sequences for comparison can be conducted, including but not limited to, by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.); or by manual alignment and visual inspection (see, e.g., Ausubel et al., Current Protocols in Molecular Biology (1995 supplement)).

Examples of algorithms that are suitable for determining percent sequence identity and sequence similarity include the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands. The BLAST algorithm is typically performed with the "low complexity" filter turned off. In some embodiments, the BLAST algorithm is typically performed with the "low complexity" filter turned on.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "amino acid" refers to naturally occurring and non-naturally occurring amino acids, as well as amino acids such as proline, amino acid analogs and amino acid mimetics that function in a manner similar to naturally occurring amino acids.

Naturally encoded amino acids are the proteinogenic amino acids known to those of skill in the art. They include the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and the less common pyrrolysine and selenocysteine. Naturally encoded amino acids include post-translational variants of the 22 naturally occurring amino acids such as prenylated amino acids, isoprenylated amino acids, myrisoylated amino acids, palmitoylated amino acids, N-linked glycosylated amino acids, O-linked glycosylated amino acids, phosphorylated amino acids and acylated amino acids.

The term "modified amino acid" refers to an amino acid that is not a proteinogenic amino acid, or a post-translationally modified variant thereof. In particular, the term refers to an amino acid that is not one of the 20 common amino acids or pyrrolysine or selenocysteine, or post-translationally modified variants thereof.

Compounds

Provided herein are compounds according to formula I:

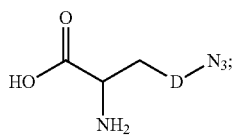

Formula I or a salt thereof, wherein: D is —Ar—$W_3$— or —$W_1$—$Y_1$—C(O)—$Y_2$—$W_2$—; Ar is

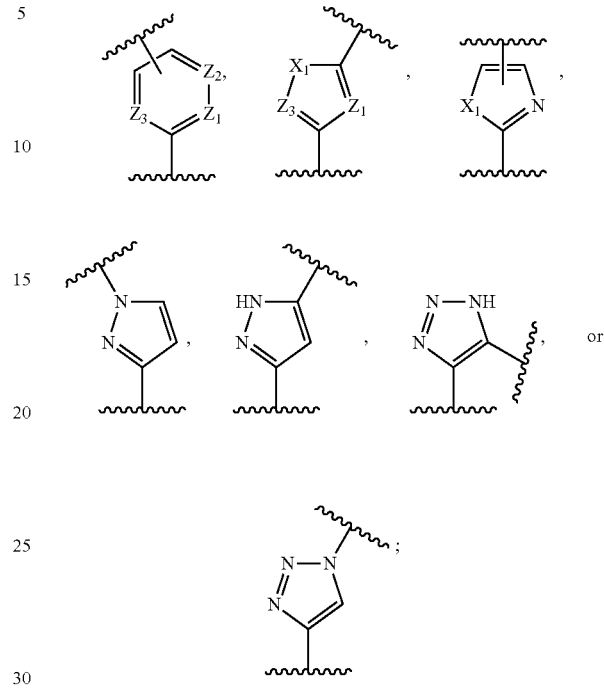

each of $W_1$, $W_2$, and $W_3$ is independently a single bond or lower alkylene; each $X_1$ is independently —NH—, —O—, or —S—; each $Y_1$ is independently a single bond, —NH—, or —O—; each $Y_2$ is independently a single bond, —NH—, —O—, or an N-linked or C-linked pyrrolidinylene; and one of $Z_1$, $Z_2$, and $Z_3$ is —N— and the others of $Z_1$, $Z_2$, and $Z_3$ are independently —CH—.

In an embodiment, D is —Ar—$W_3$—; and Ar and $W_3$ are as defined in the context of formula I. In a particular embodiment, D is —Ar—$W_3$—; and Ar is

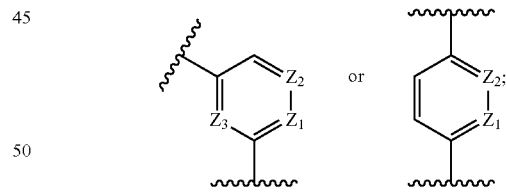

and Ar, $Z_1$, $Z_2$, $Z_3$ and $W_3$ are as defined in the context of formula I. In certain embodiments, D is —Ar—$W_3$—; and Ar is

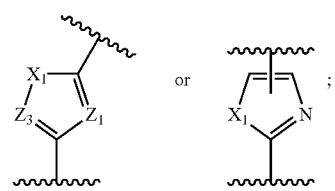

and Ar, $Z_1$, $Z_3$, $X_1$ and $W_3$ are as defined in the context of formula I. In certain embodiments, D is —Ar—$W_3$—; $W_3$ is —$CH_2$—; and Ar is

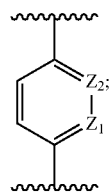

where $Z_1$ and $Z_2$ are as defined in the context of formula I.

In an embodiment, D is —$W_1$—$Y_1$—C(O)—$Y_2$—$W_2$—; and $W_1$, $W_2$, $Y_1$, and $Y_2$ are as defined in the context of formula I. In particular embodiments, D is —$W_1$—$Y_1$—C(O)—$Y_2$—$W_2$—; and each $Y_1$ is independently —NH— or —O—; and $W_1$, $W_2$ and $Y_2$ are as defined in the context of formula I. In certain embodiments, D is —$W_1$—$Y_1$—C(O)—$Y_2$—$W_2$—; each $Y_2$ is independently an N-linked or C-linked pyrrolidinylene; and each $W_2$ is a single bond; and $W_1$ and $Y_1$ are as defined in the context of formula I. In a particular embodiment, D is —$W_1$—$Y_1$—C(O)—$Y_2$—$W_2$—; each $Y_2$ is independently a single bond, —NH— or —O—; and each $W_2$ is lower alkylene; and $W_1$ and $Y_1$ are as defined in the context of formula I.

In an embodiment, a compound according to formula Ia is provided:

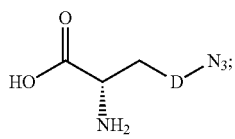

Formula Ia where D is a defined in the context of formula I.

In an embodiment, compounds of either of formulas I and Ia are provided wherein each of $W_2$ and $W_3$ is independently $C_1$-$C_3$ alkylene. In another embodiment, compounds of either of formulas I and Ia are provided wherein each of $W_2$ and $W_3$ is independently $C_1$-$C_2$ alkylene.

In an embodiment, a compound according to formula II is provided:

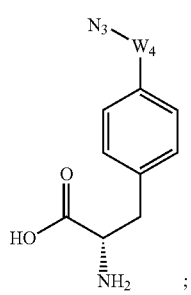

Formula II or a salt thereof, wherein $W_4$ is $C_1$-$C_{10}$ alkylene. In a further embodiment, $W_4$ is $C_1$-$C_5$ alkylene. In an embodiment, $W_4$ is $C_1$-$C_3$ alkylene. In an embodiment, $W_4$ is $C_1$ alkylene.

In an embodiment, a compound according to formula 30 is provided:

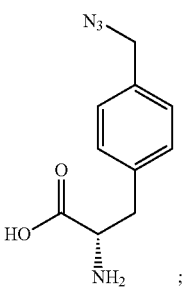

(30)

or a salt thereof.

In an embodiment, a compound according to any of formulas 1-29 and 40 is provided:

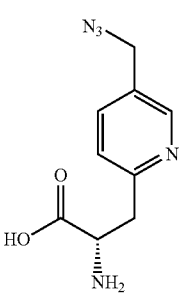

(1)

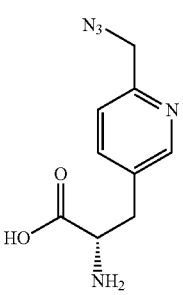

(2)

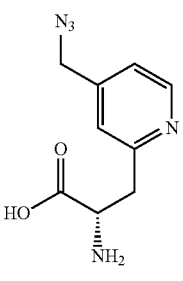

(3)

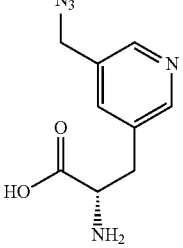

(4)

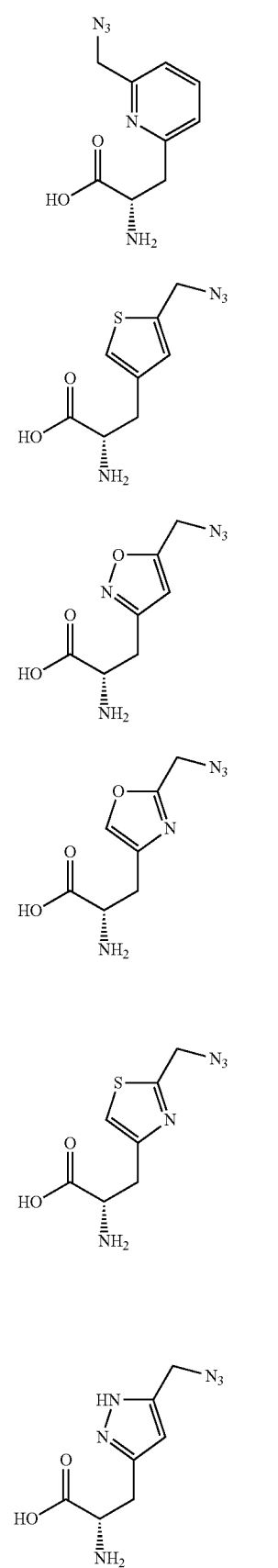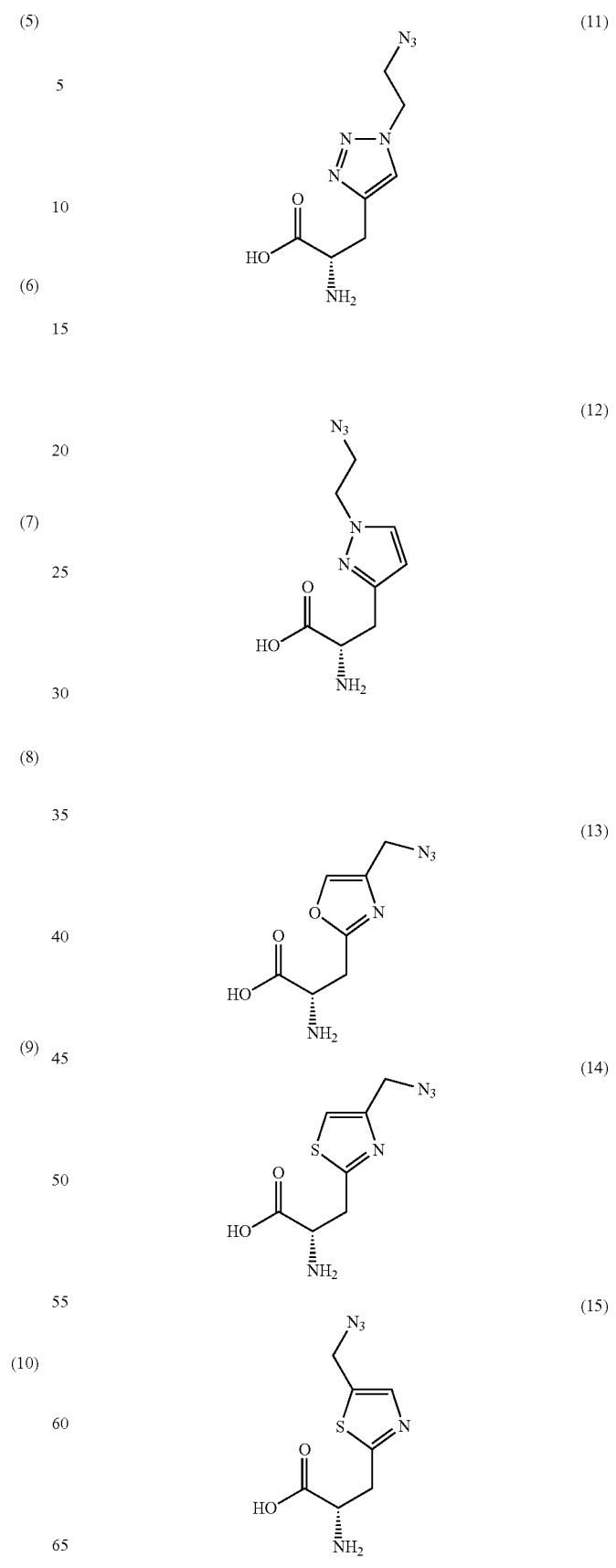

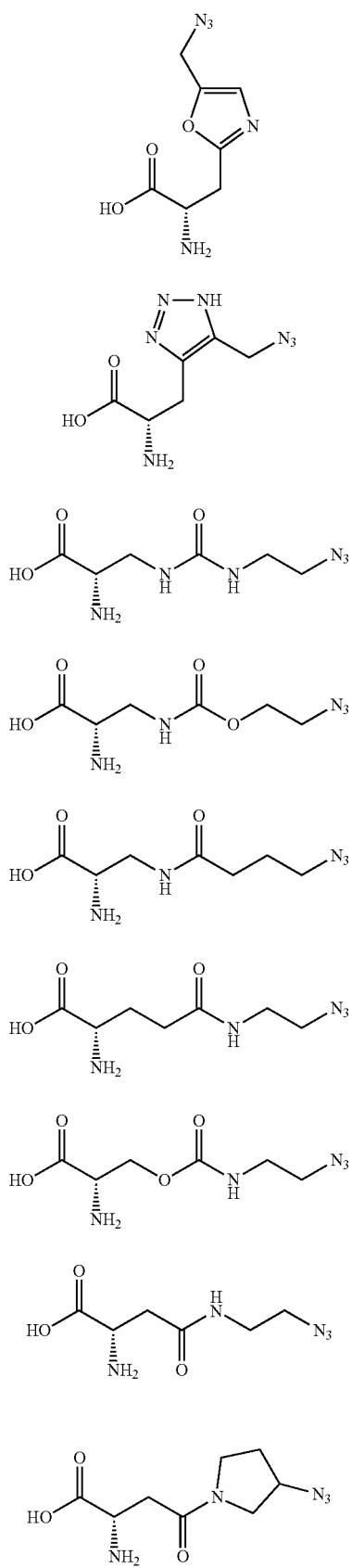

or a salt thereof.

In an embodiment, a polypeptide is provided comprising an amino acid residue corresponding to a compound of formula I, Ia, II, 1-30 or 40. In an embodiment, a conjugate is provided comprising a polypeptide comprising an amino acid residue corresponding to a compound of formula I, Ia, II, 1-30 or 40 linked to a payload and optionally comprising a linking moiety between the polypeptide and the payload.

In an embodiment, an antibody is provided comprising an amino acid residue corresponding to a compound of formula I, Ia, II, 1-30 or 40. In an embodiment, a conjugate is provided comprising an antibody comprising an amino acid residue corresponding to a compound of formula I, Ia, II, 1-30 or 40 linked to a payload and optionally comprising a linking moiety between the antibody and the payload.

In an embodiment, an orthogonal tRNA is provided aminoacylated with an amino acid residue corresponding to a compound of formula I, Ia, II, 1-30 or 40. In a related embodiment, a method of producing a polypeptide is provided, comprising contacting a polypeptide with an orthogonal tRNA aminoacylated with an amino acid residue corresponding to a compound of formula I, Ia, II, 1-30 or 40 under conditions suitable for incorporating the amino acid residue into the polypeptide. In an aspect, the orthogonal tRNA base pairs with a codon that is not normally associated with an amino acid. In another aspect, the contacting occurs in a reaction mixture which comprises a tRNA synthetase capable of aminoacylating the orthogonal tRNA with a compound of formula I, Ia, II, 1-30 or 40.

In certain embodiments, a polypeptide comprising a modified amino acid residue is provided according to any of the following formulas, where D is as defined in the context of formula I.

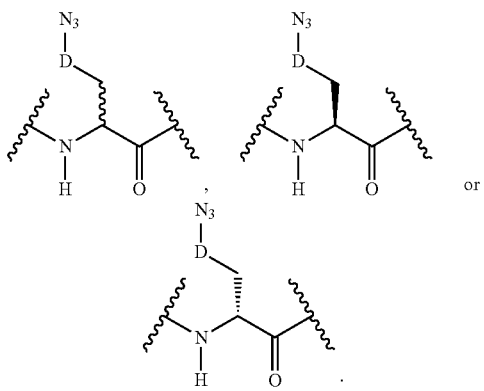

Those of skill in the art will recognize that proteins are generally comprised of L-amino acids. However, with modified amino acids, the present methods and compositions provide the practitioner with the ability to use L-, D- or racemic modified amino acids. In certain embodiments, the modified amino acids described herein include D-versions of the natural amino acids and racemic versions of the natural amino acids.

Huisgen Cycloaddition Reaction

Advantageously, the modified amino acids comprising azido groups, such as compounds according to any of formulas I, Ia, II, 1-30 or 40, provided herein and the polypeptides comprising them facilitate selective and efficient reactions with a second compound comprising an alkyne group. It is believed the azido and alkyne groups react in a 1,3-dipolar cycloaddition reaction to form a 1,2,3-triazolylene moiety which links the modified amino acid (or polypeptide comprising the modified amino acid) to the second compound. This reaction between an azide and alkyne to form a triazole is generally known to those in the art as a Huisgen cycloaddition reaction.

The unique reactivity of azide and alkyne functional groups makes them extremely useful for the selective modification of polypeptides and other biological molecules. Organic azides, particularly aliphatic azides, and alkynes are generally stable toward common reactive chemical conditions. In particular, both the azide and the alkyne functional groups are inert toward the side chains (i.e., R groups) of the 20 common amino acids found in naturally-occurring polypeptides. When brought into close proximity, however, the "spring-loaded" nature of the azide and alkyne groups is revealed and they react selectively and efficiently via Huisgen [3+2] cycloaddition reaction to generate the corresponding triazole. See, e.g., Chin J., et al., Science 301:964-7 (2003); Wang, Q., et al., J. Am. Chem. Soc. 125, 3192-3193 (2003); Chin, J. W., et al., J. Am. Chem. Soc. 124:9026-9027 (2002).

Because the Huisgen cycloaddition reaction involves a selective cycloaddition reaction (see, e.g., Padwa, A., in COMPREHENSIVE ORGANIC SYNTHESIS, Vol. 4, (ed. Trost, B. M., 1991), p. 1069-1109; Huisgen, R. in 1,3-DIPOLAR CYCLOADDITION CHEMISTRY, (ed. Padwa, A., 1984), p. 1-176) rather than a nucleophilic substitution, the incorporation of non-naturally encoded amino acids bearing azide and alkyne-containing side chains permits the resultant polypeptides to be modified selectively at the position of the non-naturally encoded amino acid. Cycloaddition reaction involving azide or alkyne-containing compounds can be carried out at room temperature under aqueous conditions by the addition of Cu(II) (including but not limited to, in the form of a catalytic amount of $CuSO_4$) in the presence of a reducing agent for reducing Cu(II) to Cu(I), in situ, in catalytic amount. See, e.g., Wang, Q., et al., J. Am. Chem. Soc. 125, 3192-3193 (2003); Tomoe, C. W., et al., J. Org. Chem. 67:3057-3064 (2002); Rostovtsev, et al., Angew. Chem. Int. Ed. 41:2596-2599 (2002). Exemplary reducing agents include, including but not limited to, ascorbate, metallic copper, quinine, hydroquinone, vitamin K, glutathione, cysteine, $Fe^{2+}$, $Co^{2+}$, and an applied electric potential.

Polypeptides

Provided herein are polypeptides comprising one or more modified amino acid residues at site-specific positions in an amino acid sequence of at least one polypeptide chain. In an embodiment, the compositions are antibodies comprising one or more modified amino acid residues at site-specific positions in the amino acid sequence of at least one polypeptide chain.

The polypeptide can share high sequence identity with any polypeptide recognized by those of skill in the art, i.e. a parent polypeptide. In certain embodiments, the amino acid sequence of the polypeptide is identical to the amino acid sequence of the parent polypeptide, other than the modified amino acids at site-specific positions. In further embodiments, the polypeptide provided herein can have one or more insertions, deletions or mutations relative to the parent polypeptide in addition to the one or more modified amino acids at the site-specific positions. In certain embodiments, the polypeptide provided herein can have a unique primary sequence, so long as it would be recognized as a polypeptide by those of skill in the art. In certain aspects of this embodiment, the polypeptide is an antibody.

The compositions and methods described herein provide for the incorporation of at least one modified amino acid into a polypeptide. The modified amino acid may be present at any location on the polypeptide, including any terminal position or any internal position of the polypeptide. Preferably, the modified amino acid does not destroy the activity and/or the tertiary structure of the polypeptide relative to the homologous naturally-occurring amino acid polypeptide, unless such destruction of the activity and/or tertiary structure was one of the purposes of incorporating the modified amino acid into the polypeptide. Further, the incorporation of the modified amino acid into the polypeptide may modify to some extent the activity (e.g., manipulating the therapeutic effectiveness of the polypeptide, improving the safety profile of the polypeptide, adjusting the pharmacokinetics, pharmacologics and/or pharmacodynamics of the polypeptide (e.g., increasing water solubility, bioavailability, increasing serum half-life, increasing therapeutic half-life, modulating immunogenicity, modulating biological activity, or extending the circulation time), providing additional functionality to the polypeptide, incorporating a tag, label or detectable signal into the polypeptide, easing the isolation properties of the polypeptide, and any combination of the aforementioned modifications) and/or tertiary structure of the polypeptide relative to the homologous naturally-occurring amino acid polypeptide without fully causing destruction of the activity and/or tertiary structure. Such modifications of the activity and/or tertiary structure are often one of the goals of effecting such incorporations, although the incorporation of the modified amino acid into the polypeptide may also have little effect on the activity and/or tertiary structure of the polypeptide relative to the homologous naturally-occurring amino acid polypeptide. Correspondingly, modified amino acid polypeptides, compositions comprising modified amino acid polypeptides, methods for making such polypeptides and polypeptide compositions, methods for purifying, isolating, and characterizing such polypeptides and polypeptide compositions, and methods for using such polypeptides and polypeptide compositions are considered within the scope of the present disclosure. Further, the modified amino acid polypeptides described herein may also be ligated to another polypeptide (including, by way of example, a modified amino acid polypeptide or a naturally-occurring amino acid polypeptide).

The methods, compositions, strategies and techniques described herein are not limited to a particular type, class or family of polypeptides or proteins. Indeed, virtually any polypeptide may include at least one modified amino acids described herein. By way of example only, the polypeptide can be homologous to a therapeutic protein selected from the group consisting of: alpha-1 antitrypsin, angiostatin, antihemolytic factor, antibody, apolipoprotein, apoprotein, atrial natriuretic factor, atrial natriuretic polypeptide, atrial peptide, C-X-C chemokine, T39765, NAP-2, ENA-78, gro-a, gro-b, gro-c, IP-10, GCP-2, NAP-4, SDF-1, PF4, MIG, calcitonin, c-kit ligand, cytokine, CC chemokine, monocyte chemoattractant protein-1, monocyte chemoattractant protein-2, monocyte chemoattractant protein-3, monocyte inflammatory protein-1 alpha, monocyte inflammatory protein-1beta, RANTES, 1309, R83915, R91733, HCC1, T58847, D31065, T64262, CD40, CD40 ligand, c-kit ligand, collagen, colony stimulating factor (CSF), complement factor 5a, complement inhibitor, complement receptor 1, cytokine, epithelial neutrophil activating peptide-78, MIP-16, MCP-1, epidermal growth factor (EGF), epithelial neutrophil activating peptide, erythropoietin (EPO), exfoliating toxin, Factor IX, Factor VII, Factor VIII, Factor X, fibroblast growth factor (FGF), fibrinogen, fibronectin, four-helical bundle protein, G-CSF, glp-1, GM-CSF, glucocerebrosidase, gonadotropin, growth factor, growth factor receptor, grf, hedgehog protein, hemoglobin, hepatocyte growth factor (hGF), hirudin, human growth hormone (hGH), human serum albumin, ICAM-1, ICAM-1 receptor, LFA-1, LFA-1 receptor, insulin, insulin-like growth factor (IGF), IGF-I, IGF-II, interferon (IFN), IFN-alpha, IFN-beta, IFN-gamma, interleukin (IL), IL-1, IL-2, IL-3, IL-4, IL-5, IL-6, IL-7, IL-8, IL-9, IL-10, IL-11, IL-12, keratinocyte growth factor (KGF), lactoferrin, leukemia inhibitory factor, luciferase, neurturin, neutrophil inhibitory factor (NIF), oncostatin M, osteogenic protein, oncogene product, paracitonin, parathyroid hormone, PD-ECSF, PDGF, peptide hormone, pleiotropin, protein A, protein G, pth, pyrogenic exotoxin A, pyrogenic exotoxin B, pyrogenic exotoxin C, pyy, relaxin, renin, SCF, small biosynthetic protein, soluble complement receptor I, soluble I-CAM 1, soluble interleukin receptor, soluble TNF receptor, somatomedin, somatostatin, somatotropin, streptokinase, superantigens, staphylococcal enterotoxin, SEA, SEB, SECT, SEC2, SEC3, SED, SEE, steroid hormone receptor, superoxide dismutase, toxic shock syndrome toxin, thymosin alpha 1, tissue plasminogen activator, tumor growth factor (TGF), tumor necrosis factor, tumor necrosis factor alpha, tumor necrosis factor beta, tumor necrosis factor receptor (TNFR), VLA-4 protein, VCAM-1 protein, vascular endothelial growth factor (VEGF), urokinase, mos, ras, raf, met, p53, tat, fos, myc, jun, myb, rel, estrogen receptor, progesterone receptor, testosterone receptor, aldosterone receptor, LDL receptor, and corticosterone. In a related or further embodiment, the modified amino acid polypeptide may also be homologous to any polypeptide member of the growth hormone supergene family.

In certain embodiments, the modified amino acids can be at any position within the polypeptide—at the N-terminus, at the C-terminus, or within the polypeptide. In advantageous embodiments, the modified amino acids are positioned at select locations in a polypeptide. These locations are identified as providing optimum sites for substitution with the modified amino acids. Each site is capable of bearing a modified amino acid with optimum structure, function and/or methods for producing the polypeptide.

In certain embodiments, a site-specific position for substitution provides a polypeptide that is stable. Stability can be measured by any technique apparent to those of skill in the art.

In certain embodiments, a site-specific position for substitution provides a polypeptide that is has optimal functional properties. For instance, the polypeptide can show little or no loss of binding affinity for its target compared to a polypeptide without the site-specific modified amino acid. In certain embodiments, the polypeptide can show enhanced binding compared to a polypeptide without the site-specific modified amino acid. In certain aspects of this embodiment, the polypeptide is an antibody and the target is an antigen.

In certain embodiments, a site-specific position for substitution provides a polypeptide that can be made advantageously. For instance, in certain embodiments, the polypeptide shows advantageous properties in its methods of synthesis, discussed herein. In certain embodiments, the polypeptide can show little or no loss in yield in production compared to a polypeptide without the site-specific modified amino acid. In certain embodiments, the polypeptide can show enhanced yield in production compared to a polypeptide without the site-specific modified amino acid. In certain embodiments, the polypeptide can show little or no loss of tRNA suppression, described herein, compared to a polypeptide without the site-specific modified amino acid. In certain embodiments, the polypeptide can show enhanced tRNA suppression, described herein, in production compared to a polypeptide without the site-specific modified amino acid. In certain aspects of this embodiment, the polypeptide is an antibody.

In certain embodiments, a site-specific position for substitution provides a polypeptide that has advantageous solubility. In certain embodiments, the polypeptide can show little or no loss in solubility compared to a polypeptide without the site-specific modified amino acid. In certain embodiments, the polypeptide can show enhanced solubility compared to a polypeptide without the site-specific modified amino acid. In certain aspects of this embodiment, the polypeptide is an antibody.

In certain embodiments, a site-specific position for substitution provides a polypeptide that has advantageous expression. In certain embodiments, the polypeptide can show little or no loss in expression compared to a polypeptide without the site-specific modified amino acid. In certain embodiments, the polypeptide can show enhanced expression compared to a polypeptide without the site-specific modified amino acid. In certain aspects of this embodiment, the polypeptide is an antibody.

In certain embodiments, a site-specific position for substitution provides a polypeptide that has advantageous folding. In certain embodiments, the polypeptide can show little or no loss in proper folding compared to a polypeptide without the site-specific modified amino acid. In certain embodiments, the polypeptide can show enhanced folding compared to a polypeptide without the site-specific modified amino acid. In certain aspects of this embodiment, the polypeptide is an antibody.

In certain embodiments, a site-specific position for substitution provides a polypeptide that is capable of advantageous conjugation. As described herein, several modified amino acids have side chains or functional groups that facilitate conjugation of the polypeptide to a second agent, either directly or via a linker. In certain embodiments, the polypeptide can show enhanced conjugation efficiency compared to a polypeptide without the same or other modified amino acids at other positions. In certain embodiments, the polypeptide can show enhanced conjugation yield compared to a polypeptide without the same or other modified amino acids at other positions. In certain embodiments, the polypeptide can show enhanced conjugation specificity compared to a polypeptide without the same or other modified amino acids at other positions. In certain aspects of this embodiment, the polypeptide is an antibody.

In certain embodiments, further provided herein are conservatively modified variants of the polypeptides and antibodies described herein. Conservatively modified variants of a polypeptide include one or more insertions, deletions or substitutions that do not disrupt the structure and/or function of the polypeptide when evaluated by one of skill in the art. In certain embodiments, conservatively modified variants include 20 or fewer amino acid insertions, deletions or substitutions. In certain embodiments, conservatively modified variants include 15 or fewer amino acid insertions, deletions or substitutions. In certain embodiments, conservatively modified variants include 10 or fewer amino acid insertions, deletions or substitutions. In certain embodiments, conservatively modified variants include 9 or fewer amino acid insertions, deletions or substitutions. In certain embodiments, conservatively modified variants include 8 or fewer amino acid insertions, deletions or substitutions. In certain embodiments, conservatively modified variants include 7 or fewer amino acid insertions, deletions or substitutions. In certain embodiments, conservatively modified variants include 6 or fewer amino acid insertions, deletions or substitutions. In certain embodiments, conservatively modified variants include 5 or fewer amino acid insertions, deletions or substitutions. In certain embodiments, conservatively modified variants include 4 or fewer amino acid insertions, deletions or substitutions. In certain embodiments, conservatively modified variants include 3 or fewer amino acid insertions, deletions or substitutions. In certain embodiments, conservatively modified variants include 2 or fewer amino acid insertions, deletions or substitutions. In certain embodiments, conservatively modified variants include 1 amino acid insertion, deletion or substitution. In particular embodiments the substitutions are conservative, substituting an amino acid within the same class, as described herein. In particular embodiments, the polypeptide is an antibody.

In certain embodiments, the polypeptides can be modified to modulate structure, stability and/or activity. In such embodiments, the modifications can be conservative or other than conservative. The modifications need only be suitable to the practitioner carrying out the methods and using the compositions described herein. In certain embodiments where the polypeptide is an antibody, the modifications decrease but do not eliminate antigen binding affinity. In certain embodiments where the polypeptide is an antibody, the modifications increase antigen binding affinity. In certain embodiments, the modifications enhance structure or stability of the polypeptide. In certain embodiments, the modifications reduce but do not eliminate structure or stability of the polypeptide. In certain embodiments, modified variants include 20 or fewer amino acid insertions, deletions or substitutions. In certain embodiments, modified variants include 15 or fewer amino acid insertions, deletions or substitutions. In certain embodiments, modified variants include 10 or fewer amino acid insertions, deletions or substitutions. In certain embodiments, modified variants include 9 or fewer amino acid insertions, deletions or substitutions. In certain embodiments, modified variants include 8 or fewer amino acid insertions, deletions or substitutions. In certain embodiments, modified variants include 7 or fewer amino acid insertions, deletions or substitutions. In certain embodiments, modified variants include 6 or fewer amino acid insertions, deletions or substitutions. In certain embodiments, modified variants include 5 or fewer amino acid insertions, deletions or substitutions. In certain embodiments, modified variants include 4 or fewer amino acid insertions, deletions or substitutions. In certain embodiments, modified variants include 3 or fewer amino acid insertions, deletions or substitutions. In certain embodiments, modified variants include 2 or fewer amino acid insertions, deletions or substitutions. In certain embodiments, modified variants include 1 amino acid insertion, deletion or substitution.

Also within the scope are post-translationally modified variants. Any of the polypeptides provided herein can be post-translationally modified in any manner recognized by those of skill in the art. Typical post-translational modifications for polypeptides include interchain disulfide bonding, intrachain disulfide bonding, N-linked glycosylation and proteolysis. Also provided herein are other post-translationally modified polypeptides having modifications such as phosphorylation, O-linked glycosylation, methylation, acetylation, lipidation, GPI anchoring, myristoylation and prenylation. The post-translational modification can occur during production, in vivo, in vitro or otherwise. In certain embodiments, the post-translational modification can be an intentional modification by a practitioner, for instance, using the methods provided herein. In particular embodiments, the polypeptide is an antibody.

Further included are polypeptides fused to further peptides or polypeptides. Exemplary fusions include, but are not limited to, e.g., a methionyl polypeptide in which a methionine is linked to the N-terminus of the polypeptide resulting from the recombinant expression, fusions for the purpose of purification (including but not limited to, to poly-histidine or affinity epitopes), fusions for the purpose of linking to other biologically active molecules, fusions with serum albumin binding peptides, and fusions with serum proteins such as serum albumin. The polypeptides may comprise protease cleavage sequences, reactive groups, polypeptide-binding domains (including but not limited to, FLAG or poly-His) or other affinity based sequences (including but not limited to, FLAG, poly-His, GST, etc.). The polypeptides may also comprise linked molecules (including but not limited to, biotin) that improve detection (including but not limited to, GFP), purification or other features of the polypeptide. In certain embodiments, the polypeptides comprise a C-terminal affinity sequence that facilitates purification of full length polypeptides. In certain embodiments, such C-terminal affinity sequence is a poly-His sequence, e.g., a 6-His sequence. In particular embodiments, the polypeptide is an antibody.

Also provided herein are polypeptides that are conjugated to one or more conjugation moieties. The conjugation moiety can be any conjugation moiety deemed useful to one of skill in the art. For instance, the conjugation moiety can be a polymer, such as polyethylene glycol, that can improve the stability of the polypeptide in vitro or in vivo. The conjugation moiety can have therapeutic activity, thereby yielding a polypeptide-drug conjugate. The conjugation moiety can be a molecular payload that is harmful to target cells. The conjugation moiety can be a label useful for detection or diagnosis. In certain embodiments, the conjugation moiety is linked to the polypeptide via a direct covalent bond. In certain embodiments, the conjugation moiety is linked to the polypeptide via a linker. In advantageous embodiments, the conjugation moiety or the linker is attached via one of the modified amino acids of the polypeptide. Exemplary conjugation moieties and linkers are described herein. In particular embodiments, the polypeptide is an antibody.

The parent polypeptide can be any polypeptide known to those of skill in the art, or later discovered, without limitation. In particular embodiments, the polypeptide is an antibody. The parent polypeptide may be substantially encoded by a polypeptide gene or polypeptide genes from any organism, including but not limited to humans, mice, rats, rabbits, camels, llamas, dromedaries, monkeys, particularly mammals and particularly human and particularly mice and rats. In one embodiment, the parent polypeptide may be fully human, obtained for example from a patient or subject, by using transgenic mice or other animals (see Bruggemann & Taussig, 1997, Curr. Opin. Biotechnol. 8:455-458 for antibody examples) or human polypeptide libraries coupled with selection methods (see Griffiths & Duncan, 1998, Curr. Opin. Biotechnol. 9:102-108 for antibody examples). The parent polypeptide may be from any source, including artificial or naturally occurring. For example, a parent polypeptide can be an engineered polypeptide, including but not limited to chimeric polypeptides and humanized polypeptides (see Clark, 2000, Immunol. Today 21:397-402 for antibody examples) or derived from a combinatorial library. In addition, the parent polypeptide may be an engineered variant of a polypeptide that is substantially encoded by one or more natural polypeptide genes. For example, in one embodiment the parent polypeptide is a polypeptide that has been identified by affinity maturation.

Parent polypeptides can be any polypeptide known in the art or any polypeptide developed by those of skill in the art without limitation. Antibody examples include, but are not limited to anti-TNF antibody (U.S. Pat. No. 6,258,562), anti-IL-12 and/or anti-IL-12p40 antibody (U.S. Pat. No. 6,914,128); anti-IL-18 antibody (U.S. Patent Publication No. 2005/0147610), anti-05, anti-CBL, anti-CD147, anti-gp120, anti-VLA-4, anti-CD11a, anti-CD18, anti-VEGF, anti-CD40L, anti CD-40 (e.g., see PCT Publication No. WO 2007/124299) anti-Id, anti-ICAM-1, anti-CXCL13, anti-CD2, anti-EGFR, anti-TGF-beta 2, anti-HGF, anti-cMet, anti DLL-4, anti-NPR1, anti-PLGF, anti-ErbB3, anti-E-selectin, anti-Fact VII, anti-Her2/neu, anti-F gp, anti-CD11/18, anti-CD14, anti-ICAM-3, anti-RON, anti-SOST, anti CD-19, anti-CD80 (e.g., see PCT Publication No. WO 2003/039486, anti-CD4, anti-CD3, anti-CD23, anti-beta2-integrin, anti-alpha4beta7, anti-CD52, anti-HLA DR, anti-CD22 (e.g., see U.S. Pat. No. 5,789,554), anti-CD20, anti-MIF, anti-CD64 (FcR), anti-TCR alpha beta, anti-CD2, anti-Hep B, anti-CA 125, anti-EpCAM, anti-gp120, anti-CMV, anti-gpIIbIIIa, anti-IgE, anti-CD25, anti-CD33, anti-HLA, anti-IGF1,2, anti IGFR, anti-VNRintegrin, anti-IL-1alpha, anti-IL-1beta, anti-IL-1 receptor, anti-IL-2 receptor, anti-IL-4, anti-IL-4 receptor, anti-IL5, anti-IL-5 receptor, anti-IL-6, anti-IL-8, anti-IL-9, anti-IL-13, anti-IL-13 receptor, anti-IL-17, anti-IL-6R, anti-RANKL, anti-NGF, anti-DKK, anti-alphaVbeta3, anti-IL-17A, anti-IL23p19 and anti-IL-23 (see Presta, L. G. (2005) J. Allergy Clin. Immunol. 116: 731-6).

Parent polypeptides may also be selected from various therapeutic polypeptides approved for use, in clinical trials, or in development for clinical use. Antibody examples of such therapeutic polypeptides include, but are not limited to, rituximab (Rituxan®, IDEC/Genentech/Roche) (see, for example, U.S. Pat. No. 5,736,137), a chimeric anti-CD20 antibody approved to treat Non-Hodgkin's lymphoma; HuMax-CD20, an anti-CD20 currently being developed by Genmab, an anti-CD20 antibody described in U.S. Pat. No. 5,500,362, AME-133 (Applied Molecular Evolution), hA20 (Immunomedics, Inc.), HumaLYM (Intracel), and PR070769 (PCT Application No. PCT/US2003/040426), trastuzumab (Herceptin®, Genentech) (see, for example, U.S. Pat. No. 5,677,171), a humanized anti-Her2/neu antibody approved to treat breast cancer; pertuzumab (rhuMab-2C4, Omnitarg®), currently being developed by Genentech; an anti-Her2 antibody (U.S. Pat. No. 4,753,894; cetuximab (Erbitux®, Imclone) (U.S. Pat. No. 4,943,533; PCT Publication No. WO 96/40210), a chimeric anti-EGFR antibody in clinical trials for a variety of cancers; ABX-EGF (U.S. Pat. No. 6,235,883), currently being developed by Abgenix-Immunex-Amgen; HuMax-EGFr (U.S. Pat. No. 7,247,301), currently being developed by Genmab; 425, EMD55900, EMD62000, and EMD72000 (Merck KGaA) (U.S. Pat. No. 5,558,864; Murthy, et al. (1987) Arch. Biochem. Biophys. 252(2): 549-60; Rodeck, et al. (1987) J. Cell. Biochem. 35(4): 315-20; Kettleborough, et al. (1991) Protein Eng. 4(7): 773-83); ICR62 (Institute of Cancer Research) (PCT Publication No. WO 95/20045; Modjtahedi, et al. (1993) J. Cell. Biophys. 22(I-3): 129-46; Modjtahedi, et al. (1993) Br. J. Cancer 67(2): 247-53; Modjtahedi, et al. (1996) Br. J. Cancer 73(2): 228-35; Modjtahedi, et al. (2003) Int. J. Cancer 105(2): 273-80); TheraCIM hR3 (YM Biosciences, Canada and Centro de Immunologia Molecular, Cuba (U.S. Pat. Nos. 5,891,996; 6,506,883; Mateo, et al. (1997) Immunotechnol. 3(1): 71-81); mAb-806 (Ludwig Institute for Cancer Research, Memorial Sloan-Kettering) (Jungbluth, et al. (2003) Proc. Natl. Acad. Sci. USA. 100(2): 639-44); KSB-102 (KS Biomedix); MR1-1 (IVAX, National Cancer Institute) (PCT Publication No. WO 01/62931A2); and SC100 (Scancell) (PCT Publication No. WO 01/88138); alemtuzumab (Campath®, Millenium), a humanized mAb currently approved for treatment of B-cell chronic lymphocytic leukemia; muromonab-CD3 (Orthoclone OKT3®), an anti-CD3 antibody developed by Ortho Biotech/Johnson & Johnson, ibritumomab tiuxetan (Zevalin®), an anti-CD20 antibody developed by IDEC/Schering AG, gemtuzumab ozogamicin (Mylotarg®), an anti-CD33 (p67 protein) antibody developed by Celltech/Wyeth, alefacept (Amevive®), an anti-LFA-3 Fc fusion developed by Biogen), abciximab (ReoPro®), developed by Centocor/Lilly, basiliximab (Simulect®), developed by Novartis, palivizumab (Synagis®), developed by Medimmune, infliximab (Remicade®), an anti-TNFalpha antibody developed by Centocor, adalimumab (Humira®), an anti-TNFalpha antibody developed by Abbott, Humicade®, an anti-TNFalpha antibody developed by Celltech, golimumab (CNTO-148), a fully human TNF antibody developed by Centocor, etanercept (Enbrel®), an p75 TNF receptor Fc fusion developed by Immunex/Amgen, lenercept, an p55TNF receptor Fc fusion previously developed by Roche, ABX-CBL, an anti-CD147 antibody being developed by Abgenix, ABX-IL8, an anti-IL8 antibody being developed by Abgenix, ABX-MA1, an anti-MUC18 antibody being developed by Abgenix, Pemtumomab (R1549, 90Y-muHMFG1), an anti-MUC1 in development by Antisoma, Therex (R1550), an anti-MUC1 antibody being developed by Antisoma, AngioMab (AS1405), being developed by Antisoma, HuBC-1, being developed by Antisoma, Thioplatin (AS1407) being developed by Antisoma, Antegren® (natalizumab), an anti-alpha-4-beta-1 (VLA-4) and alpha-4-beta-7 antibody being developed by Biogen, VLA-1 mAb, an anti-VLA-1 integrin antibody being developed by Biogen, LTBR mAb, an anti-lymphotoxin beta receptor (LTBR) antibody being developed by Biogen, CAT-152, an anti-TGF-β antibody being developed by Cambridge Antibody Technology, ABT 874 (J695), an anti-IL-12 p40 antibody being developed by Abbott, CAT-192, an anti-TGFβ1 antibody being developed by Cambridge Antibody Technology and Genzyme, CAT-213, an anti-Eotaxin1 antibody being developed by Cambridge Antibody Technology, LymphoStat-B® an anti-Blys antibody being developed by Cambridge Antibody Technology and Human Genome Sciences Inc., TRAIL-R1 mAb, an anti-TRAIL-R1 antibody being developed by Cambridge Antibody Technology and Human Genome Sciences, Inc., Avastin® bevacizumab, rhuMAb-VEGF), an anti-VEGF antibody being developed by Genentech, an anti-HER receptor family antibody being developed by Genentech, Anti-Tissue Factor (ATF), an anti-Tissue Factor antibody being developed by Genentech, Xolair® (Omalizumab), an anti-IgE antibody being developed by Genentech, Raptiva® (Efalizumab), an anti-CD11a antibody being developed by Genentech and Xoma, MLN-02 Antibody (formerly LDP-02), being developed by Genentech and Millenium Pharmaceuticals, HuMax CD4, an anti-CD4 antibody being developed by Genmab, HuMax-IL15, an anti-IL15 antibody being developed by Genmab and Amgen, HuMax-Inflam, being developed by Genmab and Medarex, HuMax-Cancer, an anti-Heparanase I antibody being developed by Genmab and Medarex and Oxford GcoSciences, HuMax-Lymphoma, being developed by Genmab and Amgen, HuMax-TAC, being developed by Genmab, IDEC-131, and anti-CD40L antibody being developed by IDEC Pharmaceuticals, IDEC-151 (Clenoliximab), an anti-CD4 antibody being developed by IDEC Pharmaceuticals, IDEC-114, an anti-CD80 antibody being developed by IDEC Pharmaceuticals, IDEC-152, an anti-CD 23 being developed by IDEC Pharmaceuticals, anti-macrophage migration factor (MIF) antibodies being developed by IDEC Pharmaceuticals, BEC2, an anti-idiotypic antibody being developed by Imclone, IMC-1C11, an anti-KDR antibody being developed by Imclone, DC101, an anti-flk-1 antibody being developed by Imclone, anti-VE cadherin antibodies being developed by Imclone, CEA-Cide® (Iabetuzumab), an anti-carcinoembryonic antigen (CEA) antibody being developed by Immunomedics, LymphoCide® (Epratuzumab), an anti-CD22 antibody being developed by Immunomedics, AFP-Cide, being developed by Immunomedics, MyelomaCide, being developed by Immunomedics, LkoCide, being developed by Immunomedics, ProstaCide, being developed by Immunomedics, MDX-010, an anti-CTLA4 antibody being developed by Medarex, MDX-060, an anti-CD30 antibody being developed by Medarex, MDX-070 being developed by Medarex, MDX-018 being developed by Medarex, Osidem® (IDM-1), and anti-Her2 antibody being developed by Medarex and Immuno-Designed Molecules, HuMax®-CD4, an anti-CD4 antibody being developed by Medarex and Genmab, HuMax-IL15, an anti-IL15 antibody being developed by Medarex and Genmab, CNTO 148, an anti-TNFα antibody being developed by Medarex and Centocor/J&J, CNTO 1275, an anti-cytokine antibody being developed by Centocor/J&J, MOR101 and MOR102, anti-intercellular adhesion molecule-1 (ICAM-1) (CD54) antibodies being developed by MorphoSys, MOR201, an anti-fibroblast growth factor receptor 3 (FGFR-3) antibody being developed by MorphoSys, Nuvion® (visilizumab), an anti-CD3 antibody being developed by Protein Design Labs, HuZAF®, an anti-gamma interferon antibody being developed by Protein Design Labs, Anti-α5β1 Integrin, being developed by Protein Design Labs, anti-IL-12, being developed by Protein Design Labs, ING-1, an anti-EpCAM antibody being developed by Xoma, Xolair® (Omalizumab) a humanized anti-IgE antibody developed by Genentech and Novartis, and MLN01, an anti-Beta2 integrin antibody being developed by Xoma. In another embodiment, the therapeutics include KRN330 (Kirin); huA33 antibody (A33, Ludwig Institute for Cancer Research); CNTO 95 (alpha V integrins, Centocor); MEDI-522 (alpha Vβ3integrin, Medimmune); volociximab (alpha Vβ1 integrin, Biogen/PDL); Human mAb 216 (B cell glycosolated epitope, NCI); BiTE MT103 (bispecific CD19× CD3, Medimmune); 4G7×H22 (Bispecific Bcell×FcgammaR1, Medarex/Merck KGa); rM28 (Bispecific CD28× MAPG, EP Patent No. EP1444268); MDX447 (EMD 82633) (Bispecific CD64×EGFR, Medarex); Catumaxomab (removab) (Bispecific EpCAM×anti-CD3, Trion/Fres); Ertumaxomab (bispecific HER2/CD3, Fresenius Biotech); oregovomab (OvaRex) (CA-125, ViRexx); Rencarex® (WX G250) (carbonic anhydrase IX, Wilex); CNTO 888 (CCL2, Centocor); TRC105 (CD105 (endoglin), Tracon); BMS-663513 (CD137 agonist, Brystol Myers Squibb); MDX-1342 (CD19, Medarex); Siplizumab (MEDI-507) (CD2, Medimmune); Ofatumumab (Humax-CD20) (CD20, Genmab); Rituximab (Rituxan) (CD20, Genentech); veltuzumab (hA20) (CD20, Immunomedics); Epratuzumab (CD22, Amgen); lumiliximab (IDEC 152) (CD23, Biogen); muromonab-CD3 (CD3, Ortho); HuM291 (CD3 fc receptor, PDL Biopharma); HeFi-1, CD30, NCI); MDX-060 (CD30, Medarex); MDX-1401 (CD30, Medarex); SGN-30 (CD30, Seattle Genentics); SGN-33 (Lintuzumab) (CD33, Seattle Genentics); Zanolimumab (HuMax-CD4) (CD4, Genmab); HCD122 (CD40, Novartis); SGN-40 (CD40, Seattle Genentics); Campath1 h (Alemtuzumab) (CD52, Genzyme); MDX-1411 (CD70, Medarex); hLL1 (EPB-1) (CD74.38, Immunomedics); Galiximab (IDEC-144) (CD80, Biogen); MT293 (TRC093/D93) (cleaved collagen, Tracon); HuLuc63 (CS1, PDL Pharma); ipilimumab (MDX-010) (CTLA4, Brystol Myers Squibb); Tremelimumab (Ticilimumab, CP-675,2) (CTLA4, Pfizer); HGS-ETR1 (Mapatumumab) (DR4TRAIL-R1 agonist, Human Genome Science/Glaxo Smith Kline); AMG-655 (DR5, Amgen); Apomab (DR5, Genentech); CS-1008 (DR5, Daiichi Sankyo); HGS-ETR2 (lexatumumab) (DR5TRAIL-R2 agonist, HGS); Cetuximab (Erbitux) (EGFR, Imclone); IMC-11F8, (EGFR, Imclone); Nimotuzumab (EGFR, YM Bio); Panitumumab (Vectabix) (EGFR, Amgen); Zalutumumab (HuMaxEGFr) (EGFR, Genmab); CDX-110 (EGFRvIII, AVANT Immunotherapeutics); adecatumumab (MT201) (Epcam, Merck); edrecolomab (Panorex, 17-1A) (Epcam, Glaxo/Centocor); MORAb-003 (folate receptor a, Morphotech); KW-2871 (ganglioside GD3, Kyowa); MORAb-009 (GP-9, Morphotech); CDX-1307 (MDX-1307) (hCGb, Celldex); Trastuzumab (Herceptin) (HER2, Celldex); Pertuzumab (rhuMAb 2C4) (HER2 (DI), Genentech); apolizumab (HLA-DR beta chain, PDL Pharma); AMG-479 (IGF-1R, Amgen); anti-IGF-1R R1507 (IGF1-R, Roche); CP 751871 (IGF1-R, Pfizer); IMC-A12 (IGF1-R, Imclone); BIIB022 (IGF-1R, Biogen); Mik-beta-1 (IL-2Rb (CD122), Hoffman LaRoche); CNTO 328 (IL6, Centocor); Anti-KIR (1-7F9)

(Killer cell Ig-like Receptor (KIR), Novo); Hu3S193 (Lewis (y), Wyeth, Ludwig Institute of Cancer Research); hCBE-11 (LTOR, Biogen); HuHMFG1 (MUC1, Antisoma/NCl); RAV12 (N-linked carbohydrate epitope, Raven); CAL (parathyroid hormone-related protein (PTH-rP), University of California); CT-011 (PD1, CureTech); MDX-1106 (ono-4538) (PD1, Medarex/Ono); MAb CT-011 (PD1, Curetech); IMC-3G3 (PDGFRa, Imclone); bavituximab (phosphatidylserine, Peregrine); huJ591 (PSMA, Cornell Research Foundation); muJ591 (PSMA, Cornell Research Foundation); GC1008 (TGFb (pan) inhibitor (IgG4), Genzyme); Infliximab (Remicade) (TNFa, Centocor); A27.15 (transferrin receptor, Salk Institute, INSERN WO 2005/111082); E2.3 (transferrin receptor, Salk Institute); Bevacizumab (Avastin) (VEGF, Genentech); HuMV833 (VEGF, Tsukuba Research Lab, PCT Publication No. WO/2000/034337, University of Texas); IMC-18F1 (VEGFR1, Imclone); IMC-1121 (VEGFR2, Imclone).

In certain embodiments, the polypeptides provided herein comprise one modified amino acid at a site-specific position. In certain embodiments, the polypeptides provided herein comprise two modified amino acids at site-specific positions. In certain embodiments, the polypeptides provided herein comprise three modified amino acids at site-specific positions. In certain embodiments, the polypeptides provided herein comprise more than three modified amino acids at site-specific positions.

Antibodies

In certain embodiments, provided herein are antibodies comprising one or more polypeptides that comprise one or more modified amino acids as described herein. In certain embodiments, the antibody is a heterotetramer comprising two identical light (L) chains and two identical heavy (H) chains. Each light chain can be linked to a heavy chain by one covalent disulfide bond. Each heavy chain can be linked to the other heavy chain by one or more covalent disulfide bonds. Each heavy chain and each light chain can also have one or more intrachain disulfide bonds. As is known to those of skill in the art, each heavy chain typically comprises a variable domain ($V_H$) followed by a number of constant domains. Each light chain typically comprises a variable domain at one end ($V_L$) and a constant domain. As is known to those of skill in the art, antibodies typically have selective affinity for their target molecules, i.e. antigens.

The antibodies provided herein can have any polypeptide form known to those of skill in the art. They can be full-length, or fragments. Exemplary full length antibodies include IgA, IgA1, IgA2, IgD, IgE, IgG, IgG1, IgG2, IgG3, IgG4, IgM, etc. Exemplary fragments include Fv, Fab, Fc, sFv, etc.

The one or more modified amino acids can be located at selected site-specific positions in at least one polypeptide chain of an antibody. The polypeptide chain can be any polypeptide chain of the antibody without limitation, including either light chain or either heavy chain. The site-specific position can be in any domain of the antibody, including any variable domain and any constant domain.

The site-specific positions for substituting can be described with any polypeptide nomenclature system known to those of skill in the art. In an embodiment wherein the polypeptide is an antibody, the numbering system can be the Kabat numbering system, wherein the site-specific positions are at heavy chain residues H005, H023, H042, H065, H074, H084, H118, H119, H132, H134, H135, H136, H137, H138, H139, H155, H160, H162, H165, H172, H174, H176, H177, H191, H194, H219, H238, H239, H241, H243, H246, H262, H264, H265, H267, H268, H269, H270, H271, H272, H274, H275, H278, H280, H281, H282, H283, H286, H289, H292, H293, H294, H295, H296, H297, H298, H299, H300, H301, H303, H305, H317, H320, H324, H326, H327, H329, H330, H332, H333, H334, H335, H337, H339, H340, H344, H355, H356, H358, H359, H360, H375, H383, H384, H386, H389, H392, H398, H420, H421, H436, and H438. Specifically, provided herein are antibodies comprising one or more modified amino acids at one or more positions selected from Kabat residues H005, H023, H042, H065, H074, H084, H118, H119, H132, H134, H135, H136, H137, H138, H139, H155, H160, H162, H165, H172, H174, H176, H177, H191, H194, H219, H238, H239, H241, H243, H246, H262, H264, H265, H267, H268, H269, H270, H271, H272, H274, H275, H278, H280, H281, H282, H283, H286, H289, H292, H293, H294, H295, H296, H297, H298, H299, H300, H301, H303, H305, H317, H320, H324, H326, H327, H329, H330, H332, H333, H334, H335, H337, H339, H340, H344, H355, H356, H358, H359, H360, H375, H383, H384, H386, H389, H392, H398, H420, H421, H436, and H438.

In certain embodiments, provided herein are antibodies comprising one or more modified amino acids at one or more positions selected from Kabat residues H005, H023, H074, H084, H118, H119, H132, H134, H135, H136, H137, H139, H160, H162, H165, H172, H191, H194, H239, H241, H246, H267, H268, H269, H270, H271, H272, H274, H275, H280, H281, H282, H283, H286, H289, H292, H293, H294, H295, H296, H297, H298, H299, H300, H301, H303, H305, H317, H320, H324, H326, H327, H329, H330, H332, H333, H334, H335, H337, H339, H340, H344, H355, H359, H375, H386, H389, H392, H398, H420, H421, and H438.

In certain embodiments, provided herein are antibodies comprising one or more modified amino acids at one or more positions selected from Kabat residues H005, H084, H118, H132, H136, H239, H293, H334, H355, H359, and H389.

In certain embodiments, provided herein are antibodies comprising one or more modified amino acids at one or more positions selected from Kabat residues H023, H074, H119, H134, H135, H137, H139, H160, H162, H165, H172, H191, H194, H241, H246, H267, H268, H269, H270, H271, H272, H274, H275, H280, H281, H282, H283, H286, H289, H292, H294, H295, H296, H297, H298, H299, H300, H301, H303, H305, H317, H320, H324, H326, H327, H329, H330, H332, H333, H335, H337, H339, H344, H355, H375, H386, H392, H398, H420, H421, H340 and H438.

In certain embodiments, provided herein are antibodies comprising one or more modified amino acids at one or more positions selected from Kabat residues H042, H065, H138, H155, H174, H176, H177, H219, H238, H243, H262, H264, H265, H278, H356, H358, H360, H383, H384 and H436.

In certain embodiments, provided herein are antibodies comprising one or more modified amino acids at one or more positions selected from Kabat residues corresponding to H292-H301, H303, and H305.

In the Chothia antibody numbering system, these positions are at heavy chain residues H005, H023, H042, H065, H074, H084, H118, H119, H132, H134, H135, H136, H137, H138, H139, H155, H160, H162, H165, H172, H174, H176, H177, H191, H194, H219, H238, H239, H241, H243, H246, H262, H264, H265, H267, H268, H269, H270, H271, H272, H274, H275, H278, H280, H281, H282, H283, H286, H289, H292, H293, H294, H295, H296, H297, H298, H299, H300, H301, H303, H305, H317, H320, H324, H326, H327, H329, H330, H332, H333, H334, H335, H337, H339, H340, H344, H355, H356, H358, H359, H360, H375, H383, H384, H386, H389, H392, H398, H420, H421, H436, and H438. Specifically, provided herein are antibodies comprising one or more modified amino acids at one or more positions selected from Chothia residues H005, H023, H042, H065, H074, H084, H118, H119, H132, H134, H135, H136, H137, H138, H139, H155, H160, H162, H165, H172, H174, H176, H177, H191, H194, H219, H238, H239, H241, H243, H246, H262, H264, H265, H267, H268, H269, H270, H271, H272, H274, H275, H278, H280, H281, H282, H283, H286, H289, H292, H293, H294, H295, H296, H297, H298, H299, H300, H301, H303, H305, H317, H320, H324, H326, H327, H329, H330, H332, H333, H334, H335, H337, H339, H340, H344, H355, H356, H358, H359, H360, H375, H383, H384, H386, H389, H392, H398, H420, H421, H436, and H438.

In certain embodiments, provided herein are antibodies comprising one or more modified amino acids at one or more positions selected from Chothia residues H005, H023, H074, H084, H118, H119, H132, H134, H135, H136, H137, H139, H160, H162, H165, H172, H191, H194, H239, H241, H246, H267, H268, H269, H270, H271, H272, H274, H275, H280, H281, H282, H283, H286, H289, H292, H293, H294, H295, H296, H297, H298, H299, H300, H301, H303, H305, H317, H320, H324, H326, H327, H329, H330, H332, H333, H334, H335, H337, H339, H340, H344, H355, H359, H375, H386, H389, H392, H398, H420, H421, and H438.

In certain embodiments, provided herein are antibodies comprising one or more modified amino acids at one or more positions selected from Chothia residues H005, H084, H118, H132, H136, H239, H293, H334, H355, H359, and H389.

In certain embodiments, provided herein are antibodies comprising one or more modified amino acids at one or more positions selected from Chothia residues corresponding to H292-H301, H303, and H305.

In certain embodiments, provided herein are antibodies comprising one or more modified amino acids at one or more positions selected from Chothia residues H023, H074, H119, H134, H135, H137, H139, H160, H162, H165, H172, H191, H194, H241, H246, H267, H268, H269, H270, H271, H272, H274, H275, H280, H281, H282, H283, H286, H289, H292, H294, H295, H296, H297, H298, H299, H300, H301, H303, H305, H317, H320, H324, H326, H327, H329, H330, H332, H333, H335, H337, H339, H344, H355, H375, H386, H392, H398, H420, H421, H340 and H438.

In certain embodiments, provided herein are antibodies comprising one or more modified amino acids at one or more positions selected from Chothia residues H042, H065, H138, H155, H174, H176, H177, H219, H238, H243, H262, H264, H265, H278, H356, H358, H360, H383, H384 and H436.

In certain embodiments, provided herein are antibodies comprising two or more modified amino acids at at least one or more positions selected from residues L22, L7 and L152, according to the Kabat or Chothia numbering scheme.

In certain embodiments, provided herein are antibodies comprising two or more modified amino acids at at least one or more positions selected from residues L043, L049, L056, L057, L060, L067, L068, L109, L112, L114, L144, L153, L156, L157, L168, L184, L202, L203, and L206, according to the Kabat or Chothia numbering scheme. In certain embodiments, provided herein are antibodies comprising two or more modified amino acids at at least one or more positions selected from residues L043, L049, L056, L057, L060, L067, L068, L109, L112, L114, L144, L153, L156, L168, L184, L202, and L203, according to the Kabat or Chothia numbering scheme. In certain embodiments, provided herein are antibodies comprising two or more modified amino acids at at least one or more positions selected from residues L043, L049, L056, L057, L060, L067, L068, L109, L144, L153, L156, L184, L202, and L203, according to the Kabat or Chothia numbering scheme. In certain embodiments, provided herein are antibodies comprising two or more modified amino acids at at least one or more positions selected from residues L049, L056, L057, L060, L067, L109, L153, L202, and L203, according to the Kabat or Chothia numbering scheme.

In certain embodiments, provided herein are antibodies comprising two or more modified amino acids at at least one or more positions selected from residues (−)L001, L003, L005, L007, L008, L009, L010, L016, L017, L018, L020, L022, L026, L027, L045, L058, L063, L065, L066, L070, L077, L079, L107, L138, L142, L143, L152, L171, L182, L188, L199, and L201, according to the Kabat or Chothia numbering scheme. In certain embodiments, provided herein are antibodies comprising two or more modified amino acids at at least one or more positions selected from residues minus 1, L003, L005, L007, L008, L009, L010, L016, L017, L018, L020, L022, L026, L027, L045, L058, L063, L065, L066, L070, L077, L079, L107, L142, L143, L152, L171, L182, L188, L199, and L201, according to the Kabat or Chothia numbering scheme. In certain embodiments, provided herein are antibodies comprising two or more modified amino acids at at least one or more positions selected from residues (−)L001, L003, L005, L007, L008, L009, L016, L017, L018, L020, L022, L026, L027, L045, L058, L063, L065, L066, L070, L077, L079, L107, L142, L152, L171, L182, L188, and L199, according to the Kabat or Chothia numbering scheme. In certain embodiments, provided herein are antibodies comprising two or more modified amino acids at at least one or more positions selected from residues minus 1, L005, L007, L008, L016, L017, L018, L020, L022, L027, L045, L058, L063, L077, L079, L107, L142, L152, L182, L188, and L199, according to the Kabat or Chothia numbering scheme. In certain embodiments, provided herein are antibodies comprising two or more modified amino acids at at least one or more positions selected from residues (−)L001, L016, L063, and L199, according to the Kabat or Chothia numbering scheme.

In certain embodiments, provided herein are antibodies comprising two or more modified amino acids at at least one or more positions selected from residues (−)L001, L007, L008, L016, L022, L063, L014, L070, L138, L142, L143 and L152, according to the Kabat or Chothia numbering scheme.

In certain embodiments, provided herein are antibodies comprising two or more modified amino acids at at least one or more positions selected from residues (−)L001, L007, L008, L016, L022, L063, L070, L138, L142, L143, L152 and L201, according to the Kabat or Chothia numbering scheme.

In certain embodiments, provided herein are antibodies comprising two or more modified amino acids at at least one or more positions selected from those corresponding to 22, 7 and 152 of the representative light chain polypeptide according to SEQ ID NO:2.

In certain embodiments, provided herein are antibodies comprising two or more modified amino acids at at least one or more positions selected from those corresponding to minus 1, 3, 5, 7, 8, 9, 10, 16, 17, 18, 20, 22, 26, 27, 45, 58, 63, 65, 66, 70, 77, 79, 107, 138, 142, 143, 152, 171, 182, 188, 199, and 201 of the representative light chain polypeptide according to SEQ ID NO:2.

In certain embodiments, provided herein are antibodies comprising two or more modified amino acids at at least one or more positions selected from those corresponding to minus 1, 3, 5, 7, 8, 9, 16, 17, 18, 20, 22, 26, 27, 45, 58, 63, 65, 66, 70, 77, 79, 107, 142, 143, 152, 171, 182, 188, 199, and 201 of the representative light chain polypeptide according to SEQ ID NO:2.

In certain embodiments, provided herein are antibodies comprising two or more modified amino acids at at least one or more positions selected from those corresponding to minus 1, 3, 5, 7, 8, 9, 16, 17, 18, 20, 22, 26, 27, 45, 58, 63, 65, 66, 70, 77, 79, 107, 142, 152, 171, 182, 188, and 199 of the representative light chain polypeptide according to SEQ ID NO:2.

In certain embodiments, provided herein are antibodies comprising two or more modified amino acids at at least one or more positions selected from those corresponding to minus 1, 5, 7, 8, 16, 17, 18, 20, 22, 27, 45, 58, 63, 77, 79, 107, 142, 152, 182, 188, and 199 of the representative light chain polypeptide according to SEQ ID NO:2.

In certain embodiments, provided herein are antibodies comprising two or more modified amino acids at at least one or more positions selected from those corresponding to minus 1, 16, 63, and 199 of the representative light chain polypeptide according to SEQ ID NO:2.

In certain embodiments, provided herein are antibodies comprising two or more modified amino acids at at least one or more positions selected from those corresponding to minus 1, 7, 8, 16, 22, 63, 14, 70, 138, 142, 143 and 152 of the representative light chain polypeptide according to SEQ ID NO:2.

In certain embodiments, provided herein are antibodies comprising two or more modified amino acids at at least one or more positions selected from those corresponding to minus 1, 7, 8, 16, 22, 63, 70, 138, 142, 143, 152, and 201 of the representative light chain polypeptide according to SEQ ID NO:2.

In certain embodiments, provided herein are antibodies comprising two or more modified amino acids at at least one or more positions selected from those corresponding to 43, 49, 56, 57, 60, 67, 68, 109, 112, 114, 144, 153, 156, 157, 168, 184, 202, 203, and 206 of the representative light chain polypeptide according to SEQ ID NO:2.

In certain embodiments, provided herein are antibodies comprising two or more modified amino acids at at least one or more positions selected from those corresponding to 43, 49, 56, 57, 60, 67, 68, 109, 112, 144, 153, 156, 168, 184, 202, and 203 of the representative light chain polypeptide according to SEQ ID NO:2.

In certain embodiments, provided herein are antibodies comprising two or more modified amino acids at at least one or more positions selected from those corresponding to 43, 49, 56, 57, 60, 67, 68, 109, 144, 153, 156, 184, 202, and 203 of the representative light chain polypeptide according to SEQ ID NO:2.

In certain embodiments, provided herein are antibodies comprising two or more modified amino acids at at least one or more positions selected from those corresponding to 49, 56, 57, 60, 67, 109, 153, 202, and 203 of the representative light chain polypeptide according to SEQ ID NO:2.

In other words, provided herein are antibodies comprising two or more modified amino acids at at least one or more positions selected from those corresponding to 407, 124, 183, 139, 25, 40, 119, 193, 225, 19, 52, 71, 117 or 224 of the representative heavy chain polypeptide according to SEQ ID NO:1 and at at least one or more positions selected from those corresponding to 22, 7 and 152 of the representative light chain polypeptide according to SEQ ID NO:2.

The site-specific positions can also be identified relative to the amino acid sequences of the polypeptide chains of a reference antibody. For example, the amino acid sequence of a reference heavy chain is provided at SEQ ID NO:1. In the reference heavy chain, the site-specific positions are at residues 5, 23, 42, 66, 75, 88, 121, 122, 135, 137, 138, 139, 140, 141, 142, 158, 163, 165, 168, 175, 177, 179, 180, 194, 197, 222, 241, 242, 244, 246, 249, 265, 267, 268, 270, 271, 272, 273, 274, 275, 277, 278, 281, 283, 284, 285, 286, 289, 292, 295, 296, 297, 298, 299, 300, 301, 302, 303, 304, 306, 308, 320, 323, 327, 329, 330, 332, 333, 335, 336, 337, 338, 340, 342, 343, 347, 358, 359, 361, 362, 363, 378, 386, 387, 389, 392, 395, 401, 423, 424, 439 and 441. Specifically, provided herein are antibodies comprising one or more modified amino acids at one or more positions selected from those corresponding to 5, 23, 42, 66, 75, 88, 121, 122, 135, 137, 138, 139, 140, 141, 142, 158, 163, 165, 168, 175, 177, 179, 180, 194, 197, 222, 241, 242, 244, 246, 249, 265, 267, 268, 270, 271, 272, 273, 274, 275, 277, 278, 281, 283, 284, 285, 286, 289, 292, 295, 296, 297, 298, 299, 300, 301, 302, 303, 304, 306, 308, 320, 323, 327, 329, 330, 332, 333, 335, 336, 337, 338, 340, 342, 343, 347, 358, 359, 361, 362, 363, 378, 386, 387, 389, 392, 395, 401, 423, 424, 439 and 441 of the representative heavy chain antibody according to SEQ ID NO:1.

In certain embodiments, provided herein are antibodies comprising one or more modified amino acids at one or more positions selected from those corresponding to 5, 23, 75, 88, 121, 122, 135, 137, 138, 139, 140, 142, 163, 165, 168, 175, 194, 197, 242, 244, 249, 270, 271, 272, 273, 274, 275, 277, 278, 283, 284, 285, 286, 289, 292, 295, 296, 297, 298, 299, 300, 301, 302, 303, 304, 306, 308, 320, 323, 327, 329, 330, 332, 333, 335, 336, 337, 338, 340, 342, 343, 347, 358, 362, 378, 389, 392, 395, 401, 423, 424, and 441 of the representative heavy chain antibody according to SEQ ID NO:1.

In certain embodiments, provided herein are antibodies comprising one or more modified amino acids at one or more positions selected from those corresponding to 5, 88, 121, 135, 139, 242, 296, 337, 358, 362, and 392 of the representative heavy chain antibody according to SEQ ID NO:1.

In certain embodiments, provided herein are antibodies comprising one or more modified amino acids at one or more positions selected from those corresponding to 23, 75, 122, 137, 138, 140, 142, 163, 165, 168, 175, 194, 197, 244, 249, 270, 271, 272, 273, 274, 275, 277, 278, 283, 284, 285, 286, 289, 292, 295, 297, 298, 299, 300, 301, 302, 303, 304, 306, 308, 320, 323, 327, 329, 330, 332, 333, 335, 336, 338, 340, 342, 343, 347, 358, 378, 389, 395, 401, 423, 424, and 441 of the representative heavy chain antibody according to SEQ ID NO:1.

In certain embodiments, provided herein are antibodies comprising one or more modified amino acids at one or more positions selected from those corresponding to 42, 66, 141, 158, 177, 179, 180, 222, 241, 246, 265, 267, 268, 281, 359, 361, 363, 386, 387 and 439 of the representative heavy chain antibody according to SEQ ID NO:1.

In certain embodiments, provided herein are antibodies comprising one or more modified amino acids at one or more positions selected from those corresponding to 292-301, 303, and 305 of the representative heavy chain antibody according to SEQ ID NO:1.

In certain embodiments, provided herein are antibodies comprising one or more modified amino acids at one or more positions selected from heavy chain or light chain residues H404, H121, H180, H241, L22, L7, L152, H136, H25, H40, H119, H190, H222, H19, H52, or H70 according to the Kabat or Chothia numbering scheme.

In certain embodiments, provided herein are antibodies comprising one or more modified amino acids at one or more positions selected from heavy chain or light chain residues H404, H121, H180, H241, L22, L7, L152, H136, H25, H40, H119, H190, and H222 according to the Kabat or Chothia numbering scheme.

In certain embodiments, provided herein are antibodies comprising one or more modified amino acids at one or more positions selected from heavy chain or light chain residues H404, H121, H180, H241, L22, L7, L152, and H136 according to the Kabat or Chothia numbering scheme.

In certain embodiments, provided herein are antibodies comprising a polypeptide chain having at least 70%, 80% or 90% homology to SEQ ID NO:1 and having one or more modified amino acids at sites selected from sites corresponding to residues 404, 121, 180, 241, 136, 25, 40, 119, 190, 222, 19, 52, or 70 of the representative heavy chain polypeptide according to SEQ ID NO:1.

In certain embodiments, provided herein are antibodies comprising a polypeptide chain having at least 70%, 80% or 90% homology to SEQ ID NO:2 and having one or more modified amino acids at sites selected from sites corresponding to residues 22, 7 and 152 of the representative light chain polypeptide according to SEQ ID NO:2.

In certain embodiments, provided herein are antibodies comprising two or more site-specific modified amino acids. In certain embodiments, each modified amino acid is independently at a specific site selected from the group consisting of optimally substitutable positions of any polypeptide chain of the antibody.

In certain embodiments, the antibodies comprise two or more site-specific modified amino acids in a single light chain polypeptide. In certain embodiments, the antibodies comprise two or more site-specific modified amino acids in a single heavy chain polypeptide. In certain embodiments, the antibodies comprise at least one site-specific modified amino acid in a light chain polypeptide and at least one site-specific modified amino acid in a heavy chain polypeptide.

In certain embodiments, the antibodies comprise at least one site-specific modified amino acid in a light chain polypeptide and at least one site-specific modified amino acid in each of two heavy chain polypeptides. In certain embodiments, the antibodies comprise at least one site-specific modified amino acid in each of two light chain polypeptides and at least one site-specific modified amino acid in a heavy chain polypeptide. In certain embodiments, the antibodies comprise at least one site-specific modified amino acid in each of two light chain polypeptides and at least one site-specific modified amino acid in each of two heavy chain polypeptides.

In certain embodiments, the antibodies comprise three or more, four or more, five or more or six or more site-specific modified amino acids. In certain embodiments, the antibodies comprise two to six modified amino acids.

The site-specific positions for substituting can be described with any antibody nomenclature system known to those of skill in the art. In the Kabat numbering system, these positions are at heavy chain or light chain residues H404, H121, H180, L22, L7, L152, H136, H25, H40, H119, H190, H222, H19, H52, H70, H110, and H221. In other words, provided herein are antibodies comprising two or more modified amino acids at at least one or more positions selected from Kabat residues H404, H121, H180, L22, L7, L152, H136, H25, H40, H119, H190, H222, H19, H52, H70, H110, and H221.

In some embodiments, provided herein are antibodies comprising two or more modified amino acids at at least one or more positions selected from Kabat residues H404, H121, H180, H136, H25, H40, H119, H190, H222, H19, H52, H70, H110, and H221.

In certain embodiments, provided herein are antibodies comprising two or more modified amino acids at at least one or more positions selected from residues L22, L7 and L152, according to the Kabat or Chothia numbering scheme.

In certain embodiments, provided herein are antibodies comprising two or more site-specific modified amino acids at sequence positions corresponding to residues selected from heavy chain or light chain residues H404, H121, H180, L22, L7, L152, H136, H25, H40, H119, H190, H222, H19, H52, H70, H110, or H221 according to the Kabat or Chothia numbering scheme.

In certain embodiments, provided herein are antibodies comprising two or more site-specific modified amino acids at sequence positions corresponding to residues selected from residues 407, 124, 183, 139, 25, 40, 119, 193, 225, 19, 52, 71, 117 or 224 of the representative heavy chain polypeptide according to SEQ ID NO:1.

In certain embodiments, provided herein are antibodies comprising two or more site-specific modified amino acids at sequence positions corresponding to residues selected from residues 22, 7 or 152 of the representative light chain polypeptide according to SEQ ID NO:2.

The antibody can have any antibody form recognized by those of skill in the art. The antibody can comprise a single polypeptide chain—a single heavy chain or a single light chain. The antibody can also form multimers that will be recognized by those of skill in the art including homodimers, heterodimers, homomultimers, and heteromultimers. These multimers can be linked or unlinked. Useful linkages include interchain disulfide bonds typical for polypeptide molecules. The multimers can also be linked by other amino acids, including the modified amino acids described herein. The antibody can be an immunoglobulin such as of any class or subclass including IgA, IgA1, IgA2, IgD, IgE, IgG, IgG1, IgG2, IgG3, IgG4 and IgM. The antibody can be of the form of any antibody fragment including Fv, Fc, Fab, and (Fab')$_2$ and scFv.

A parent antibody can have affinity to any antigen known to those of skill in the art, or later discovered. Virtually any substance may be an antigen for a parent antibody, or an antibody of the present description. Examples of useful antigens include, but are not limited to, Alpha-1 antitrypsin, Angiostatin, Antihemolytic factor, polypeptides, Apolipoprotein, Apoprotein, Atrial natriuretic factor, Atrial natriuretic polypeptide, Atrial peptides, C-X-C chemokines (e.g., T39765, NAP-2, ENA-78, Gro-a, Gro-b, Gro-c, IP-10, GCP-2, NAP-4, SDF-1, PF4, MIG), calcitonin, CC chemokines (e.g., monocyte chemoattractant protein-1, monocyte chemoattractant protein-2, monocyte chemoattractant protein-3, monocyte inflammatory protein-1 alpha, monocyte inflammatory protein-1 beta, RANTES, 1309, R83915, R91733, HCC1, T58847, D31065, T64262), CD40 ligand, C-kit ligand, collagen, colony stimulating factor (CSF), complement factor 5a, complement inhibitor, complement receptor 1, cytokines, (e.g., epithelial neutrophil activating peptide-78, GRO/MGSA, GRO, GRO, MIP-1, MIP-1, MCP-1), epidermal growth factor (EGF), erythropoietin ("EPO"), exfoliating toxins A and B, factor IX, factor VII, factor VIII, factor X, fibroblast growth factor (FGF), fibrinogen, fibronectin, G-CSF, GM-CSF, glucocerebrosidase, gonadotropin, growth factors, hedgehog proteins (e.g., Sonic, Indian, Desert), hemoglobin, hepatocyte growth factor (HGF), hirudin, human serum albumin, insulin, insulin-like growth factor (IGF), interferons (e.g., IFN-α, IFN-, IFN-γ), interleukins (e.g., IL-1, IL-2, IL-3, IL-4, IL-5, IL-6, IL-7, IL-8, IL-9, IL-10, IL-11, IL-12, etc.), keratinocyte growth factor (KGF), lactoferrin, leukemia inhibitory factor, luciferase, neurturin, neutrophil inhibitory factor (NIF), oncostatin M, osteogenic protein, parathyroid hormone, PD-ECSF, PDGF, peptide hormones (e.g., human growth hormone), pleiotropin, protein A, protein G, pyrogenic exotoxins A, B, and C, relaxin, renin, SCF, soluble complement receptor I, soluble I-CAM 1, soluble interleukin receptors (IL-1, 2, 3, 4, 5, 6, 7, 9, 10, 11, 12, 13, 14, 15), soluble TNF receptor, somatomedin, somatostatin, somatotropin, streptokinase, superantigens, i.e., staphylococcal enterotoxins (SEA, SEB, SEC1, SEC2, SEC3, SED, SEE), superoxide dismutase, toxic shock syndrome toxin (TSST-1), thymosin alpha 1, tissue plasminogen activator, tumor necrosis factor (TNF beta), tumor necrosis factor receptor (TNFR), tumor necrosis factor-alpha (TNF alpha), vascular endothelial growth factor (VEGF), urokinase and others. These antigens can be obtained by methods known to those of skill in the art, for example, from commercial sources or from published polypeptide or polynucleotide sequences (e.g. Genbank).

Additional antigens include, but are not limited to, transcriptional and expression activators. Exemplary transcriptional and expression activators include genes and proteins that modulate cell growth, differentiation, regulation, or the like. Expression and transcriptional activators are found in prokaryotes, viruses, and eukaryotes, including fungi, plants, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA. Antigens include, but are not limited to, expression activators such as cytokines, inflammatory molecules, growth factors, their receptors, and oncogene products, e.g., interleukins (e.g., IL-1, IL-2, IL-8, etc.), interferons, FGF, IGF-I, IGF-II, FGF, PDGF, TNF, TGF-α, TGF-β, EGF, KGF, SCF/c-Kit, CD40L/CD40, VLA-4VCAM-1, ICAM-1/LFA-1, and hyalurin/CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors such as those for estrogen, progesterone, testosterone, aldosterone, the LDL receptor ligand and corticosterone.

Vaccine proteins may be antigens including, but not limited to, proteins from infectious fungi, e.g., *Aspergillus*, *Candida* species; bacteria, particularly *E. coli*, which serves a model for pathogenic bacteria, as well as medically important bacteria such as Staphylococci (e.g., *aureus*), or Streptococci (e.g., *pneumoniae*); protozoa such as sporozoa (e.g., Plasmodia), rhizopods (e.g., *Entamoeba*) and flagellates (*Trypanosoma, Leishmania, Trichomonas, Giardia*, etc.); viruses such as (+) RNA viruses (examples include Poxviruses e.g., vaccinia; Picornaviruses, e.g. polio; Togaviruses, e.g., rubella; Flaviviruses, e.g., HCV; and Coronaviruses), (−) RNA viruses (e.g., Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B.

Antigens may be enzymes including, but not limited to, amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases.

Agriculturally related proteins such as insect resistance proteins (e.g., the Cry proteins), starch and lipid production enzymes, plant and insect toxins, toxin-resistance proteins, Mycotoxin detoxification proteins, plant growth enzymes (e.g., Ribulose 1,5-Bisphosphate Carboxylase/Oxygenase, "RUBISCO"), lipoxygenase (LOX), and Phosphoenolpyruvate (PEP) carboxylase may also be antigens.

For example, the antigen may be a disease-associated molecule, such as tumor surface antigen such as B-cell idiotypes, CD20 on malignant B cells, CD33 on leukemic blasts, and HER2/neu on breast cancer. Alternatively, the antigen may be a growth factor receptor. Examples of the growth factors include, but are not limited to, epidermal growth factors (EGFs), transferrin, insulin-like growth factor, transforming growth factors (TGFs), interleukin-1, and interleukin-2. For example, a high expression of EGF receptors has been found in a wide variety of human epithelial primary tumors. TGF-α has been found to mediate an autocrine stimulation pathway in cancer cells. Several murine monoclonal antibodies have been demonstrated to be able to bind EGF receptors, block the binding of ligand to EGF receptors, and inhibit proliferation of a variety of human cancer cell lines in culture and in xenograft models. Mendelsohn and Baselga (1995) Antibodies to growth factors and receptors, in Biologic Therapy of Cancer, 2nd Ed., J B Lippincott, Philadelphia, pp 607-623. Thus, antibodies may be used to treat a variety of cancers.

The antigen may also be cell surface protein or receptor associated with coronary artery disease such as platelet glycoprotein IIb/IIIa receptor, autoimmune diseases such as CD4, CAMPATH-1 and lipid A region of the gram-negative bacterial lipopolysaccharide. Humanized antibodies against CD4 have been tested in clinical trials in the treatment of patients with mycosis fungoides, generalized postular psoriasis, severe psoriasis, and rheumatoid arthritis. Antibodies against lipid A region of the gram-negative bacterial lipopolysaccharide have been tested clinically in the treatment of septic shock. Antibodies against CAMPATH-1 have also been tested clinically in the treatment of against refractory rheumatoid arthritis. Thus, antibodies provided herein may be used to treat a variety of autoimmune diseases.

Useful antigens also include proteins or peptides associated with human allergic diseases, such as inflammatory mediator proteins, e.g. interleukin-1 (IL-1), tumor necrosis factor (TNF), leukotriene receptor and 5-lipoxygenase, and adhesion molecules such as V-CAM/VLA-4. In addition, IgE may also serve as the antigen because IgE plays pivotal role in type I immediate hypersensitive allergic reactions such as asthma. Studies have shown that the level of total serum IgE tends to correlate with severity of diseases, especially in asthma. Burrows et al. (1989) "Association of asthma with serum IgE levels and skin-test reactivity to allergens" New Engl. L. Med. 320:271-277. Thus, antibodies selected against IgE may be used to reduce the level of IgE or block the binding of IgE to mast cells and basophils in the treatment of allergic diseases without having substantial impact on normal immune functions.

The antigen may also be a viral surface or core protein which may serve as an antigen to trigger immune response of the host. Examples of these viral proteins include, but are not limited to, glycoproteins (or surface antigens, e.g., GP120 and GP41) and capsid proteins (or structural proteins, e.g., P24 protein); surface antigens or core proteins of hepatitis A, B, C, D or E virus (e.g. small hepatitis B surface antigen (SHBsAg) of hepatitis B virus and the core proteins of hepatitis C virus, NS3, NS4 and NS5 antigens); glycoprotein (G-protein) or the fusion protein (F-protein) of respiratory syncytial virus (RSV); surface and core proteins of herpes simplex virus HSV-1 and HSV-2 (e.g., glycoprotein D from HSV-2).

The antigen may also be a mutated tumor suppressor gene product that has lost its tumor-suppressing function and may render the cells more susceptible to cancer. Tumor suppressor genes are genes that function to inhibit the cell growth and division cycles, thus preventing the development of neoplasia. Mutations in tumor suppressor genes cause the cell to ignore one or more of the components of the network of inhibitory signals, overcoming the cell cycle check points and resulting in a higher rate of controlled cell growth-cancer. Examples of the tumor suppressor genes include, but are not limited to, DPC-4, NF-1, NF-2, RB, p53, WT1, BRCA1 and BRCA2. DPC-4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. p53 codes for p53 protein that regulates cell division and can induce apoptosis. Mutation and/or inaction of p53 is found in a wide ranges of cancers. WT1 is involved in Wilms tumor of the kidneys. BRCA1 is involved in breast and ovarian cancer, and BRCA2 is involved in breast cancer. Thus, antibodies may be used to block the interactions of the gene product with other proteins or biochemicals in the pathways of tumor onset and development.

The antigen may be a CD molecule including but not limited to, CD1a, CD1b, CD1c, CD1d, CD2, CD3γ, CD3δ, CD3ε, CD4, CD5, CD6, CD7, CD8α, CD8β, CD9, CD10, CD11a, CD11b, CD11c, CDw12, CD13, CD14, CD15, CD15s, CD16a, CD16b, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD45, CD45R, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L, CD62P, CD63, CD64, CD65, CD66a, CD66b, CD66c, CD66d, CD66e, CD66f, CD67, CD68, CD69, CDw70, CD71, CD72, CD73, CD74, CDw75, CDw76, CD77, CD79u, CD790, CD80, CD81, CD82, CD83, CD84, CD85, CD86, CD87, CD88, CD89, CD90, CD91, CDw92, CD93, CD94, CD95, CD96, CD97, CD98, CD99, CD100, CD101, CD102, CD103, CD104, CD105, CD106, CD107a, CD107b, CDw108, CDw109, CD110-113, CD114, CD115, CD116, CD117, CD118, CD119, CD120a, CD120b, CD121a, CD121b, CD122, CD123, CDw124, CD125, CD126, CDw127, CDw128a, CDw128b, CD129, CDw130, CD131, CD132, CD133, CD134, CD135, CD136, CD137, CD138, CD139, CD140a, CD140b, CD141, CD142, CD143, CD144, CDw145, CD146, CD147, CD148, CDw149, CD150, CD151, CD152, CD153, CD154, CD155, CD156, CD157, CD158a, CD158b, CD161, CD162, CD163, CD164, CD165, CD166, and TCRδ The antigen may be VEGF, VEGF receptor, EGFR, Her2, TNFa, TNFRI receptor, GPIIb/IIIa, IL-2R alpha chain, IL-2R beta chain, RSV F protein, alpha4 integrin, IgE, IgE receptor, digoxin, carpet viper venom, complement C5, OPGL, CA-125 tumor antigen, Staphylococci proteins, *Staphylococcus epidermidis* proteins, *Staphylococcus aureus* proteins, proteins involved Staphylococcal infection (including but not limited to, *Staphylococcus aureus* and *Staphylococcus epidermidis*), IL-6 receptor, CTLA-4, RSV, Tac subunit of IL-2 receptor, IL-5, and EpCam. The antigen may be a fragment of a molecule.

Examples of useful bispecific parent antibodies include, but are not limited to, those with one antibody directed against a tumor cell antigen and the other antibody directed against a cytotoxic trigger molecule such as anti-FcγRI/anti-CD 15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell adhesion molecule (NCAM)/anti-CD3, anti-folate binding protein (FBP)/anti-CD3, anti-pan carcinoma associated antigen (AMOC-31)/anti-CD3; bispecific antibodies with one antibody which binds specifically to a tumor antigen and another antibody which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α (IFN-α)/anti-hybridoma idiotype, anti-CEA/anti-vinca alkaloid; bispecific antibodies for converting enzyme activated prodrugs such as anti-CD30/anti-alkaline phosphatase (which catalyzes conversion of mitomycin phosphate prodrug to mitomycin alcohol); bispecific antibodies which can be used as fibrinolytic agents such as anti-fibrin/anti-tissue plasminogen activator (tPA), anti-fibrin/anti-urokinase-type plasminogen activator (uPA); bispecific antibodies for targeting immune complexes to cell surface receptors such as anti-low density lipoprotein (LDL)/anti-Fc receptor (e.g. FcγRI, FcγRII or FcγRIII); bispecific antibodies for use in therapy of infectious diseases such as anti-CD3/anti-herpes simplex virus (HSV), anti-T-cell receptor: CD3 complex/anti-influenza, anti-FcγR/anti-HIV; bispecific antibodies for tumor detection in vitro or in vivo such as anti-CEA/anti-EOTUBE, anti-CEA/anti-DPTA, anti-anti-p185H$^{ER2}$/anti-hapten; bispecific antibodies as vaccine adjuvants (see Fanger, M W et al., Crit Rev Immunol. 1992; 12(34):101-24, which is incorporated by reference herein); and bispecific antibodies as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-β-galactosidase (see Nolan, O et R. O'Kennedy, Biochim Biophys Acta. 1990 Aug. 1; 1040 (1):1-11, which is incorporated by reference herein). Examples of trispecific antibodies include anti-CD3/anti-CD4/anti-CD37, anti-CD3/anti-CD5/anti-CD37 and anti-CD3/anti-CD8/anti-CD37.

Linkers and Payloads

In certain embodiments, the polypeptide comprises a modified amino acid having a reactive group, as described herein. One of skill in the art can use the reactive group to link the polypeptide to any molecular entity capable of forming a covalent bond to the modified amino acid, directly or indirectly via a linker. Thus, provided herein are conjugates comprising a polypeptide comprising an amino acid residue corresponding to a compound of formula I, Ia, II, 1-30 or 40 linked to a payload and optionally comprising a linking moiety between the polypeptide and the payload.

Useful linkers include those described herein. In certain embodiments, the linker is any divalent or multivalent linker known to those of skill in the art. Generally, the linker is capable of forming covalent bonds to the functional moiety and the alpha carbon of the modified amino acid. Useful divalent linkers include a bond, alkylene, substituted alkylene, heteroalkylene, substituted heteroalkylene, arylene, substituted arylene, heteroarlyene and substituted heteroarylene. In certain embodiments, the linker is $C_{1-10}$ alkylene or $C_{1-10}$ heteroalkylene.

The molecular payload can be any molecular entity that one of skill in the art might desire to conjugate to the polypeptide. In certain embodiments, the payload is a therapeutic moiety. In such embodiment, the polypeptide conjugate can be used to target the therapeutic moiety to its molecular target. In certain embodiments, the payload is a labeling moiety. In such embodiments, the polypeptide conjugate can be used to detect binding of the polypeptide to its target. In certain embodiments, the payload is a cytotoxic moiety. In such embodiments, the conjugate can be used target the cytotoxic moiety to a diseased cell, for example a cancer cell, to initiate destruction or elimination of the cell. Conjugates comprising other molecular payloads apparent to those of skill in the art are within the scope of the conjugates described herein.

In certain embodiments, a conjugate can have a payload selected from the group consisting of a label, a dye, a polymer, a water-soluble polymer, polyethylene glycol, a derivative of polyethylene glycol, a photocrosslinker, a cytotoxic compound, a radionuclide, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a peptide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, or any combination thereof. In an embodiment, the payload is a label, a dye, a polymer, a cytotoxic compound, a radionuclide, a drug, an affinity label, a resin, a protein, a polypeptide, a polypeptide analog, an antibody, antibody fragment, a metal chelator, a cofactor, a fatty acid, a carbohydrate, a polynucleotide, a DNA, a RNA, a peptide, a fluorophore, or a carbon-linked sugar. In another embodiment, the payload is a label, a dye, a polymer, a drug, an antibody, antibody fragment, a DNA, a RNA, or a peptide.

Useful drug payloads include any cytotoxic, cytostatic or immunomodulatory agent. Useful classes of cytotoxic or immunomodulatory agents include, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, calmodulin inhibitors, chemotherapy sensitizers, duocarmycins, etoposides, fluorinated pyrimidines, ionophores, lexitropsins, maytansinoids, nitrosoureas, platinols, pore-forming compounds, purine antimetabolites, puromycins, radiation sensitizers, rapamycins, steroids, taxanes, topoisomerase inhibitors, vinca alkaloids, or the like.

Individual cytotoxic or immunomodulatory agents include, for example, an androgen, anthramycin (AMC), asparaginase, 5-azacytidine, azathioprine, bleomycin, busulfan, buthionine sulfoximine, calicheamicin, calicheamicin derivatives, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (formerly actinomycin), daunorubicin, decarbazine, DM1, DM4, docetaxel, doxorubicin, etoposide, an estrogen, 5-fluordeoxyuridine, 5-fluorouracil, gemcitabine, gramicidin D, hydroxyurea, idarubicin, ifosfamide, irinotecan, lomustine (CCNU), maytansine, mechlorethamine, melphalan, 6-mercaptopurine, methotrexate, mithramycin, mitomycin C, mitoxantrone, nitroimidazole, paclitaxel, palytoxin, plicamycin, procarbizine, rhizoxin, streptozotocin, tenoposide, 6-thioguanine, thioTEPA, topotecan, vinblastine, vincristine, vinorelbine, VP-16 and VM-26.

In some embodiments, suitable cytotoxic agents include, for example, DNA minor groove binders (e.g., enediynes and lexitropsins, a CBI compound; see also U.S. Pat. No. 6,130,237), duocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophycins, cemadotin, maytansinoids, discodermolide, eleutherobin, and mitoxantrone.

In some embodiments, the payload is an anti-tubulin agent. Examples of anti-tubulin agents include, but are not limited to, taxanes (e.g., Taxol® (paclitaxel), Taxotere® (docetaxel)), T67 (Tularik) and vinca alkyloids (e.g., vincristine, vinblastine, vindesine, and vinorelbine). Other antitubulin agents include, for example, baccatin derivatives, taxane analogs, epothilones (e.g., epothilone A and B), nocodazole, colchicine and colcimid, estramustine, cryptophycins, cemadotin, maytansinoids, combretastatins, discodermolide, and eleutherobin.

In certain embodiments, the cytotoxic agent is a maytansinoid, another group of anti-tubulin agents. For example, in specific embodiments, the maytansinoid can be maytansine or DM-1 (ImmunoGen, Inc.; see also Chari et al., 1992, Cancer Res. 52:127-131).

In some embodiments, the payload is an auristatin, such as auristatin E or a derivative thereof. For example, the auristatin E derivative can be an ester formed between auristatin E and a keto acid. For example, auristatin E can be reacted with paraacetyl benzoic acid or benzoylvaleric acid to produce AEB and AEVB, respectively. Other typical auristatin derivatives include AFP, MMAF, and MMAE. The synthesis and structure of auristatin derivatives are described in U.S. Patent Application Publication Nos. 2003-0083263, 2005-0238649 and 2005-0009751; International Patent Publication No. WO 04/010957, International Patent Publication No. WO 02/088172, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284;

5,504,191; 5,410,024; 5,138,036; 5,076,973; 4,986,988; 4,978,744; 4,879,278; 4,816,444; and 4,486,414.

In some embodiments, the payload is not a radioisotope. In some embodiments, the payload is not radioactive.

In some embodiments, the payload is an antimetabolite. The antimetabolite can be, for example, a purine antagonist (e.g., azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscarnet, or trifluridine.

In other embodiments, the payload is tacrolimus, cyclosporine, FU506 or rapamycin. In further embodiments, the Drug is aldesleukin, alemtuzumab, alitretinoin, allopurinol, altretamine, amifostine, anastrozole, arsenic trioxide, bexarotene, bexarotene, calusterone, capecitabine, celecoxib, cladribine, Darbepoetin alfa, Denileukin diftitox, dexrazoxane, dromostanolone propionate, epirubicin, Epoetin alfa, estramustine, exemestane, Filgrastim, floxuridine, fludarabine, fulvestrant, gemcitabine, gemtuzumab ozogamicin (MYLOTARG), goserelin, idarubicin, ifosfamide, imatinib mesylate, Interferon alfa-2a, irinotecan, letrozole, leucovorin, levamisole, meclorethamine or nitrogen mustard, megestrol, mesna, methotrexate, methoxsalen, mitomycin C, mitotane, nandrolone phenpropionate, oprelvekin, oxaliplatin, pamidronate, pegademase, pegaspargase, pegfilgrastim, pentostatin, pipobroman, plicamycin, porfimer sodium, procarbazine, quinacrine, rasburicase, Rituximab, Sargramostim, streptozocin, tamoxifen, temozolomide, teniposide, testolactone, thioguanine, toremifene, Tositumomab, Trastuzumab (HERCEPTIN), tretinoin, uracil mustard, valrubicin, vinblastine, vincristine, vinorelbine or zoledronate.

In some embodiments, the payload is an immunomodulatory agent. The immunomodulatory agent can be, for example, gangcyclovir, etanercept, tacrolimus, cyclosporine, rapamycin, cyclophosphamide, azathioprine, mycophenolate mofetil or methotrexate. Alternatively, the immunomodulatory agent can be, for example, a glucocorticoid (e.g., cortisol or aldosterone) or a glucocorticoid analogue (e.g., prednisone or dexamethasone).

In some embodiments, the immunomodulatory agent is an anti-inflammatory agent, such as arylcarboxylic derivatives, pyrazole-containing derivatives, oxicam derivatives and nicotinic acid derivatives. Classes of anti-inflammatory agents include, for example, cyclooxygenase inhibitors, 5-lipoxygenase inhibitors, and leukotriene receptor antagonists.

Suitable cyclooxygenase inhibitors include meclofenamic acid, mefenamic acid, carprofen, diclofenac, diflunisal, fenbufen, fenoprofen, indomethacin, ketoprofen, nabumetone, sulindac, tenoxicam and tolmetin.

Suitable lipoxygenase inhibitors include redox inhibitors (e.g., catechol butane derivatives, nordihydroguaiaretic acid (NDGA), masoprocol, phenidone, Ianopalen, indazolinones, naphazatrom, benzofuranol, alkylhydroxylamine), and non-redox inhibitors (e.g., hydroxythiazoles, methoxyalkylthiazoles, benzopyrans and derivatives thereof, methoxytetrahydropyran, boswellic acids and acetylated derivatives of boswellic acids, and quinolinemethoxyphenylacetic acids substituted with cycloalkyl radicals), and precursors of redox inhibitors.

Other suitable lipoxygenase inhibitors include antioxidants (e.g., phenols, propyl gallate, flavonoids and/or naturally occurring substrates containing flavonoids, hydroxylated derivatives of the flavones, flavonol, dihydroquercetin, luteolin, galangin, orobol, derivatives of chalcone, 4,2',4'-trihydroxychalcone, ortho-aminophenols, N-hydroxyureas, benzofuranols, ebselen and species that increase the activity of the reducing selenoenzymes), iron chelating agents (e.g., hydroxamic acids and derivatives thereof, N-hydroxyureas, 2-benzyl-1-naphthol, catechols, hydroxylamines, camosol trolox C, catechol, naphthol, sulfasalazine, zyleuton, 5-hydroxyanthranilic acid and 4-(omega-arylalkyl)phenylalkanoic acids), imidazole-containing compounds (e.g., ketoconazole and itraconazole), phenothiazines, and benzopyran derivatives.

Yet other suitable lipoxygenase inhibitors include inhibitors of eicosanoids (e.g., octadecatetraenoic, eicosatetraenoic, docosapentaenoic, eicosahexaenoic and docosahexaenoic acids and esters thereof, PGE1 (prostaglandin E1), PGA2 (prostaglandin A2), viprostol, 15-monohydroxyeicosatetraenoic, 15-monohydroxy-eicosatrienoic and 15-monohydroxyeicosapentaenoic acids, and leukotrienes B5, C5 and D5), compounds interfering with calcium flows, phenothiazines, diphenylbutylamines, verapamil, fuscoside, curcumin, chlorogenic acid, caffeic acid, 5,8,11,14-eicosatetrayenoic acid (ETYA), hydroxyphenylretinamide, Ionapalen, esculin, diethylcarbamazine, phenantroline, baicalein, proxicromil, thioethers, diallyl sulfide and di-(1-propenyl) sulfide.

Leukotriene receptor antagonists include calcitriol, ontazolast, Bayer Bay-x-1005, Ciba-Geigy CGS-25019C, ebselen, Leo Denmark ETH-615, Lilly LY-293111, Ono ONO-4057, Terumo TMK-688, Boehringer Ingleheim BI-RM-270, Lilly LY 213024, Lilly LY 264086, Lilly LY 292728, Ono ONO LB457, Pfizer 105696, Perdue Frederick PF 10042, Rhone-Poulenc Rorer RP 66153, SmithKline Beecham SB-201146, SmithKline Beecham SB-201993, SmithKline Beecham SB-209247, Searle SC-53228, Sumitamo SM 15178, American Home Products WAY 121006, Bayer Bay-o-8276, Warner-Lambert CI-987, Wamer-Lambert CI-987BPC-15LY 223982, Lilly LY 233569, Lilly LY-255283, MacroNex MNX-160, Merck and Co. MK-591, Merck and Co. MK-886, Ono ONO-LB-448, Purdue Frederick PF-5901, Rhone-Poulenc Rorer RG14893, Rhone-Poulenc Rorer RP 66364, Rhone-Poulenc Rorer RP 69698, Shionoogi S-2474, Searle SC-41930, Searle SC-50505, Searle SC-51146, Searle SC-52798, SmithKline Beecham SK&F-104493, Leo Denmark SR-2566, Tanabe T-757 and Teijin TEI-1338.

Other useful drug payloads include chemical compounds useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafamib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamniprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Other useful payloads include: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above. Other anti-angiogenic agents include MMP-2 (matrix-metalloproteinase 2) inhibitors, MMP-9 (matrix-metalloproteinase 9) inhibitors, COX-II (cyclooxygenase II) inhibitors, and VEGF receptor tyrosine kinase inhibitors. Examples of such useful matrix metalloproteinase inhibitors that can be used in combination with the present compounds/compositions are described in WO 96/33172, WO 96/27583, EP 818442, EP 1004578, WO 98/07697, WO 98/03516, WO 98/34918, WO 98/34915, WO 98/33768, WO 98/30566, EP 606,046, EP 931,788, WO 90/05719, WO 99/52910, WO 99/52889, WO 99/29667, WO 99/07675, EP 945864, U.S. Pat. Nos. 5,863,949, 5,861,510, and EP 780,386, all of which are incorporated herein in their entireties by reference. Examples of VEGF receptor tyrosine kinase inhibitors include 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)quinazoline (AZD2171; Example 240 within WO 00/47212), vatalanib (PTK787; WO 98/35985) and SU11248 (sunitinib; WO 01/60814), and compounds such as those disclosed in PCT Publication Nos. WO 97/22596, WO 97/30035, WO 97/32856, and WO 98/13354).

In certain embodiments, the payload is an antibody or an antibody fragment. In certain embodiments, the payload antibody or fragment can be encoded by any of the immunoglobulin genes recognized by those of skill in the art. The immunoglobulin genes include, but are not limited to, the κ, λ, α, γ (IgG1, IgG2, IgG3, and IgG4), δ, ε and μ constant region genes, as well as the immunoglobulin variable region genes. The term includes full-length antibody and antibody fragments recognized by those of skill in the art, and variants thereof. Exemplary fragments include but are not limited to Fv, Fc, Fab, and (Fab')$_2$, single chain Fv (scFv), diabodies, triabodies, tetrabodies, bifunctional hybrid polypeptides, CDR1, CDR2, CDR3, combinations of CDR's, variable regions, framework regions, constant regions, and the like.

In certain embodiments, the payload is one or more water-soluble polymers. A wide variety of macromolecular polymers and other molecules can be linked to the polypeptides described herein to modulate biological properties of the polypeptide, and/or provide new biological properties to the polypeptide. These macromolecular polymers can be linked to the polypeptide via a naturally encoded amino acid, via a non-naturally encoded amino acid, or any functional substituent of a natural or modified amino acid, or any substituent or functional group added to a natural or modified amino acid. The molecular weight of the polymer may be of a wide range, including but not limited to, between about 100 Da and about 100,000 Da or more.

The polymer selected may be water soluble so that a protein to which it is attached does not precipitate in an aqueous environment, such as a physiological environment. The polymer may be branched or unbranched. Preferably, for therapeutic use of the end-product preparation, the polymer will be pharmaceutically acceptable.

In certain embodiments, the proportion of polyethylene glycol molecules to polypeptide molecules will vary, as will their concentrations in the reaction mixture. In general, the optimum ratio (in terms of efficiency of reaction in that there is minimal excess unreacted protein or polymer) may be determined by the molecular weight of the polyethylene glycol selected and on the number of available reactive groups available. As relates to molecular weight, typically the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio.

The water soluble polymer may be any structural form including but not limited to linear, forked or branched. Typically, the water soluble polymer is a poly(alkylene glycol), such as poly(ethylene glycol) (PEG), but other water soluble polymers can also be employed. By way of example, PEG is used to describe certain embodiments.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented as linked to a polypeptide by the formula: $XO-(CH_2CH_2O)_n-CH_2CH_2-Y$ where n is 2 to 10,000 and X is H or a terminal modification, including but not limited to, a $C_{1-4}$ alkyl.

In some cases, a PEG terminates on one end with hydroxy or methoxy, i.e., X is H or $CH_3$ ("methoxy PEG"). Alternatively, the PEG can terminate with a reactive group, thereby forming a bifunctional polymer. Typical reactive groups can include those reactive groups that are commonly used to react with the functional groups found in the 20 common amino acids (including but not limited to, maleimide groups, activated carbonates (including but not limited to, p-nitrophenyl ester), activated esters (including but not limited to, N-hydroxysuccinimide, p-nitrophenyl ester) and aldehydes) as well as functional groups that are inert to the 20 common amino acids but that react specifically with complementary functional groups present in non-naturally encoded amino acids (including but not limited to, azide groups, alkyne groups). It is noted that the other end of the PEG, which is shown in the above formula by Y, will attach either directly or indirectly to a polypeptide via a naturally-occurring or non-naturally encoded amino acid. For instance, Y may be an amide, carbamate or urea linkage to an amine group (including but not limited to, the epsilon amine of lysine or the N-terminus) of the polypeptide. Alternatively, Y may be a maleimide linkage to a thiol group (including but not limited to, the thiol group of cysteine). Alternatively, Y may be a linkage to a residue not commonly accessible via the 20 common amino acids. For example, an azide group on the PEG can be reacted with an alkyne group on the polypeptide to form a Huisgen [3+2] cycloaddition product. Alternatively, an alkyne group on the PEG can be reacted with an azide group present in a non-naturally encoded amino acid, such as the modified amino acids described herein, to form a similar product. In some embodiments, a strong nucleophile (including but not limited to, hydrazine, hydrazide, hydroxylamine, semicarbazide) can be reacted with an aldehyde or ketone group present in a non-naturally encoded amino acid to form a hydrazone, oxime or semicarbazone, as applicable, which in some cases can be further reduced by treatment with an appropriate reducing agent. Alternatively, the strong nucleophile can be incorporated into the polypeptide via a non-naturally encoded amino acid and used to react preferentially with a ketone or aldehyde group present in the water soluble polymer.

Any molecular mass for a PEG can be used as practically desired, including but not limited to, from about 100 Daltons (Da) to 100,000 Da or more as desired (including but not limited to, sometimes 0.1-50 kDa or 10-40 kDa). Branched chain PEGs, including but not limited to, PEG molecules with each chain having a MW ranging from 1-100 kDa (including but not limited to, 1-50 kDa or 5-20 kDa) can also be used. A wide range of PEG molecules are described in, including but not limited to, the Shearwater Polymers, Inc. catalog, Nektar Therapeutics catalog, incorporated herein by reference.

Generally, at least one terminus of the PEG molecule is available for reaction with the non-naturally-encoded amino acid. For example, PEG derivatives bearing alkyne and azide moieties for reaction with amino acid side chains can be used to attach PEG to non-naturally encoded amino acids as described herein. If the non-naturally encoded amino acid comprises an azide, then the PEG will typically contain either an alkyne moiety to effect formation of the [3+2] cycloaddition product or an activated PEG species (i.e., ester, carbonate) containing a phosphine group to effect formation of the amide linkage. Alternatively, if the non-naturally encoded amino acid comprises an alkyne, then the PEG will typically contain an azide moiety to effect formation of the [3+2] Huisgen cycloaddition product. If the non-naturally encoded amino acid comprises a carbonyl group, the PEG will typically comprise a potent nucleophile (including but not limited to, a hydrazide, hydrazine, hydroxylamine, or semicarbazide functionality) in order to effect formation of corresponding hydrazone, oxime, and semicarbazone linkages, respectively. In other alternatives, a reverse of the orientation of the reactive groups described herein can be used, i.e., an azide moiety in the non-naturally encoded amino acid can be reacted with a PEG derivative containing an alkyne.

In some embodiments, the polypeptide variant with a PEG derivative contains a chemical functionality that is reactive with the chemical functionality present on the side chain of the non-naturally encoded amino acid.

In certain embodiments, the payload is an azide- or acetylene-containing polymer comprising a water soluble polymer backbone having an average molecular weight from about 800 Da to about 100,000 Da. The polymer backbone of the water-soluble polymer can be poly(ethylene glycol). However, it should be understood that a wide variety of water soluble polymers including but not limited to poly(ethylene)glycol and other related polymers, including poly(dextran) and poly(propylene glycol), are also suitable for use and that the use of the term PEG or poly(ethylene glycol) is intended to encompass and include all such molecules. The term PEG includes, but is not limited to, poly(ethylene glycol) in any of its forms, including bifunctional PEG, multiarmed PEG, derivatized PEG, forked PEG, branched PEG, pendent PEG (i.e. PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly(ethylene glycol) can be represented in general form as $R(\text{-PEG-OH})_m$ in which R is derived from a core moiety, such as glycerol, glycerol oligomers, or pentaerythritol, and m represents the number of arms. Multi-armed PEG molecules, such as those described in U.S. Pat. Nos. 5,932,462 5,643,575; 5,229,490; 4,289,872; U.S. Pat. Appl. 2003/0143596; WO 96/21469; and WO 93/21259, each of which is incorporated by reference herein in its entirety, can also be used as the polymer backbone.

Branched PEG can also be in the form of a forked PEG represented by $PEG(\text{-YCHZ}_2)_n$, where Y is a linking group and Z is an activated terminal group linked to CH by a chain of atoms of defined length.

Yet another branched form, the pendant PEG, has reactive groups, such as carboxyl, along the PEG backbone rather than at the end of PEG chains.

In addition to these forms of PEG, the polymer can also be prepared with weak or degradable linkages in the backbone. For example, PEG can be prepared with ester linkages in the polymer backbone that are subject to hydrolysis. As shown herein, this hydrolysis results in cleavage of the polymer into fragments of lower molecular weight: -PEG-CO$_2$-PEG-+H$_2$O→PEG-CO$_2$H+HO-PEG- It is understood by those skilled in the art that the term poly(ethylene glycol) or PEG represents or includes all the forms known in the art including but not limited to those disclosed herein.

Many other polymers are also suitable for use. In some embodiments, polymer backbones that are water-soluble, with from 2 to about 300 termini, are particularly. Examples of suitable polymers include, but are not limited to, other poly(alkylene glycols), such as poly(propylene glycol) ("PPG"), copolymers thereof (including but not limited to copolymers of ethylene glycol and propylene glycol), terpolymers thereof, mixtures thereof, and the like. Although the molecular weight of each chain of the polymer backbone can vary, it is typically in the range of from about 800 Da to about 100,000 Da, often from about 6,000 Da to about 80,000 Da.

Those of ordinary skill in the art will recognize that the foregoing list for substantially water soluble backbones is by no means exhaustive and is merely illustrative, and that all polymeric materials having the qualities described herein are contemplated as being suitable for use.

In some embodiments the polymer derivatives are "multifunctional", meaning that the polymer backbone has at least two termini, and possibly as many as about 300 termini, functionalized or activated with a functional group. Multifunctional polymer derivatives include, but are not limited to, linear polymers having two termini, each terminus being bonded to a functional group which may be the same or different.

The azide functional group can be reacted selectively with a payload moiety containing an aryl ester and appropriately functionalized with an aryl phosphine moiety to generate an amide linkage. The aryl phosphine group reduces the azide in situ and the resulting amine then reacts efficiently with a proximal ester linkage to generate the corresponding amide. See, e.g., E. Saxon and C. Bertozzi, Science 287, 2007-2010 (2000). In some embodiments, the azide-containing amino acid is an alkyl azide (including but not limited to, 2-amino-6-azido-1-hexanoic acid) or an aryl azide (p-azido-phenylalanine).

Exemplary payload moieties containing an aryl ester and a phosphine moiety can be represented as follows:

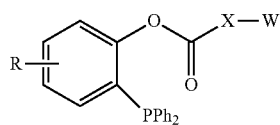

wherein X is —O—, —NH—, —S—, or a single bond, Ph is phenyl, W is a payload moiety and R is H, alkyl, aryl, substituted alkyl and substituted aryl groups. Exemplary R groups include, but are not limited to, —CH$_2$, —C(CH$_3$)$_3$, —OR', —NR'R", —SR', -halogen, —C(O)R', —CONR'R", —S(O)$_2$R', —S(O)$_2$NR'R", —CN and —NO$_2$. R', R", R''' and R'''' are each independently hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound described herein includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —CF$_3$ and —CH$_2$CF$_3$) and acyl (including but not limited to, —C(O)CH$_3$, —C(O)CF$_3$, —C(O)CH$_2$OCH$_3$, and the like).

The azide functional group can also be reacted selectively with a payload moiety containing a thioester and appropriately functionalized with an aryl phosphine moiety to generate an amide linkage. The aryl phosphine group reduces the azide in situ and the resulting amine then reacts efficiently with the thioester linkage to generate the corresponding amide. Exemplary water soluble polymers containing a thioester and a phosphine moiety can be represented as follows:

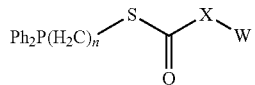

wherein n is 1-10; X can be O, N, S or not present, Ph is phenyl, and W is a payload moiety.

In one embodiment, the polymer derivative has the structure: X-A-PAY-B-alkynyl, wherein: B is a linking moiety, which may be present or absent; PAY is a payload moiety; A is a linking moiety, which may be present or absent and which may be the same as B or different; and X is a second functional group. Examples of a linking moiety for A and B include, but are not limited to, a multiply-functionalized alkyl group containing up to 18, and more preferably between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and more preferably 5-6 carbon atoms. The aryl group may be substituted with one more carbon atoms, nitrogen, oxygen or sulfur atoms. Other examples of suitable linking groups include those linking groups described in U.S. Pat. Nos. 5,932,462; 5,643,575; and U.S. Pat. Appl. Publication 2003/0143596, each of which is incorporated by reference herein. Those of ordinary skill in the art will recognize that the foregoing list for linking moieties is by no means exhaustive and is merely illustrative, and that all linking moieties having the qualities described herein are contemplated to be suitable for use.

Examples of suitable functional groups for use as X include, but are not limited to, hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, tresylate, alkene, and ketone. As is understood by those skilled in the art, the selected X moiety should be compatible with the alkynyl group so that reaction with the alkynyl group does not occur. The alkynyl-containing polymer derivatives may be homobifunctional, meaning that the second functional group (i.e., X) is also an alkynyl moiety, or heterobifunctional, meaning that the second functional group is a different functional group.

The term "protected" refers to the presence of a protecting group or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used.

Specific examples of terminal functional groups in the literature include, but are not limited to, N-succinimidyl carbonate (see e.g., U.S. Pat. Nos. 5,281,698, 5,468,478), amine (see, e.g., Buckmann et al. Makromol. Chem. 182: 1379 (1981), Zaplipsky et al. Eur. Polym. J. 19:1177 (1983)), hydrazide (See, e.g., Andresz et al. Makromol. Chem. 179:301 (1978)), succinimidyl propionate and succinimidyl butanoate (see, e.g., Olson et al. in Poly(ethylene glycol) Chemistry & Biological Applications, pp 170-181, Harris & Zaplipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al. Macrolol. Chem. 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. Eur. J Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11: 141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. Nos. 5,824,784, 5,252,714), maleimide (see, e.g., Goodson et al. Bio/Technology 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314(1993)), acrylol (see, e.g., Sawhney et al., Macromolecules, 26:581 (1993)), vinylsulfone (see, e.g., U.S. Pat. No. 5,900,461). All of the above references and patents are incorporated herein by reference.

In certain embodiments, polymer derivatives comprise a polymer backbone having the structure: X—$CH_2CH_2O$—($CH_2CH_2O$)$_n$—$CH_2CH_2$-alkynyl, wherein: X is a functional group as described herein; and n is about 20 to about 4000. In another embodiment, the polymer derivatives comprise a polymer backbone having the structure: X—$CH_2CH_2O$—($CH_2CH_2O$)$_n$—$CH_2CH_2$—O—($CH_2$)$_m$W-alkynyl wherein: W is an aliphatic or aromatic linker moiety comprising between 1-10 carbon atoms; n is about 20 to about 4000; X is a functional group as described herein; and m is between 1 and 10. Examples of suitable functional groups include, but are not limited to, hydroxyl, protected hydroxyl, acetal, alkenyl, amine, aminooxy, protected amine, protected hydrazide, protected thiol, carboxylic acid, protected carboxylic acid, maleimide, dithiopyridine, and vinylpyridine, and ketone.

Alkynyl-containing PEG derivatives can be prepared by a variety of methods known in the art and/or disclosed herein. In a method for preparation of an alkynyl-containing polymer derivative, a linking agent bearing an alkynyl functionality is contacted with a payload moiety, wherein the linking agent bears a chemical functionality that will react selectively with a chemical functionality on the PEG polymer, to form an alkynyl-containing polymer derivative product wherein the alkynyl is separated from the polymer backbone by a linking group.

An exemplary reaction scheme is shown herein: X-PEG-M+N-linker-alkynyl→PG-X-PEG-linker-alkynyl wherein: PEG is poly(ethylene glycol) and X is a capping group such as alkoxy or a functional group as described herein; and M is a functional group that is not reactive with the alkynyl functionality but that will react efficiently and selectively with the N functional group. Examples of suitable functional groups include, but are not limited to, M being a carboxylic acid, carbonate or active ester if N is an amine; M being a ketone if N is a hydrazide or aminooxy moiety; M being a leaving group if N is a nucleophile.

Purification of the crude product may be accomplished by known methods including, but are not limited to, precipitation of the product followed by chromatography, if necessary.

A more specific example is shown herein in the case of PEG diamine, in which one of the amines is protected by a protecting group moiety such as tert-butyl-Boc and the resulting mono-protected PEG diamine is reacted with a linking moiety that bears the alkynyl functionality: BocHN-PEG-NH$_2$+HO$_2$C—(CH$_2$)$_3$-alkynyl. In this instance, the amine group can be coupled to the carboxylic acid group using a variety of activating agents such as thionyl chloride or carbodiimide reagents and N-hydroxysuccinimide or N-hydroxybenzotriazole to create an amide bond between the monoamine PEG derivative and the alkynyl-bearing linker moiety. After successful formation of the amide bond, the resulting N-tert-butyl-Boc-protected alkynyl-containing derivative can be used directly to modify bioactive molecules or it can be further elaborated to install other useful functional groups. For instance, the N-t-Boc group can be hydrolyzed by treatment with strong acid to generate an omega-amino-PEG-azide. The resulting amine can be used as a synthetic handle to install other useful functionality such as maleimide groups, activated disulfides, activated esters and so forth for the creation of valuable heterobifunctional reagents.

In another embodiment, the polymer derivative has the structure: X-A-PAY-B-C≡C—R wherein: R can be either H or an alkyl, alkene, alkyoxy, or aryl or substituted aryl group; B is a linking moiety, which may be present or absent; PAY is a payload moiety; A is a linking moiety, which may be present or absent and which may be the same as B or different; and X is a second functional group.

Examples of a linking moiety for A and B include, but are not limited to, a multiply-functionalized alkyl group containing up to 18, and more preferably between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and more preferably 5-6 carbon atoms. The aryl group may be substituted with one more carbon atoms, nitrogen, oxygen, or sulfur atoms. Other examples of suitable linking groups include those linking groups described in U.S. Pat. Nos. 5,932,462 and 5,643,575 and U.S. Pat. Appl. Publication 2003/0143596, each of which is incorporated by reference herein. Those of ordinary skill in the art will recognize that the foregoing list for linking moieties is by no means exhaustive and is intended to be merely illustrative, and that a wide variety of linking moieties having the qualities described herein are contemplated to be useful.

Examples of suitable functional groups for use as X include hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate, alkene, ketone, and acetylene. As would be understood, the selected X moiety should be compatible with the acetylene group so that reaction with the acetylene group does not occur. The acetylene-containing polymer derivatives may be homobifunctional, meaning that the second functional group (i.e., X) is also an acetylene moiety, or heterobifunctional, meaning that the second functional group is a different functional group.

In another embodiment, the polymer derivatives comprise a polymer backbone having the structure: X—CH$_2$CH$_2$O—(CH$_2$CH$_2$O)$_n$—CH$_2$CH$_2$—O—(CH$_2$)$_m$C≡CH wherein: X is a functional group as described herein; n is about 20 to about 4000; and m is between 1 and 10. Specific examples of each of the heterobifunctional PEG polymers are shown herein.

The acetylene-containing PEG derivatives can be prepared using methods known to those skilled in the art and/or disclosed herein. In one method, a water soluble polymer backbone having an average molecular weight from about 800 Da to about 100,000 Da, the polymer backbone having a first terminus bonded to a first functional group and a second terminus bonded to a suitable nucleophilic group, is reacted with a compound that bears both an acetylene functionality and a leaving group that is suitable for reaction with the nucleophilic group on the PEG. When the PEG polymer bearing the nucleophilic moiety and the molecule bearing the leaving group are combined, the leaving group undergoes a nucleophilic displacement and is replaced by the nucleophilic moiety, affording the desired acetylene-containing polymer: X-PEG-Nu+L-A-C→X-PEG-Nu-A-C≡CR'.

As shown, a preferred polymer backbone for use in the reaction has the formula X-PEG-Nu, wherein PEG is poly (ethylene glycol), Nu is a nucleophilic moiety and X is a functional group that does not react with Nu, L or the acetylene functionality.

Examples of Nu include, but are not limited to, amine, alkoxy, aryloxy, sulfhydryl, imino, carboxylate, hydrazide, aminoxy groups that would react primarily via a SN2-type mechanism. Additional examples of Nu groups include those functional groups that would react primarily via an nucleophilic addition reaction. Examples of L groups include chloride, bromide, iodide, mesylate, tresylate, and tosylate and other groups expected to undergo nucleophilic displacement as well as ketones, aldehydes, thioesters, olefins, alpha-beta unsaturated carbonyl groups, carbonates and other electrophilic groups expected to undergo addition by nucleophiles.

In another embodiment, A is an aliphatic linker of between 1-10 carbon atoms or a substituted aryl ring of between 6-14 carbon atoms. X is a functional group which does not react with alkynyl groups and L is a suitable leaving group.

In another method for preparation of the acetylene-containing polymer derivatives, a PEG polymer having an average molecular weight from about 800 Da to about 100,000 Da, bearing either a protected functional group or a capping agent at one terminus and a suitable leaving group at the other terminus is contacted by an acetylene anion.

Water soluble polymers can be linked to the polypeptides. The water soluble polymers may be linked via a non-naturally encoded amino acid incorporated in the polypeptides or any functional group or substituent of a non-naturally encoded or naturally encoded amino acid, or any functional group or substituent added to a non-naturally encoded or naturally encoded amino acid. In an embodiment, the non-naturally encoded amino acid is a modified amino acid as described herein. Alternatively, the water soluble polymers are linked to an antigen-binding antibody incorporating a non-naturally encoded amino acid via a naturally-occurring amino acid (including but not limited to, cysteine, lysine or the amine group of the N-terminal residue). In some cases, the polypeptides comprise 1, 2, 3, 4, 5, 6, 7, 8, 9, 10 modified amino acids, wherein one or more non-naturally-encoded amino acid(s) are linked to water soluble polymer(s) (including but not limited to, PEG and/or oligosaccharides). In some cases, the polypeptides further comprise 1, 2, 3, 4, 5, 6, 7, 8, 9, 10, or more naturally-encoded amino acid(s) linked to water soluble polymers. In some cases, the polypeptides comprise one or more non-naturally encoded amino acid(s) linked to water soluble polymers and one or more naturally-occurring amino acids linked to water soluble polymers. In some embodiments, the water soluble polymers enhance the serum half-life of the polypeptides relative to the unconjugated form.

The number of water soluble polymers linked to a polypeptide (i.e., the extent of PEGylation or glycosylation) can be adjusted to provide an altered (including but not limited to, increased or decreased) pharmacologic, pharmacokinetic or pharmacodynamic characteristic such as in vivo half-life. In some embodiments, the half-life of a polypeptide is increased at least about 10, 20, 30, 40, 50, 60, 70, 80, 90 percent, 2-fold, 5-fold, 10-fold, 50-fold, or at least about 100-fold over an unmodified polypeptide.

In one embodiment, a polypeptide comprising a carbonyl-containing non-naturally encoded amino acid is modified with a PEG derivative that contains a terminal hydrazine, hydroxylamine, hydrazide or semicarbazide moiety that is linked directly to the PEG backbone.

In some embodiments, the hydroxylamine-terminal PEG derivative will have the structure: RO—$(CH_2CH_2O)_n$—O—$(CH_2)_m$O—$NH_2$ where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PEG derivative will have the structure: RO—$(CH_2CH_2O)_n$O—$(CH_2)_m$—X—NH—$NH_2$ where R is a simple alkyl (methyl, ethyl, propyl, etc.), m is 2-10 and n is 100-1,000 and X is optionally a carbonyl group (C=O) that can be present or absent.

In some embodiments, the semicarbazide-containing PEG derivative will have the structure: RO—$(CH_2CH_2O)_n$O—$(CH_2)_m$NH—C(O)—NH—$NH_2$ where R is a simple alkyl (methyl, ethyl, propyl, etc.), m is 2-10 and n is 100-1,000.

In another embodiment, a polypeptide comprising a carbonyl-containing amino acid is modified with a PEG derivative that contains a terminal hydroxylamine, hydrazide, hydrazine, or semicarbazide moiety that is linked to the PEG backbone by means of an amide linkage.

In some embodiments, the hydroxylamine-terminal PEG derivatives have the structure: RO—$(CH_2CH_2O)_n$—O—$(CH_2)_2$—NH—$C(O)(CH_2)_m$—O—$NH_2$ where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PEG derivatives have the structure: RO—$(CH_2CH_2O)_n$O—$(CH_2)_2$—NH—$C(O)(CH_2)_m$—X—NH—$NH_2$ where R is a simple alkyl (methyl, ethyl, propyl, etc.), m is 2-10, n is 100-1,000 and X is optionally a carbonyl group (C=O) that can be present or absent.

In some embodiments, the semicarbazide-containing PEG derivatives have the structure: RO—$(CH_2CH_2O)_n$—O—$(CH_2)_2$—NH—$C(O)(CH_2)_m$—NH—C(O)—NH—$NH_2$ where R is a simple alkyl (methyl, ethyl, propyl, etc.), m is 2-10 and n is 100-1,000.

In another embodiment, a polypeptide comprising a carbonyl-containing amino acid is modified with a branched PEG derivative that contains a terminal hydrazine, hydroxylamine, hydrazide or semicarbazide moiety, with each chain of the branched PEG having a MW ranging from 10-40 kDa and, more preferably, from 5-20 kDa.

In another embodiment, a polypeptide comprising a non-naturally encoded amino acid is modified with a PEG derivative having a branched structure. For instance, in some embodiments, the hydrazine- or hydrazide-terminal PEG derivative will have the following structure: [RO—$(CH_2CH_2O)_n$O—$(CH_2)_2$—NH—$C(O)]_2CH(CH_2)_m$—X—NH—$NH_2$ where R is a simple alkyl (methyl, ethyl, propyl, etc.), m is 2-10 and n is 100-1,000, and X is optionally a carbonyl group (C=O) that can be present or absent.

In some embodiments, the PEG derivatives containing a semicarbazide group will have the structure: [RO—$(CH_2CH_2O)_n$—O—$(CH_2)_2$—C(O)—NH—$CH_2$—$CH_2]_2CH$—X—$(CH_2)_m$—NH—C(O)—NH—$NH_2$ where R is a simple alkyl (methyl, ethyl, propyl, etc.), X is optionally NH, O, S, C(O) or not present, m is 2-10 and n is 100-1,000.

In some embodiments, the PEG derivatives containing a hydroxylamine group will have the structure: [RO—$(CH_2CH_2O)_n$—O—$(CH_2)_2$—C(O)—NH—$CH_2$—$CH_2]_2CH$—X—$(CH_2)_m$—O—$NH_2$ where R is a simple alkyl (methyl, ethyl, propyl, etc.), X is optionally NH, O, S, C(O) or not present, m is 2-10 and n is 100-1,000.

The degree and sites at which water soluble polymer(s) are linked to the polypeptides can modulate the binding of the polypeptides to an antigen or receptor.

Methods and chemical properties for activation of polymers as well as for conjugation of peptides are described in the literature and are known in the art. Commonly used methods for activation of polymers include, but are not limited to, activation of functional groups with cyanogen bromide, periodate, glutaraldehyde, biepoxides, epichlorohydrin, divinylsulfone, carbodiimide, sulfonyl halides, trichlorotriazine, etc. (see, R. F. Taylor, (1991), PROTEIN IMMOBILISATION. FUNDAMENTAL AND APPLICATIONS, Marcel Dekker, N.Y.; S. S. Wong, (1992), CHEMISTRY OF PROTEIN CONJUGATION AND CROSS-LINKING, CRC Press, Boca Raton; G. T. Hermanson et al., (1993), IMMOBILIZED AFFINITY LIGAND TECHNIQUES, Academic Press, N.Y.; Dunn, R. L., et al., Eds. POLYMERIC DRUGS AND DRUG DELIVERY SYSTEMS, ACS Symposium Series Vol. 469, American Chemical Society, Washington, D.C. 1991).

Several reviews and monographs on the functionalization and conjugation of PEG are available. See, for example, Harris, Macronol. Chem. Phys. C25: 325-373 (1985); Scouten, Methods in Enzymology 135: 30-65 (1987); Wong et al., Enzyme Microb. Technol. 14: 866-874 (1992); Delgado et al., Critical Reviews in Therapeutic Drug Carrier Systems 9: 249-304 (1992); Zalipsky, Bioconjugate Chem. 6: 150-165 (1995).

Methods for activation of polymers can also be found in WO 94/17039, U.S. Pat. No. 5,324,844, WO 94/18247, WO 94/04193, U.S. Pat. Nos. 5,219,564, 5,122,614, WO 90/13540, U.S. Pat. No. 5,281,698, and WO 93/15189, and for conjugation between activated polymers and enzymes including but not limited to Coagulation Factor VIII (WO 94/15625), hemoglobin (WO 94/09027), oxygen carrying molecule (U.S. Pat. No. 4,412,989), ribonuclease and superoxide dismutase (Veronese at al., App. Biochem. Biotech. 11: 141-45 (1985)). All references and patents cited herein are incorporated by reference in their entireties.

PEGylation (i.e., addition of any water soluble polymer) of polypeptides containing a non-naturally encoded amino acid, such as p-azido-L-phenylalanine, is carried out by any convenient method. For example, a polypeptide is PEGylated with an alkyne-terminated mPEG derivative. Briefly, an excess of solid mPEG(5000)-O—$CH_2$—C≡CH is added, with stirring, to an aqueous solution of p-azido-L-Phecontaining polypeptide at room temperature. Typically, the aqueous solution is buffered with a buffer having a p$K_a$ near the pH at which the reaction is to be carried out (generally about pH 4-10). Examples of suitable buffers for PEGylation at pH 7.5, for instance, include, but are not limited to, HEPES, phosphate, borate, TRIS-HCl, EPPS, and TES. The pH is continuously monitored and adjusted if necessary. The reaction is typically allowed to continue for between about 1-48 hours.

The reaction products are subsequently subjected to hydrophobic interaction chromatography to separate the PEGylated polypeptide variants from free mPEG(5000)-O—$CH_2$—C≡CH and any high-molecular weight complexes of the pegylated polypeptide which may form when unblocked PEG is activated at both ends of the molecule, thereby crosslinking polypeptide variant molecules. The conditions during hydrophobic interaction chromatography are such that free mPEG(5000)-O—$CH_2$—C≡CH flows through the column, while any crosslinked PEGylated polypeptide variant complexes elute after the desired forms, which contain one polypeptide variant molecule conjugated to one or more PEG groups. Suitable conditions vary depending on the relative sizes of the cross-linked complexes versus the desired conjugates and are readily determined by those skilled in the art. The eluent containing the desired conjugates is concentrated by ultrafiltration and desalted by diafiltration.

If necessary, the PEGylated polypeptide obtained from the hydrophobic chromatography can be purified further by one or more procedures known to those skilled in the art including, but are not limited to, affinity chromatography; anion- or cation-exchange chromatography (using, including but not limited to, DEAE SEPHAROSE); chromatography on silica; reverse phase HPLC; gel filtration (using, including but not limited to, SEPHADEX G-75); hydrophobic interaction chromatography; size-exclusion chromatography, metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), or extraction. Apparent molecular weight may be estimated by GPC by comparison to globular protein standards (PROTEIN PURIFICATION METHODS, A PRACTICAL APPROACH (Harris & Angal, Eds.) IRL Press 1989, 293-306). The purity of the polypeptide-PEG conjugate can be assessed by proteolytic degradation (including but not limited to, trypsin cleavage) followed by mass spectrometry analysis. Pepinsky B., et al., J. Pharmcol. & Exp. Ther. 297(3):1059-66 (2001).

A water soluble polymer linked to an amino acid of a polypeptide can be further derivatized or substituted without limitation.

In another embodiment, a polypeptide is modified with a PEG derivative that contains an azide moiety that will react with an alkyne moiety present on the side chain of the non-naturally encoded amino acid. In general, the PEG derivatives will have an average molecular weight ranging from 1-100 kDa and, in some embodiments, from 10-40 kDa.

In some embodiments, the azide-terminal PEG derivative will have the structure: RO—$(CH_2CH_2O)_n$—O—$(CH_2)_m$—$N_3$ where R is a simple alkyl (methyl, ethyl, propyl, etc.), m is 2-10 and n is 100-1,000 (i.e., average molecular weight is between 5-40 kDa).

In another embodiment, the azide-terminal PEG derivative will have the structure: RO—$(CH_2CH_2O)_n$O—$(CH_2)_m$—NH—C(O)—$(CH_2)_p$—$N_3$, where R is a simple alkyl (methyl, ethyl, propyl, etc.), m is 2-10, p is 2-10 and n is 100-1,000 (i.e., average molecular weight is between 5-40 kDa).

In another embodiment, a polypeptide comprising an alkyne-containing amino acid is modified with a branched PEG derivative that contains a terminal azide moiety, with each chain of the branched PEG having a MW ranging from 10-40 kDa and, more preferably, from 5-20 kDa. For instance, in some embodiments, the azide-terminal PEG derivative will have the following structure: [RO—$(CH_2CH_2O)_n$O—$(CH_2)_2$—NH—C(O)]$_2$CH$(CH_2)_m$—X—$(CH_2)_p$—$N_3$ where R is a simple alkyl (methyl, ethyl, propyl, etc.), m is 2-10, p is 2-10, and n is 100-1,000, and X is optionally an O, N, S or carbonyl group (C═O), in each case that can be present or absent.

In another embodiment, a polypeptide is modified with a PEG derivative that contains an alkyne moiety that will react with an azide moiety present on the side chain of the non-naturally encoded amino acid, such as a modified amino acid described herein.

In some embodiments, the alkyne-terminal PEG derivative will have the following structure: RO—$(CH_2CH_2O)_n$—O—$(CH_2)_m$—C≡CH where R is a simple alkyl (methyl, ethyl, propyl, etc.), m is 2-10 and n is 100-1,000 (i.e., average molecular weight is between 5-40 kDa).

In another embodiment, a polypeptide comprising an alkyne-containing non-naturally encoded amino acid is modified with a PEG derivative that contains a terminal azide or terminal alkyne moiety that is linked to the PEG backbone by means of an amide linkage.

In some embodiments, the alkyne-terminal PEG derivative will have the following structure: RO—$(CH_2CH_2O)_n$O—$(CH_2)_m$NH—C(O)—$(CH_2)_p$—C≡CH where R is a simple alkyl (methyl, ethyl, propyl, etc.), m is 2-10, p is 2-10 and n is 100-1,000.

In another embodiment, a polypeptide comprising an azide-containing amino acid is modified with a branched PEG derivative that contains a terminal alkyne moiety, with each chain of the branched PEG having a MW ranging from 10-40 kDa and, more preferably, from 5-20 kDa. For instance, in some embodiments, the alkyne-terminal PEG derivative will have the following structure: [RO—$(CH_2CH_2O)_n$—O—$(CH_2)_2$—NH—C(O)]$_2$CH$(CH_2)_m$—X—$(CH_2)_p$C≡CH where R is a simple alkyl (methyl, ethyl, propyl, etc.), m is 2-10, p is 2-10, and n is 100-1,000, and X is optionally an O, N, S or carbonyl group (C═O), or not present.

In another embodiment, a polypeptide is modified with a PEG derivative that contains an activated functional group (including but not limited to, ester, carbonate) further comprising an aryl phosphine group that will react with an azide moiety present on the side chain of the non-naturally encoded amino acid. In general, the PEG derivatives will have an average molecular weight ranging from 1-100 kDa and, in some embodiments, from 10-40 kDa.

Other exemplary PEG molecules that may be linked to polypeptides, as well as PEGylation methods include those described in, e.g., U.S. Patent Publication Nos. 2004/0001838; 2002/0052009; 2003/0162949; 2004/0013637; 2003/0228274; 2003/0220447; 2003/0158333; 2003/0143596; 2003/0114647; 2003/0105275; 2003/0105224; 2003/0023023; 2002/0156047; 2002/0099133; 2002/0086939; 2002/0082345; 2002/0072573; 2002/0052430; 2002/0040076; 2002/0037949; 2002/0002250; 2001/

0056171; 2001/0044526; 2001/0027217; 2001/0021763; U.S. Pat. Nos. 6,646,110; 5,824,778; 5,476,653; 5,219,564; 5,629,384; 5,736,625; 4,902,502; 5,281,698; 5,122,614; 5,473,034; 5,516,673; 5,382,657; 6,552,167; 6,610,281; 6,515,100; 6,461,603; 6,436,386; 6,214,966; 5,990,237; 5,900,461; 5,739,208; 5,672,662; 5,446,090; 5,808,096; 5,612,460; 5,324,844; 5,252,714; 6,420,339; 6,201,072; 6,451,346; 6,306,821; 5,559,213; 5,612,460; 5,747,646; 5,834,594; 5,849,860; 5,980,948; 6,004,573; 6,129,912; WO 97/32607, EP 229,108, EP 402,378, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, WO 98/05363, EP 809 996, WO 96/41813, WO 96/07670, EP 605 963, EP 510 356, EP 400 472, EP 183 503 and EP 154 316, which are incorporated by reference herein. Any of the PEG molecules described herein may be used in any form, including but not limited to, single chain, branched chain, multiarm chain, single functional, bi-functional, multi-functional, or any combination thereof.

In certain embodiments, the polypeptides can be linked to the payloads with one or more linkers capable of reacting with the modified amino acid. The one or more linkers can be any linkers apparent to those of skill in the art. The term "linker" is used herein to refer to groups or bonds that normally are formed as the result of a chemical reaction and typically are covalent linkages. Hydrolytically stable linkages means that the linkages are substantially stable in water and do not react with water at useful pH values, including but not limited to, under physiological conditions for an extended period of time, perhaps even indefinitely. Hydrolytically unstable or degradable linkages mean that the linkages are degradable in water or in aqueous solutions, including for example, blood. Enzymatically unstable or degradable linkages mean that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide. Branched linkers may be used in polypeptides. A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. The length of the linker may be predetermined or selected depending upon a desired spatial relationship between the polypeptide and the molecule linked to it. In view of the large number of methods that have been reported for attaching a variety of radiodiagnostic compounds, radiotherapeutic compounds, drugs, toxins, and other agents to polypeptides one skilled in the art will be able to determine a suitable method for attaching a given agent to a polypeptide.

Any hetero- or homo-bifunctional linker can be used to link the conjugates. The linker may have a wide range of molecular weight or molecular length. Larger or smaller molecular weight linkers may be used to provide a desired spatial relationship or conformation between the polypeptide and the linked entity. Linkers having longer or shorter molecular length may also be used to provide a desired space or flexibility between the polypeptide and the linked entity. Similarly, a linker having a particular shape or conformation may be utilized to impart a particular shape or conformation to the polypeptide or the linked entity, either before or after the polypeptide reaches its target. The functional groups present on each end of the linker may be selected to modulate the release of a polypeptide or a payload under desired conditions. This optimization of the spatial relationship between the polypeptide and the linked entity may provide new, modulated, or desired properties to the molecule.

In some embodiments, provided herein water-soluble bifunctional linkers that have a dumbbell structure that includes: a) an azide, an alkyne, a hydrazine, a hydrazide, a hydroxylamine, or a carbonyl-containing moiety on at least a first end of a polymer backbone; and b) at least a second functional group on a second end of the polymer backbone. The second functional group can be the same or different as the first functional group. The second functional group, in some embodiments, is not reactive with the first functional group. In some embodiments, water-soluble compounds that comprise at least one arm of a branched molecular structure are provided. For example, the branched molecular structure can be a dendritic structure.

Polypeptide Compositions

Polypeptides described herein can be formulated into compositions using methods available in the art and those disclosed herein. Any of the compounds disclosed herein can be provided in the appropriate pharmaceutical composition and be administered by a suitable route of administration.

In certain embodiments, the polypeptide compositions provided herein further comprise a pharmaceutically acceptable carrier. The carrier can be a diluent, excipient, or vehicle with which the pharmaceutical composition is administered. Such pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in E. W. Martin, 1990, Remington's Pharmaceutical Sciences, Mack Publishing Co.

In some embodiments, the pharmaceutical composition is provided in a form suitable for administration to a human subject. In some embodiments, the pharmaceutical composition will contain a prophylactically or therapeutically effective amount of the polypeptide together with a suitable amount of carrier so as to provide the form for proper administration to the patient. The formulation should suit the mode of administration.

In some embodiments, the pharmaceutical composition is provided in a form suitable for intravenous administration. Typically, compositions suitable for intravenous administration are solutions in sterile isotonic aqueous buffer. Where necessary, the composition may also include a solubilizing agent and a local anesthetic such as lignocaine to ease pain at the site of the injection. Such compositions, however, may be administered by a route other than intravenous administration.

In particular embodiments, the pharmaceutical composition is suitable for subcutaneous administration. In particular embodiments, the pharmaceutical composition is suitable for intramuscular administration.

Components of the pharmaceutical composition can be supplied either separately or mixed together in unit dosage form, for example, as a dry lyophilized powder or water free concentrate. Where the composition is to be administered by infusion, it can be dispensed with an infusion bottle containing sterile pharmaceutical grade water or saline. Where the composition is administered by injection, an ample of sterile water for injection or saline can be provided so that the ingredients may be mixed prior to administration.

In some embodiments, the pharmaceutical composition is supplied as a dry sterilized lyophilized powder that is capable of being reconstituted to the appropriate concentration for administration to a subject. In some embodiments, polypeptides are supplied as a water free concentrate. In some embodiments, the polypeptide is supplied as a dry sterile lyophilized powder at a unit dosage of at least 0.5 mg, at least 1 mg, at least 2 mg, at least 3 mg, at least 5 mg, at least 10 mg, at least 15 mg, at least 25 mg, at least 30 mg, at least 35 mg, at least 45 mg, at least 50 mg, at least 60 mg, or at least 75 mg.

In another embodiment, the pharmaceutical composition is supplied in liquid form. In some embodiments, the pharmaceutical composition is provided in liquid form and is substantially free of surfactants and/or inorganic salts. In some embodiments, the polypeptide is supplied as in liquid form at a unit dosage of at least 0.1 mg/ml, at least 0.5 mg/ml, at least 1 mg/ml, at least 2.5 mg/ml, at least 3 mg/ml, at least 5 mg/ml, at least 8 mg/ml, at least 10 mg/ml, at least 15 mg/ml, at least 25 mg/ml, at least 30 mg/ml, or at least 60 mg/ml.

In some embodiments, the pharmaceutical composition is formulated as a salt form. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

In therapeutic use, the practitioner will determine the posology most appropriate according to a preventive or curative treatment and according to the age, weight, stage of the infection and other factors specific to the subject to be treated. In certain embodiments, doses are from about 1 to about 1000 mg per day for an adult, or from about 5 to about 250 mg per day or from about 10 to 50 mg per day for an adult. In certain embodiments, doses are from about 5 to about 400 mg per day or 25 to 200 mg per day per adult. In certain embodiments, dose rates of from about 50 to about 500 mg per day are also contemplated.

Methods of Use for Therapy or Prophylaxis

Certain polypeptides provided herein can be used for the treatment or prevention of any disease or condition deemed suitable to the practitioner of skill in the art. Generally, a method of treatment or prevention encompasses the administration of a therapeutically or prophylactically effective amount of the polypeptide or polypeptide composition to a subject in need thereof to treat or prevent the disease or condition.

A therapeutically effective amount of the polypeptide or composition is an amount that is effective to reduce the severity, the duration and/or the symptoms of a particular disease or condition. The amount of the polypeptide or composition that will be therapeutically effective in the prevention, management, treatment and/or amelioration of a particular disease can be determined by standard clinical techniques. The precise amount of the polypeptide or composition to be administered with depend, in part, on the route of administration, the seriousness of the particular disease or condition, and should be decided according to the judgment of the practitioner and each subject's circumstances.

In some embodiments, the effective amount of the polypeptide provided herein is between about 0.025 mg/kg and about 1000 mg/kg body weight of a human subject. In certain embodiments, the polypeptide is administered to a human subject at an amount of about 1000 mg/kg body weight or less, about 950 mg/kg body weight or less, about 900 mg/kg body weight or less, about 850 mg/kg body weight or less, about 800 mg/kg body weight or less, about 750 mg/kg body weight or less, about 700 mg/kg body weight or less, about 650 mg/kg body weight or less, about 600 mg/kg body weight or less, about 550 mg/kg body weight or less, about 500 mg/kg body weight or less, about 450 mg/kg body weight or less, about 400 mg/kg body weight or less, about 350 mg/kg body weight or less, about 300 mg/kg body weight or less, about 250 mg/kg body weight or less, about 200 mg/kg body weight or less, about 150 mg/kg body weight or less, about 100 mg/kg body weight or less, about 95 mg/kg body weight or less, about 90 mg/kg body weight or less, about 85 mg/kg body weight or less, about 80 mg/kg body weight or less, about 75 mg/kg body weight or less, about 70 mg/kg body weight or less, or about 65 mg/kg body weight or less.

In some embodiments, the effective amount of polypeptide provided herein is between about 0.025 mg/kg and about 60 mg/kg body weight of a human subject. In some embodiments, the effective amount of a polypeptide of the pharmaceutical composition provided herein is about 0.025 mg/kg or less, about 0.05 mg/kg or less, about 0.10 mg/kg or less, about 0.20 mg/kg or less, about 0.40 mg/kg or less, about 0.80 mg/kg or less, about 1.0 mg/kg or less, about 1.5 mg/kg or less, about 3 mg/kg or less, about 5 mg/kg or less, about 10 mg/kg or less, about 15 mg/kg or less, about 20 mg/kg or less, about 25 mg/kg or less, about 30 mg/kg or less, about 35 mg/kg or less, about 40 mg/kg or less, about 45 mg/kg or less, about 50 mg/kg or about 60 mg/kg or less.

The pharmaceutical composition of the method can be administered using any method known to those skilled in the art. For example, the pharmaceutical composition can be administered intramuscularly, intradermally, intraperitoneally, intravenously, subcutaneously administration, or any combination thereof. In some embodiments, the pharmaceutical composition is administered subcutaneously. In some embodiments, the composition is administered intravenously. In some embodiments, the composition is administered intramuscularly.

Methods of Use for Detection or Diagnosis

The polypeptides provided herein can be used for the detection of any target or for the diagnosis of any disease or condition deemed suitable to the practitioner of skill in the art. The methods encompass detecting the binding of a polypeptide to a target in an appropriate location, e.g., the appropriate body, tissue, or cell. In the methods, the formation of a complex between the polypeptide and target can be detected by any method known to those of skill in the art. Examples include assays that use secondary reagents for detection, ELISA's and immunoprecipitation and agglutination assays. A detailed description of these assays is, for example, given in Harlow and Lane, Polypeptides: A Laboratory Manual (Cold Spring Harbor Laboratory, New York 1988 555-612, WO96/13590 to Maertens and Stuyver, Zrein et al. (1998) and WO96/29605.

For in situ diagnosis, the polypeptide may be administered to a subject by methods known in the art such as, for example, intravenous, intranasal, intraperitoneal, intracerebral, intraarterial injection such that a specific binding between a polypeptide with an epitopic region on the amyloid protein may occur. The polypeptide/target complex may conveniently be detected through a label attached to the polypeptide or any other art-known method of detection.

Further provided herein are kits for detection or diagnosis. Exemplary kits comprise one or more polypeptides provided herein along with one or more reagents useful for detecting a complex between the one or more polypeptides and their targets.

Preparation of Polypeptides Comprising a Modified Amino Acid

The polypeptides described herein can be prepared by any technique apparent to those of skill in the art without limitation. Useful techniques for preparation include in vivo synthesis, for example with modified tRNA and tRNA synthetase, cell-free synthesis, for example with modified tRNA and tRNA synthetase, solid phase polypeptide synthesis and liquid phase polypeptide synthesis. Exemplary techniques are described in this section and in the examples herein. In particular embodiments, the polypeptide is an antibody or antibody fragment.

In certain methods, the polypeptide is translated and/or transcribed from one or more polynucleotides encoding the polypeptide. Accordingly, provided herein are polynucleotides capable of encoding the polypeptides having one or more modified amino acids at site-specific positions in one or more polypeptide chains. In certain embodiments, the polynucleotides comprise a codon not normally associated with an amino acid at the polynucleotide position corresponding to the site-specific polypeptide position for the modified amino acid. Examples of such codons include stop codons, 4 bp codons, 5 bp codons, and the like. The reaction mixture typically comprises a tRNA synthetase capable of making tRNAs that complement (suppress) said codon. These suppressor tRNAs are linked to the modified amino acids to facilitate their incorporation into the polypeptide at the site of the suppressor codon.

The polypeptides can be prepared by techniques known to those of skill in the art for expressing polynucleotides to incorporate modified amino acids into site specific positions of a polypeptide. Such techniques are described, for example, in U.S. Pat. Nos. 7,045,337 and 7,083,970, in U.S. Published Patent Application Nos. US 2008/0317670, US 2009/0093405, US 2010/0093082, US 2010/0098630, US 2008/0085277 and in international patent publication nos. WO 2004/016778 A1 and WO 2008/066583 A2, the contents of which are hereby incorporated by reference in their entireties.

In certain embodiments, a polypeptide can be prepared in a cell-free reaction mixture comprising at least one orthogonal tRNA aminoacylated with a modified amino acid, where the orthogonal tRNA base pairs with a codon that is not normally associated with an amino acid, e.g. a stop codon; a 4 bp codon, etc. The reaction mixture also comprises a tRNA synthetase capable of aminoacylating the orthogonal tRNA with a modified amino acid. One tRNA synthetase that can be used is shown as SEQ ID NO:55 and 56 in US Patent Publication No. 2008/0233611. Wild-type tyrosyl m. janashcii tRNA may also be used. Usually the orthogonal tRNA synthetase, which is susceptible to degradation by proteases present in bacterial cell extracts, is exogenously synthesized and added to the reaction mix prior to initiation of polypeptide synthesis. The orthogonal tRNA may be synthesized in the bacterial cells from which the cell extract is obtained, may be synthesized de novo during the polypeptide synthesis reaction, or may be exogenously added to the reaction mix.

In certain embodiments, components that affect modified amino acid insertion and protein insertion or folding are optionally added to the reaction mixture. Such components include elevated concentrations of translation factors to minimize the effect of release factor 1 and 2 and to further optimize orthogonal component concentrations. Protein chaperones (Dsb System of oxidoreductases and isomerases, GroES, GroEL, DNAJ, DNAK, Skp, etc.) may be exogenously added to the reaction mixture or may be overexpressed in the source cells used to prepare the cell extract The reactions may utilize a large scale reactor, small scale, or may be multiplexed to perform a plurality of simultaneous syntheses. Continuous reactions will use a feed mechanism to introduce a flow of reagents, and may isolate the end-product as part of the process. Batch systems are also of interest, where additional reagents may be introduced to prolong the period of time for active synthesis. A reactor may be run in any mode such as batch, extended batch, semi-batch, semi-continuous, fed-batch and continuous, and which will be selected in accordance with the application purpose. The reactions may be of any volume, either in a small scale, usually at least about 1 μl and not more than about 15 μl, or in a scaled up reaction, where the reaction volume is at least about 15 μl, usually at least about 50 μl, more usually at least about 100 μl, and may be 500 μl, 1000 μl, or greater. In principle, reactions may be conducted at any scale as long as sufficient oxygen (or other electron acceptor) is supplied when needed.

Useful methods for synthesis where at least one modified amino acid is introduced into the polypeptide strand during elongation include but are not limited to: (I) addition of exogenous purified orthogonal synthetase, modified amino acid, and orthogonal tRNA to the cell-free reaction, (II) addition of exogenous purified orthogonal synthetase and modified amino acid to the reaction mixture, but with orthogonal tRNA transcribed during the cell-free reaction, (III) addition of exogenous purified orthogonal synthetase and modified amino acid to the reaction mixture, but with orthogonal tRNA synthesized by the cell extract source organism. In certain embodiments, the orthogonal components are driven by regulatable promoters, so that synthesis levels can be controlled although other measures may be used such as controlling the level of the relevant DNA templates by addition or specific digestion.

In certain embodiments, tRNA synthetase is exogenously synthesized and added to the cell-free reaction mix. In certain embodiments, the reaction mix is prepared from bacterial cells in which ompT has been inactivated or is naturally inactive. OmpT is believed to degrade components of the reaction mixture including tRNA synthetase.

In addition to the above components such as cell-free extract, genetic template, and amino acids, materials specifically required for protein synthesis may be added to the reaction. These materials include salts, folinic acid, cyclic AMP, inhibitors for protein or nucleic acid degrading enzymes, inhibitors or regulators of protein synthesis, adjusters of oxidation/reduction potential(s), non-denaturing surfactants, buffer components, spermine, spermidine, putrescine, etc.

The salts preferably include potassium, magnesium, and ammonium salts (e.g. of acetic acid or glutamic acid). One or more of such salts may have an alternative amino acid as a counter anion. There is an interdependence among ionic species for optimal concentration. These ionic species are typically optimized with regard to protein production. When changing the concentration of a particular component of the reaction medium, that of another component may be changed accordingly. For example, the concentrations of several components such as nucleotides and energy source compounds may be simultaneously adjusted in accordance with the change in those of other components. Also, the concentration levels of components in the reactor may be varied over time. The adjuster of oxidation/reduction potential may be dithiothreitol, ascorbic acid, glutathione and/or their oxidized forms.

In certain embodiments, the reaction can proceed in a dialysis mode, in a diafiltration batch mode, in a fed-batch mode of in a semi-continuous operation mode. In certain embodiments, a feed solution can be supplied to the reactor through a membrane or through an injection unit. Synthesized polypeptide can accumulate in the reactor followed by isolation or purification after completion of the system operation. Vesicles containing the polypeptide may also be continuously isolated, for example by affinity adsorption from the reaction mixture either in situ or in a circulation loop as the reaction fluid is pumped past the adsorption matrix.

During protein synthesis in the reactor, the protein isolating means for selectively isolating the desired protein may include a unit packed with particles coated with polypeptide molecules or other molecules for adsorbing the synthesized, desired protein. Preferably, the protein isolating means comprises two columns for alternating use.

The resulting polypeptide can be purified or isolated by standard techniques. Exemplary techniques are provided in the examples herein.

Assay Methods

Polypeptides can be assayed for their expected activity, or for a new activity, according to any assay apparent to those of skill in the art. The resulting polypeptide can be assayed for activity in a functional assay or by quantitating the amount of protein present in a non-functional assay, e.g. immunostaining, ELISA, quantitation on Coomasie or silver stained gel, etc., and determining the ratio of biologically active protein to total protein.

The amount of protein produced in a translation reaction can be measured in various fashions. One method relies on the availability of an assay which measures the activity of the particular protein being translated. An example of an assay for measuring protein activity is a luciferase assay system, or chloramphenical acetyl transferase assay system. These assays measure the amount of functionally active protein produced from the translation reaction. Activity assays will not measure full length protein that is inactive due to improper protein folding or lack of other post translational modifications necessary for protein activity.

Another method of measuring the amount of protein produced in coupled in vitro transcription and translation reactions is to perform the reactions using a known quantity of radiolabeled amino acid such as $^{35}$S-methionine, $^3$H-leucine or $^{14}$C-leucine and subsequently measuring the amount of radiolabeled amino acid incorporated into the newly translated protein. Incorporation assays will measure the amount of radiolabeled amino acids in all proteins produced in an in vitro translation reaction including truncated protein products. The radiolabeled protein may be further separated on a protein gel, and by autoradiography confirmed that the product is the proper size and that secondary protein products have not been produced.

Preparation of Modified Amino Acids

The compounds provided herein can be prepared, isolated or obtained by any method apparent to those of skill in the art. Compounds provided herein can be prepared according to the General Preparation Scheme provided herein. Reaction conditions, steps and reactants not provided in the General Preparation Scheme would be apparent to, and known by, those skilled in the art.

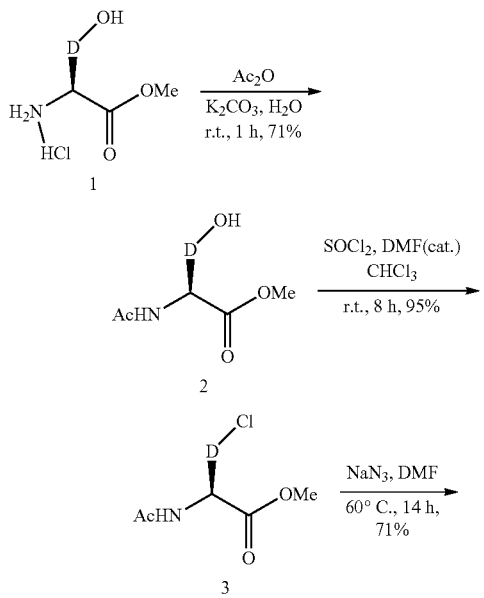

General Preparation Scheme Ia

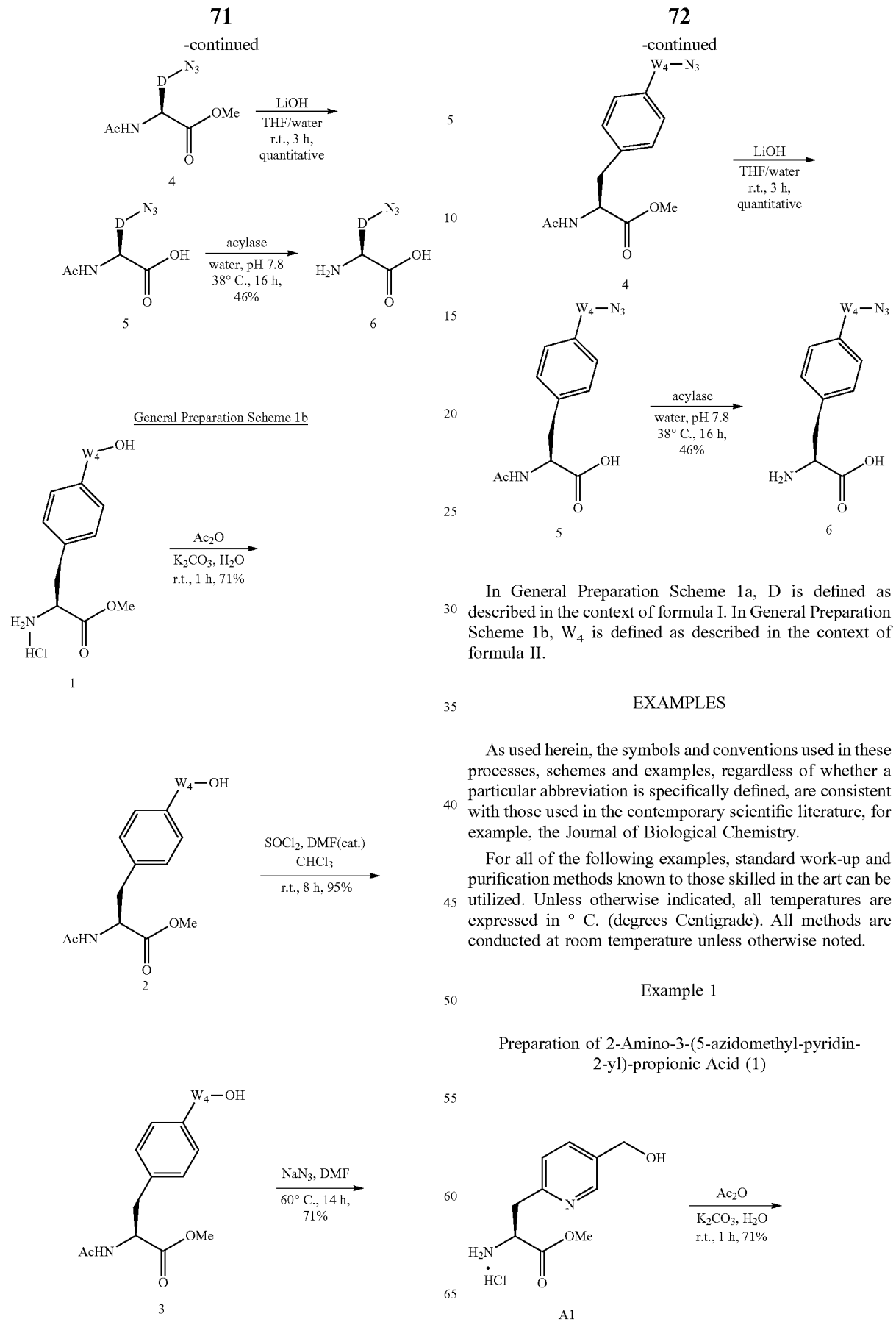

In General Preparation Scheme 1a, D is defined as described in the context of formula I. In General Preparation Scheme 1b, $W_4$ is defined as described in the context of formula II.

EXAMPLES

As used herein, the symbols and conventions used in these processes, schemes and examples, regardless of whether a particular abbreviation is specifically defined, are consistent with those used in the contemporary scientific literature, for example, the Journal of Biological Chemistry.

For all of the following examples, standard work-up and purification methods known to those skilled in the art can be utilized. Unless otherwise indicated, all temperatures are expressed in ° C. (degrees Centigrade). All methods are conducted at room temperature unless otherwise noted.

Example 1

Preparation of 2-Amino-3-(5-azidomethyl-pyridin-2-yl)-propionic Acid (1)

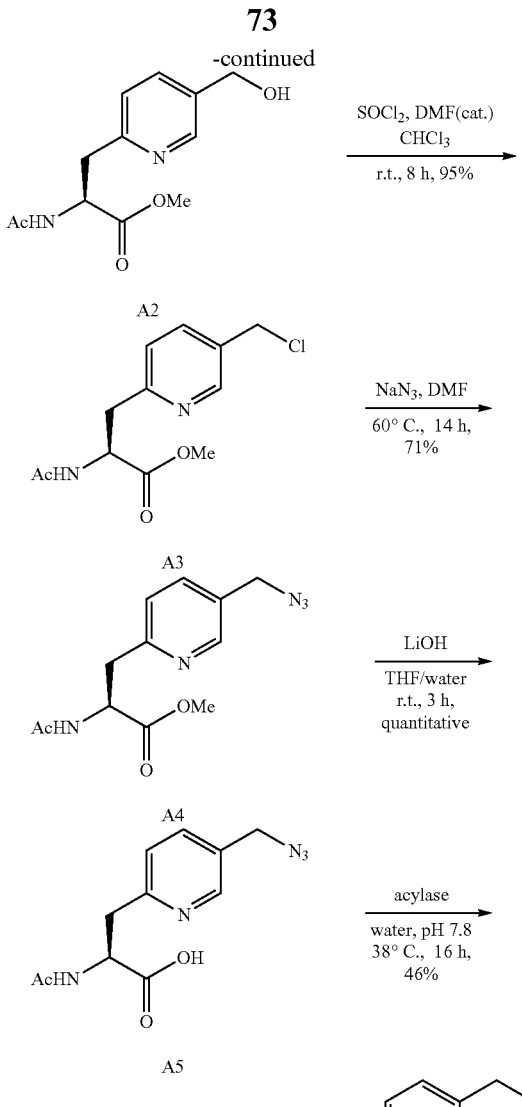

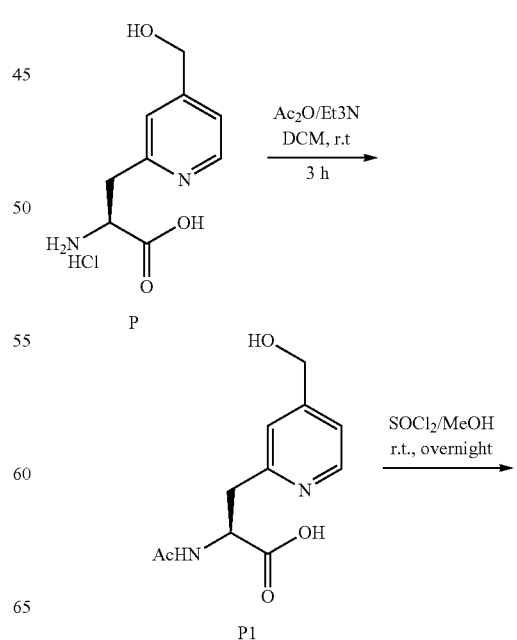

h. The reaction mixture was diluted with CHCl₃ (50 mL), and then washed with saturated NaHCO₃. The aqueous layer was extracted with CHCl₃ twice. The combined organic layers were dried over MgSO₄. The crude product A3 (0.74 g, 95%) was directly used for next reaction. LCMS m/z: 271 (M+1).

Preparation of Compound A4

A mixture of the chloride A3 (1.33 g, 4.9 mmol, 1 eq), NaN₃ (0.64 g, 9.8 mmol, 2 eq) and NaI (73 mg, 0.49 mmol, 0.1 eq) in DMF (20 mL) was stirred at 60° C. for 15 h. The reaction mixture was then concentrated to dryness. The crude product was purified by FCC (EA) to afford the azido-product A4 (0.95 g, 71%). LCMS m/z: 278 (M+1).

Preparation of Compound A5

A mixture of the methyl ester A4 (0.95 g, 3.4 mmol, 1 eq) and LiOH—H₂O (0.29 g, 6.8 mmol, 2 eq) in THF/water (6 mL/3 mL) was stirred at room temperature for 3 h. The reaction mixture was neutralized to pH 7 with 1 N HCl, and then concentrated to dryness. The crude product A5 (~0.91 g, quantitative) was directly used for next reaction. LCMS m/z: 264 (M+1), 262 (M−1).

Preparation of Compound (1)

Acylase I (100 mg, Sigma, A3010, Grade I) was added into a solution of acetamide A5 (0.91 g, 3.4 mmol) in water (60 mL). After pH of the solution was adjusted to 7.8 with 1 N aqueous lithium hydroxide solution. The reaction mixture was stirred at 38° C. for 16 h. Active carbon (2 g) was added and the solution was stirred for 10 min. The mixture was filtered through a pad of Celite. The filtrate was concentrated to around 20 mL, which was directly used for purification by HPLC. Fractions containing pure product (1) were combined and concentrated to dryness. The final sample was dried by lyophilization to afford amino-acid (1) (0.35 g, 46%) as white powder. LCMS m/z: 222 (M+1), 220 (M−1). ¹H NMR (300 MHz, D₂O) δ 8.36 (s, 1H), 7.71 (d, J=7.5 Hz, 1H), 7.26 (d, J=7.5 Hz, 1H), 4.36 (s, 2H), 3.98 (dt, J=2.7 and 6.5 Hz, 1H), 3.32-3.16 (m, 2H).

Example 2

Preparation of Compound (3)

Preparation of Compound A2

Acetic anhydride (0.42 mL, 4.5 mmol, 1.1 eq) was slowly added a solution of A1 (HCl salt, 1.0 g, 4.1 mmol, 1 eq) and K₂CO₃ (1.18 g, 8.6 mmol, 2.1 eq) in water (20 mL) at room temperature. The reaction mixture was stirred at room temperature for 1 h. The water was removed on a rotovapor, and the residue was treated with methanol. The solid was removed by filtration. The methanol solution was concentrated and the residue was purified by FCC (MeOH/DCM=1/10) to provide acetamide A2 (0.73 g, 71%) as a white solid. LCMS m/z: 253 (M+1).

Preparation of Compound A3

Thionyl chloride (0.32 mL, 4.3 mmol, 1.5 eq) was slowly added into a solution of the acetamide A2 (0.73 g, 2.9 mmol, 1 eq) and DMF (22 µL, 0.29 mmol) in CHCl₃ (25 mL) at room temperature. After 4 h, additional SOCl₂ (80 µL, 1.1 mmol) was added and the mixture was stirred for another 4

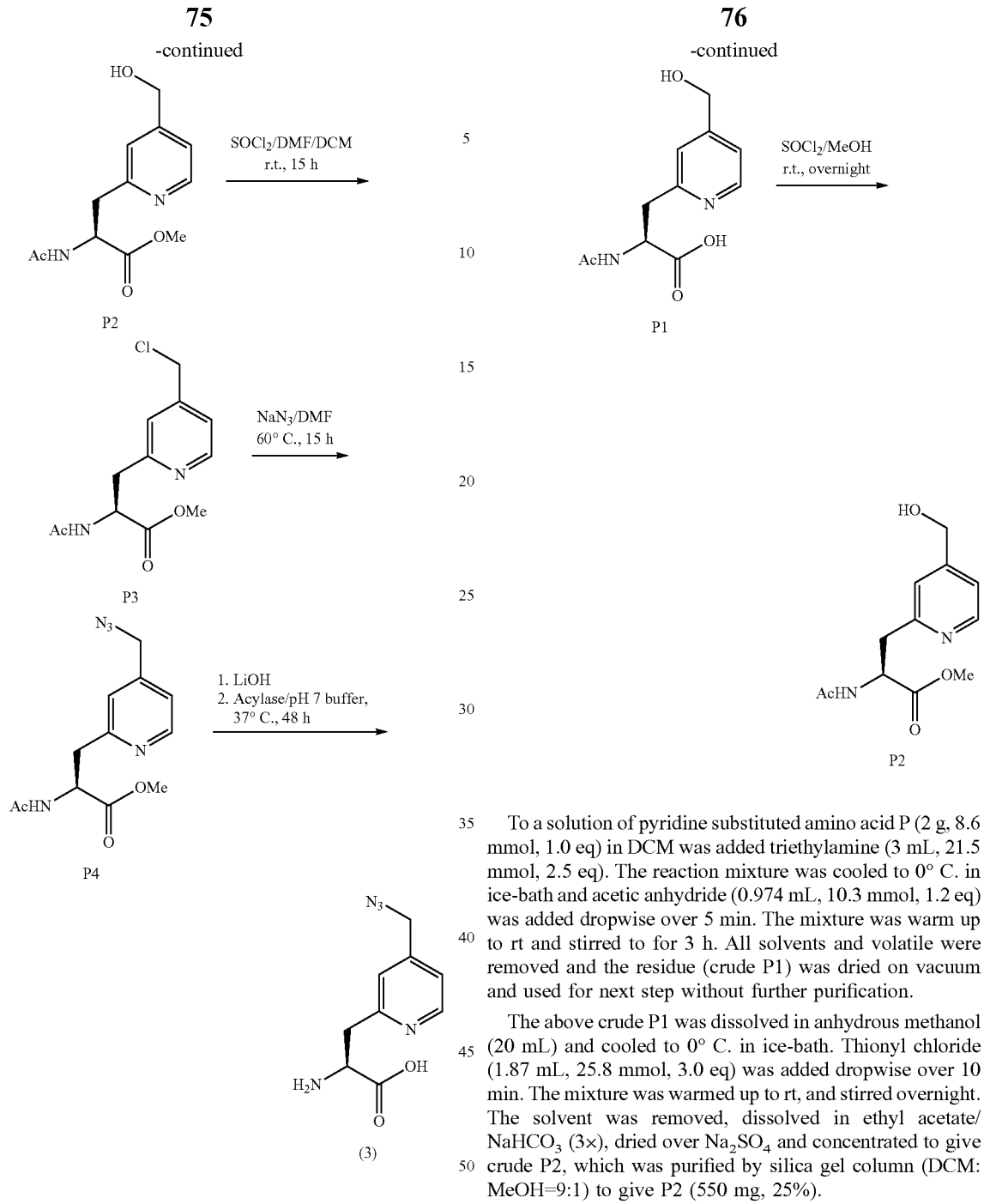

General Procedure for Preparation of Compound (3)

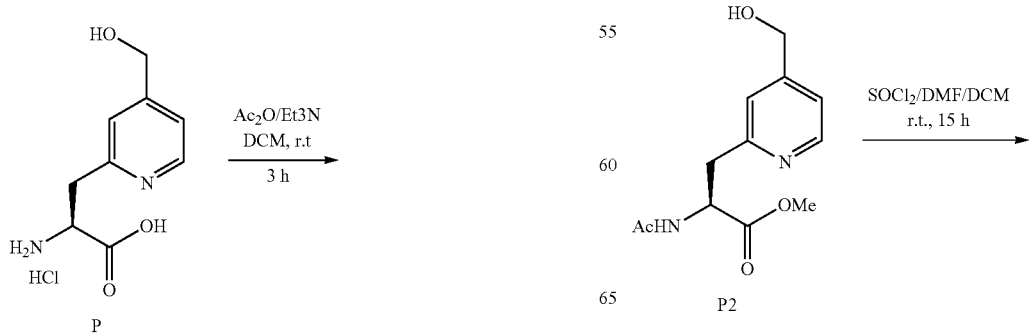

To a solution of pyridine substituted amino acid P (2 g, 8.6 mmol, 1.0 eq) in DCM was added triethylamine (3 mL, 21.5 mmol, 2.5 eq). The reaction mixture was cooled to 0° C. in ice-bath and acetic anhydride (0.974 mL, 10.3 mmol, 1.2 eq) was added dropwise over 5 min. The mixture was warm up to rt and stirred to for 3 h. All solvents and volatile were removed and the residue (crude P1) was dried on vacuum and used for next step without further purification.

The above crude P1 was dissolved in anhydrous methanol (20 mL) and cooled to 0° C. in ice-bath. Thionyl chloride (1.87 mL, 25.8 mmol, 3.0 eq) was added dropwise over 10 min. The mixture was warmed up to rt, and stirred overnight. The solvent was removed, dissolved in ethyl acetate/ NaHCO$_3$ (3×), dried over Na$_2$SO$_4$ and concentrated to give crude P2, which was purified by silica gel column (DCM: MeOH=9:1) to give P2 (550 mg, 25%).

-continued

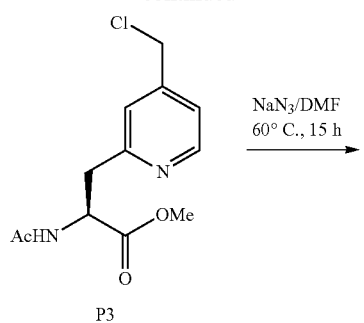

P3

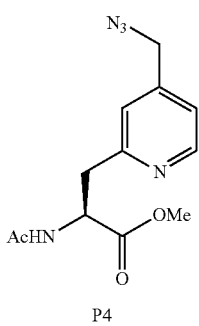

P4

To a solution of P2 (550 mg, 2.18 mmol, 1.0 eq) in chloroform (10 mL) was added 2 drops of DMF. The reaction mixture was cooled to 0° C. in ice-bath and thionyl chloride (634 μL, 8.72 mmol, 4 eq) was added dropwise over 5 min. The mixture was warmed to rt and stirred overnight. The reaction was worked up with DCM/NaHCO$_3$. The organic layer was dried over Na$_2$SO$_4$ and purified by silica gel column (DCM:MeOH=9:1) to give product P3 (450 mg, 76%).

To a solution of P3 (450 mg, 1.67 mmol, 1.0 eq) in DMF (10 mL) was added NaN$_3$ (217 mg, 3.34 mmol, 2.0 eq) and NaI (25 mg, 0.167 mmol, 0.1 eq). The reaction mixture was heated at 60° C. overnight. The reaction was worked up with DCM/NaHCO$_3$. The organic layer was dried over Na$_2$SO$_4$ and purified by prep HPLC to give product P4 (400 mg, 86%).

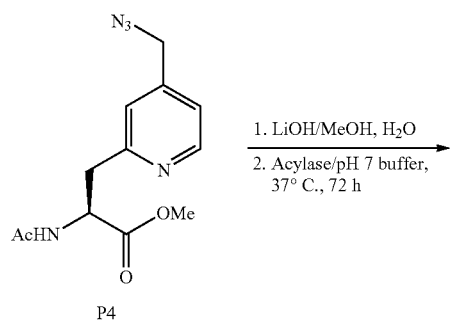

P4

-continued

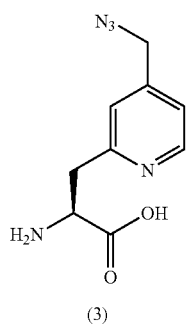

(3)

To the solution of P4 (400 mg, 1.44 mmol, 1.0 eq) in MeOH (5 mL) was added LiOH (303 mg, 7.2 mmol, 5 eq, in 5 mL of H$_2$O). The reaction stirred at rt for 2 h. The solvent was removed and the residue directly used for next step without further purification.

To a solution of the above residue in small amount of DMSO and 50 mM NaH$_2$PO$_4$—Na$_2$HPO$_4$ buffer (20 mL) was added Acylase (100 mg) in 5 mL buffer. The mixture was heated to 37° C. for 72 h. Charcoal (200 mg) was added into the reaction and stirred at rt for 10 min, filtered through a pad of Celite. The filtrate was concentrated and purified by prep-HPLC to give product (3) (85 mg) as HCl salt. LC-MS (ESI): 222 (M+1), 220 (M−1). $^1$HNMR (300 MHz, CD$_3$OD) δ 8.50 (d, J=4.8 Hz, 1H), 8.17 (s, 1H), 7.33 (s, 1H), 7.27 (d, J=5.4 Hz, 1H), 4.49 (s, 2H), 4.03 (m, 1H), 3.42 (dd, 1H, J=3.6 and 12.0 Hz, 1H), 3.27 (m, 2H).

Example 3

Preparation of Compound (2)

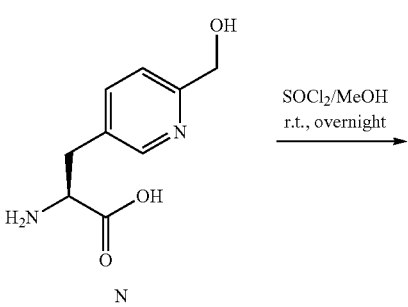

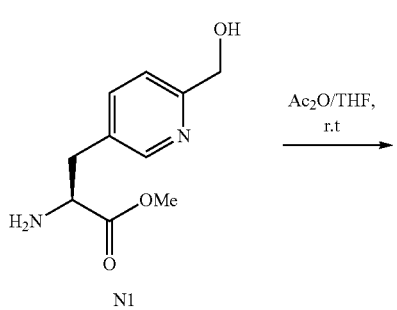

N1

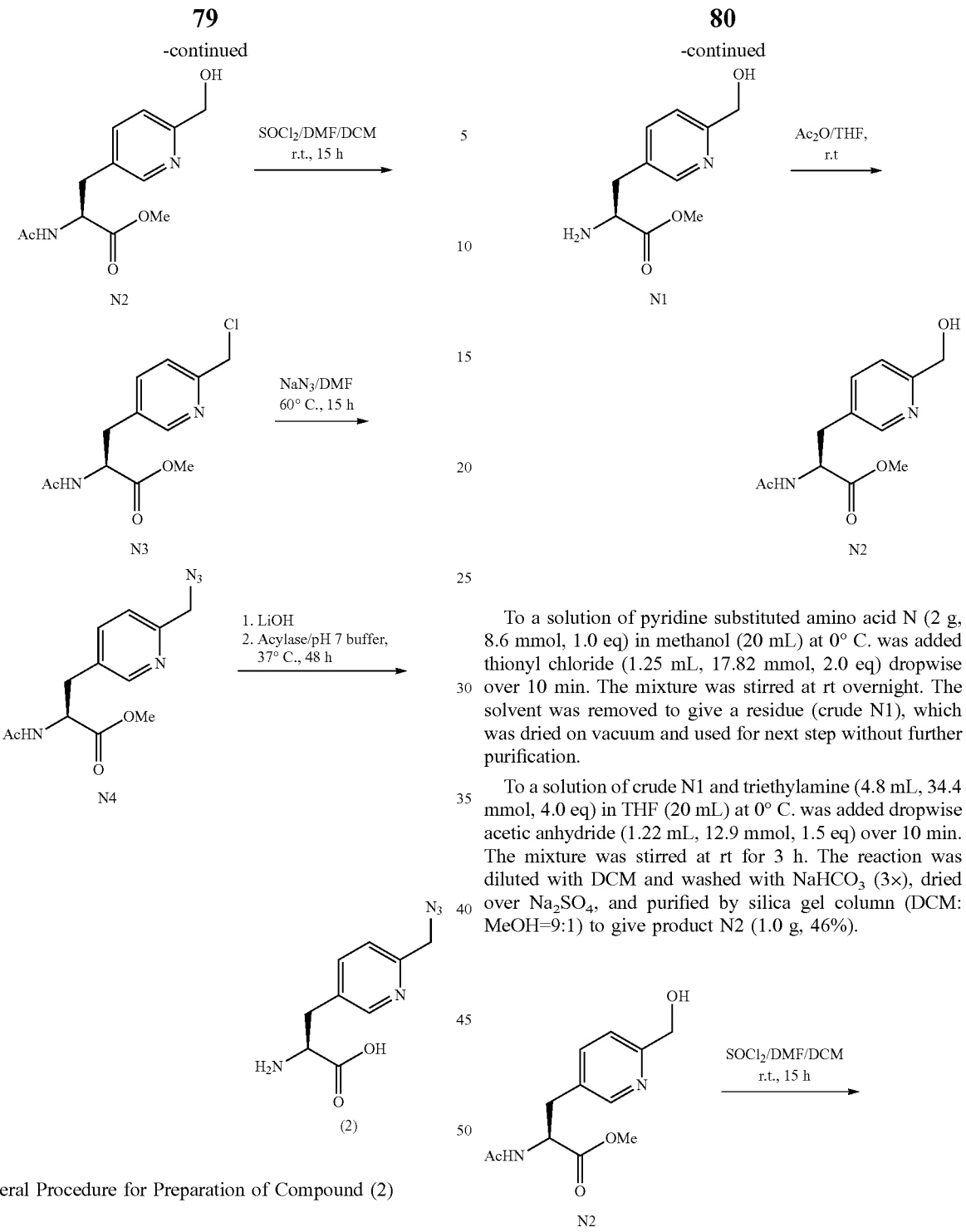

General Procedure for Preparation of Compound (2)

To a solution of pyridine substituted amino acid N (2 g, 8.6 mmol, 1.0 eq) in methanol (20 mL) at 0° C. was added thionyl chloride (1.25 mL, 17.82 mmol, 2.0 eq) dropwise over 10 min. The mixture was stirred at rt overnight. The solvent was removed to give a residue (crude N1), which was dried on vacuum and used for next step without further purification.

To a solution of crude N1 and triethylamine (4.8 mL, 34.4 mmol, 4.0 eq) in THF (20 mL) at 0° C. was added dropwise acetic anhydride (1.22 mL, 12.9 mmol, 1.5 eq) over 10 min. The mixture was stirred at rt for 3 h. The reaction was diluted with DCM and washed with NaHCO₃ (3×), dried over Na₂SO₄, and purified by silica gel column (DCM:MeOH=9:1) to give product N2 (1.0 g, 46%).

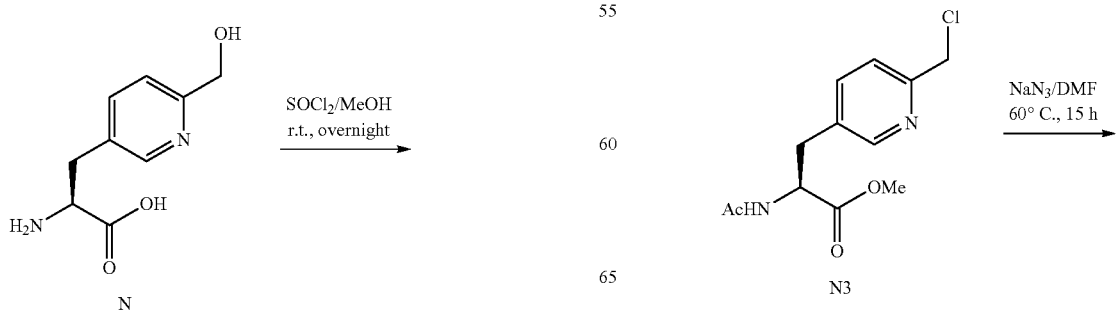

-continued

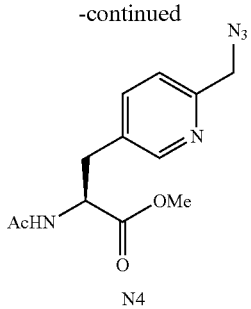
N4

To a solution of N2 (2 g, 7.94 mmol, 1.0 eq) in chloroform (20 mL) was added 4 drops of DMF. The reaction mixture was cooled to 0° C. in ice-bath and thionyl chloride (2.3 mL, 31.76 mmol, 4 eq) was added dropwise over 10 min. The mixture was stirred at rt overnight. The reaction was worked up with DCM/NaHCO$_3$. The organic layer was dried over Na$_2$SO$_4$ and purified by silica gel column (DCM:MeOH=9:1) to give product N3 (1 g, 47%).

To a solution of N3 (1 g, 3.7 mmol, 1.0 eq) in DMF (20 mL) was added NaN$_3$ (481 mg, 7.4 mmol, 2.0 eq) and NaI (55.5 mg, 0.37 mmol, 0.1 eq). The reaction mixture was heated at 60° C. in an oil-bath overnight. The reaction was diluted with DCM. The organic layer was washed with NaHCO$_3$, dried over Na$_2$SO$_4$ and purified by silica gel column (DCM:MeOH=9:1) to give product N4 (1.8 g, 98%) as yellow oil.

To a solution of N4 (1 g, 3.6 mmol, 1.0 eq) in MeOH (20 mL) was added LiOH (757 mg, 18 mmol, 5 eq, in 10 mL of water). The reaction stirred at r.t. for 2 h. The solvent was removed and the residue was directly used for next step without further purification.

To a solution of the above residue in small DMSO and 50 mM NaH$_2$PO$_4$—Na$_2$HPO$_4$ buffer (100 mL was added Acylase (100 mg). The mixture was heated to 37° C. for 48 h. Charcoal (200 mg) was added into the reaction mixture, and stirred at rt for 10 min, filtered on Celite. The filtrate was concentrated and recrystallized from MeOH to give product (2) (1.3 g). LC-MS (ESI): 222 (M+1), 220 (M−1). $^1$HNMR (300 MHz, DMSO-d6) δ 8.44 (s, 1H), 7.76 (d, J=7.8 Hz, 1H), 7.33 (d, J=7.8 Hz, 1H), 4.44 (s, 2H), 3.45 (m, 1H), 2.98-3.12 (m, 2H), 3.27 (m, 2H).

Example 4

Preparation of Compound (30)

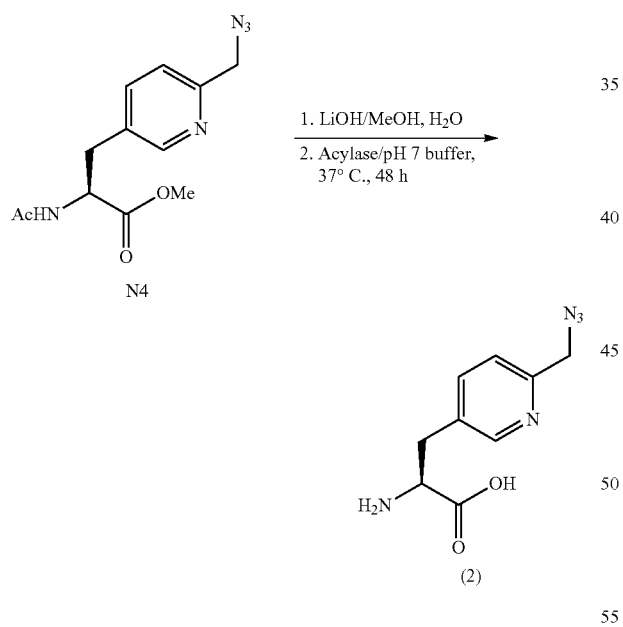

General Procedure for Preparation of Compound (30)

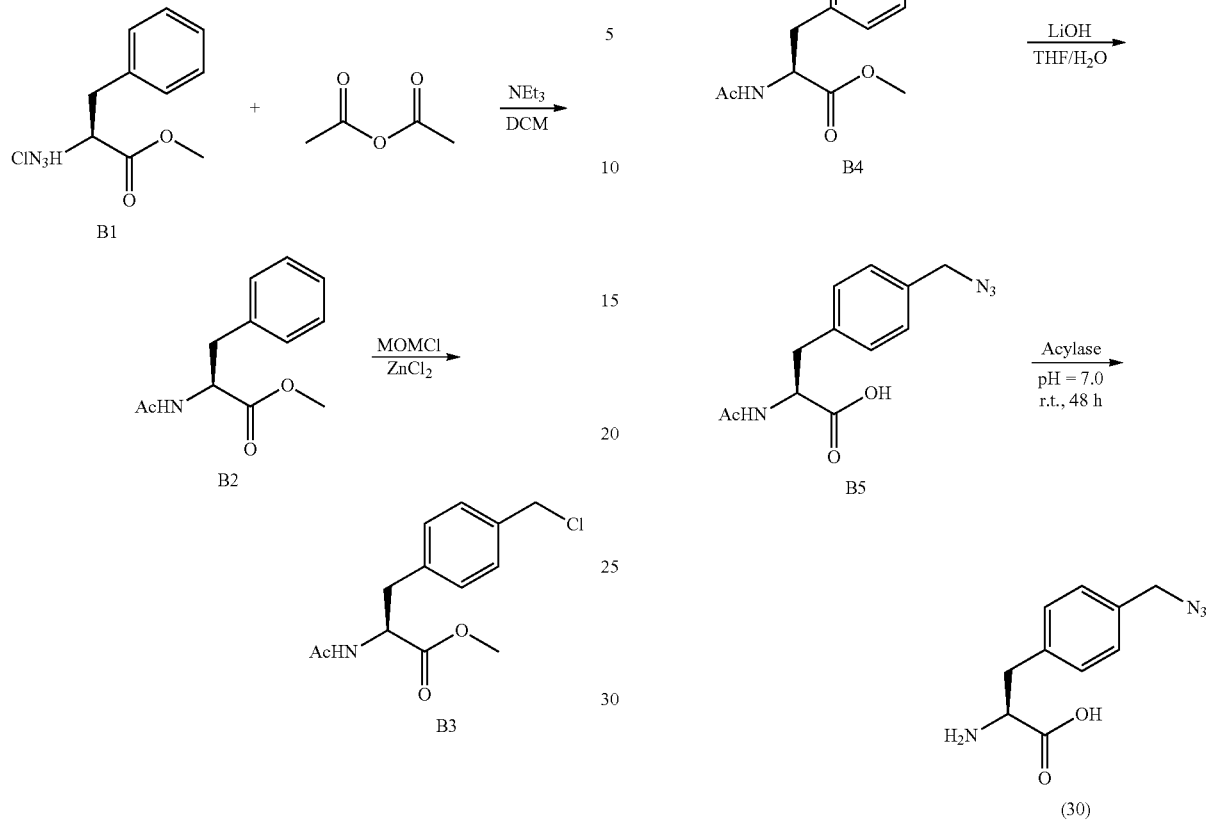

To a solution of the Phe methyl ester B1 (50 g, 232 mmol, 1.0 eq) in DCM (300 mL) was added triethylamine (81 mL, 580 mmol, 2.5 eq) at 0° C. was added acetic anhydride (33 mL, 348 mmol, 1.5 eq) dropwise over 15 min. The mixture was stirred at rt for 3 h. The reaction was washed with NaHCO$_3$ (2×), dried over Na$_2$SO$_4$ and purified by silica gel column (DCM:MeOH=9:1) to give product B2 (50 g, 97%) as white solid.

A mixture of ester B2 (52 g, 0.235 mole, 1.0 eq), MOM-Cl (136 mL, 1.79 mole, 7.6 eq) and ZnCl2 (128 g, 0.94 mole, 4.0 eq) was stirred at 6-8° C. for 8 h. After removing the volatile on rotavapor at 6-8° C., the residue was poured into ice-water and extracted with ethyl acetate (3×). The combined organic layers were washed with NaHCO$_3$ and dried over Na$_2$SO$_4$, and concentrated to a small volume. Ether (50 mL) was then added. The ether solution was kept in a −20° C. fridge overnight. The crystallized product was filtered and dried in vacuum to give product B3 (31 g, 49%) as white solid.

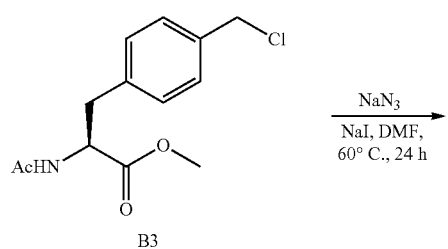

To a solution of B3 (20 g, 74.2 mmol, 1.0 eq) in DMF (100 mL) was added NaN$_3$ (9.64 g, 148 mmol, 2.0 eq) and NaI (1.11 g, 7.42 mmol, 0.1 eq). The reaction mixture was heated at 60° C. in an oil-bath overnight. Solvent DMF was removed on a rotavapor, and the reaction mixture was dissolved in ethyl acetate, and washed with NaHCO$_3$ (3×), dried over Na$_2$SO$_4$, and purified by silica gel column (DCM:MeOH=9:1) to give product B4 (20.5 g, 100%) as yellow oil.

To a solution of B4 (20 g, 724 mmol, 1.0 eq) in a mixed solution of THF:MeOH:H2O (50 mL:50 mL:20 mL) was added LiOH—H$_2$O (6.94 g, 144.8 mmol, 2 eq). The reaction was stirred at rt for 2 h. Solvent was removed to give a residue, which was worked up with ethyl acetate. The organic layer was washed with 1N HCl (3×), dried over Na$_2$SO$_4$ and concentrated to give product B5 (18.3 g, 96%) as yellow oil.

To a solution of above amide B5 (18 g, 68.7 mmol) in DMSO (20 mL) and 50 mM NaH$_2$PO$_4$—Na$_2$HPO$_4$ buffer (1.8 L) was added acylase (1 g). the solution was heated at 37° C. for 48 h. Charcoal (20 g) was added into the reaction mixture, and stirred at rt for 10 min, filtered through Celite. The filtrate was washed with ethyl acetate. The aqueous layer was concentrated to a small volume, and product was precipitated out as white solid. The solid was filtered and dried in vacuo to give product (30) (10 g, 66%) as white solid. LC-MS (ESI): 221 (M+1). $^1$HNMR (300 MHz, DMSO-d6) δ 7.27 (br s, 4H), 4.37 (s, 2H), 3.43 (m, 2H), 3.17 (m, 1H), 2.84 (m, 1H).

Example 5

Preparation of Compound (40)

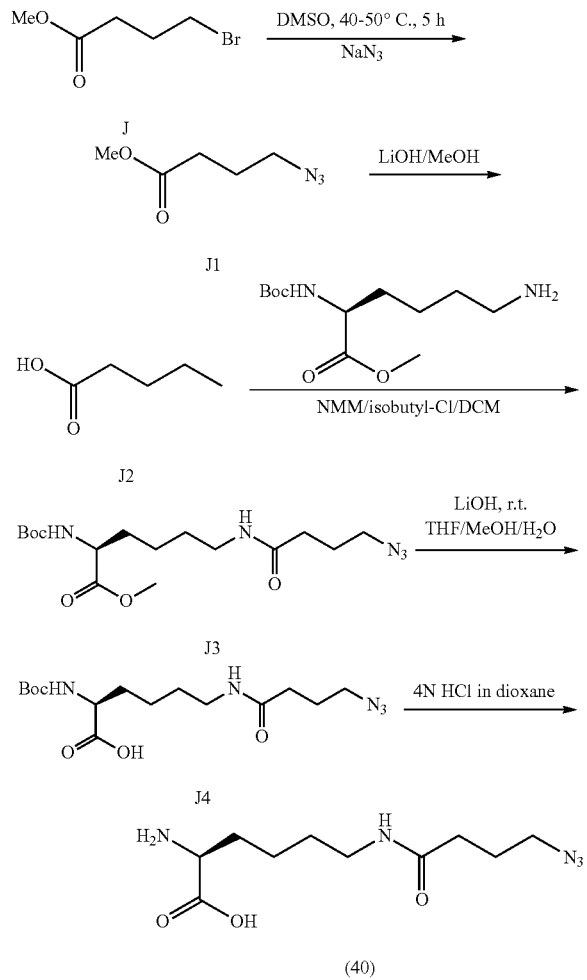

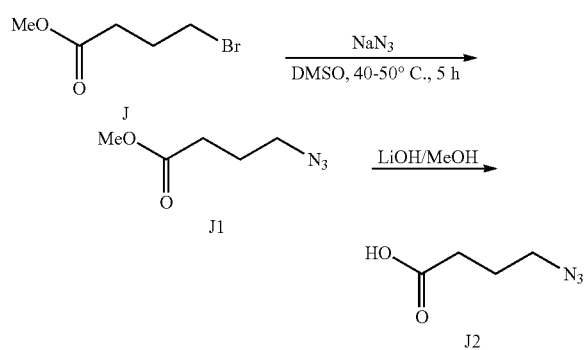

Genera Procedure for Preparation of Compound (40)

To a solution of J (10 g, 55.2 mmol, 1.0 eq) in DMSO (100 mL) was added sodium azide (5.4 g, 82.8 mmol, 1.5 eq) in several portions with stirring. The mixture was heated at 40-50° C. for 5 h. After being cooled to rt, the mixture was diluted with water (200 mL), and extracted with ether (3×). The combined organic layer was washed with brine, dried over $Na_2SO_4$ and concentrated to give product J1 (7.8 g, 98.7%) as oil.

The above product J1 (7.8 g, 54.5 mmol) was suspended in a mixture of LiOH (11.4 g, 274 mmol, 5.0 eq) in water (100 mL) and MeOH (20 mL). The mixture was allowed to stirring at rt for 1 h diluted with water (200 mL), and extracted with ether (3×). The aqueous layer was acidified with 1N HCl to pH 2, and extracted with ether (3×). The combined organic layers were dried over $Na_2SO_4$ and concentrated to give product J2 (7 g, 100%) as oil.

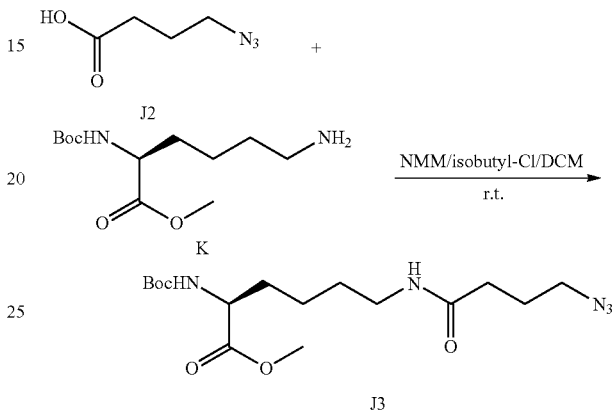

To a solution of J2 (500 mg, 3.88 mmol, 1.0 eq) in DCM at 0° C. was added N-methyl morpholine (NMM, 510 μL, 4.65 mmol, 1.2 eq) and isobutyl chloroformate (607 μL, 4.65 mmol, 1.2 eq). The mixture was stirred at rt for 2 h. To above solution was added Boc-Lys methyl ester (1.15 g, 3.88 mmol, 1.0 eq). The mixture was stirred at rt for 3 h, quenched with water. The reaction was extracted with DCM (3×). The organic layer was washed with brine and dried over $Na_2SO_4$ and then concentrated to give product J3 (900 mg, 63%) as oil.

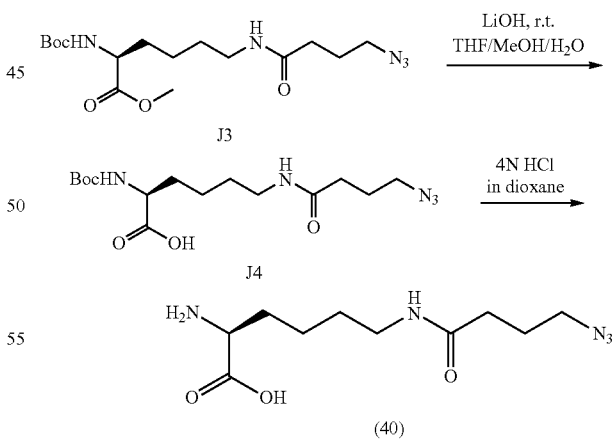

To a solution of J3 (900 mg, 2.42 mmol, 1.0 eq) in a mixture of THF:MeOH:$H_2O$ (5 mL:3 mL:2 mL) was added LiOH (508 mg, 12.1 mmol, 5.0 eq). The mixture allowed to stir at rt for 1 h, concentrated to dryness to give crude sodium salt J4.

The crude J4 was treated with 4N HCl in dioxane (10 mL) and stirred at rt for 1 h, concentrated to give crude product (40), which was purified by prep HPLC to give pure (40) (332 mg, 53%) as white solid. LC-MS (ESI): 258 (M+1), 256 (M−1). $^1$HNMR (300 MHz, D$_2$O) δ 3.52 (t, J=6.9 Hz, 1H), 3.15 (t, J=6.6 Hz, 2H), 2.99 (t, J=6.9 Hz, 2H), 2.12 (t, J=7.5 Hz, 2H), 1.66 (m, 4H), 1.35 (m, 2H), 1.18 (m, 2H).

Example 6

Assessment of Reactivity of Compounds (30) and (40)

This example provides an assessment of the reaction rate of compounds (30) and (40) as compared to a reference compound, p-azido-phenylalanine (50).

DBCO analog (60), was dissolved in acetonitrile to a concentration of 60 µM. Amino acid analogs (30), (40), and (50) were serially diluted in PBS buffer in the wells of a 96-well microtiter plate to a volume of 180 µL. 20 µL of DBCO analog stock solution was added to each well and the kinetics of the loss of DBCO to form the addition adduct was monitored at 310 nm by absorbance using a SpectraMax plate reader at 25° C. A schematic of the reaction of compounds (30), (40), and (50) with compound (60) is shown as FIG. 1. The kinetics accurately fit a first order decay with $A_{310}=A_0*(1-\exp(-k_{obs}*t))$, where $k_{obs}$ is the pseudo first order rate constant with units of sec$^{-1}$ under conditions where [Azide compound]>>[DBCO]. A plot of $k_{obs}$ vs. [Azide] yields the second-order rate constant (units of M$^{-1}$ sec$^{-1}$) for each amino acid, a measure of the intrinsic chemical reactivity of each amino acid.

Figure 2:
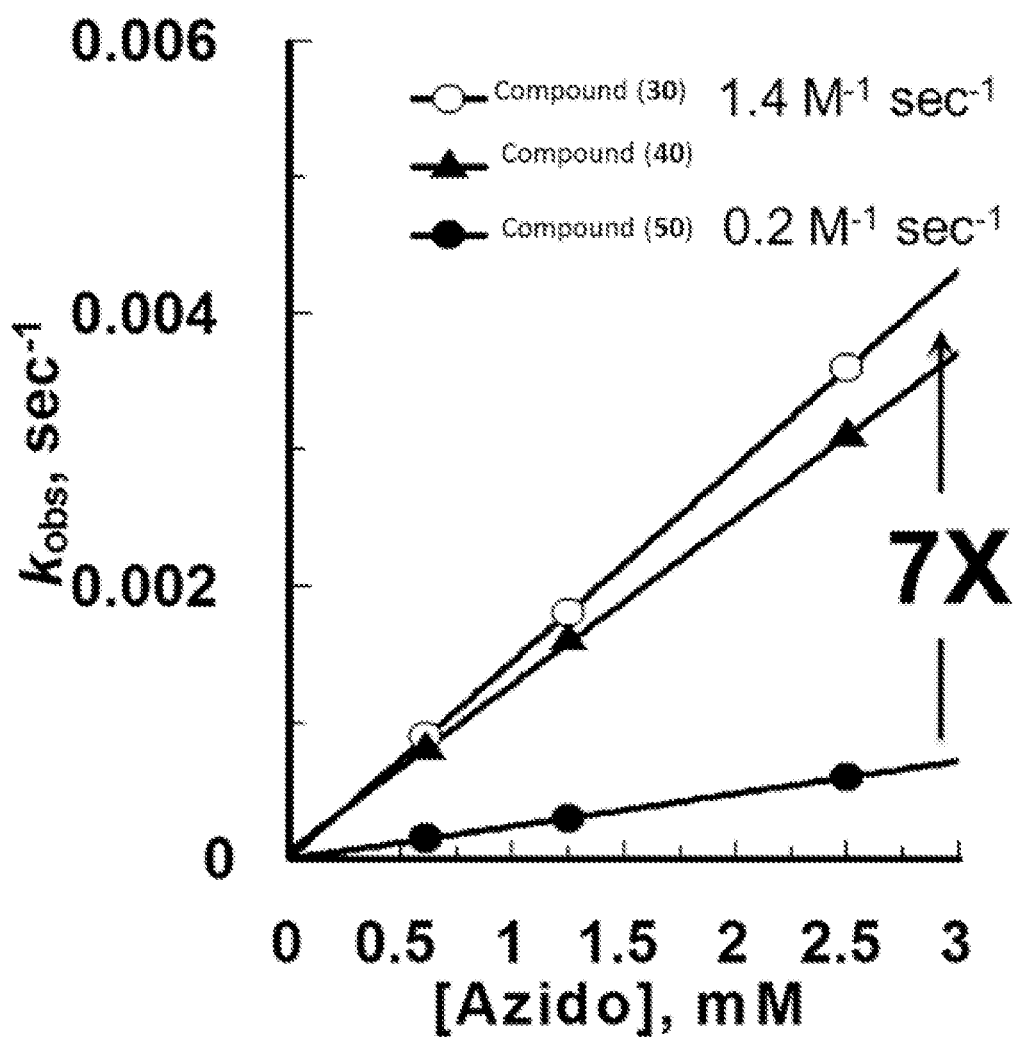
FIG. 2 provides a plot of $k_{obs}$ vs. [Azide] for reaction of compound (30), compound (40) and compound (50) with compound (60).

The results of the experiment are shown as FIG. 2. Surprisingly, compounds (30) and (40) exhibited a first order rate constant of 1.4 M$^{-1}$ sec$^{-1}$, approximately 7-fold higher than first order rate constant of 0.2 M$^{-1}$ sec$^{-1}$ for compound (50). Similar experiments were performed to assess the reactivity of compounds (1), (2), and (3); the reaction of compounds (1), (2), and (3) was greater than 90% complete in 30 minutes and complete in less than 2 hours, suggesting that compounds (1), (2), and (3) exhibit rate constants similar to those of compounds (30) and (40).

Example 7

Incorporation of Compound (30) into an Exemplary Polypeptide, GFP

This example describes incorporation of compound (30) into green fluorescent protein. To monitor synthesis of GFP, the DNA encoding turboGFP containing an amber codon (stop codon) before the chromophore was cloned into OCFS expression vector pYD317. The stop codon (TAG) was inserted by overlapping PCR mutagenesis at the nucleotides corresponding to the amino acid tyrosine at the 50$^{th}$ amino acid according to the crystal structure of turboGFP (pdb 2G6X). Previous studies of this site demonstrated that non-aromatic substitutions at this position resulted in an absence of fluorescence and that suppression with an aromatic nnAA at the stop codon will result in fluorescence.

Figure 3:
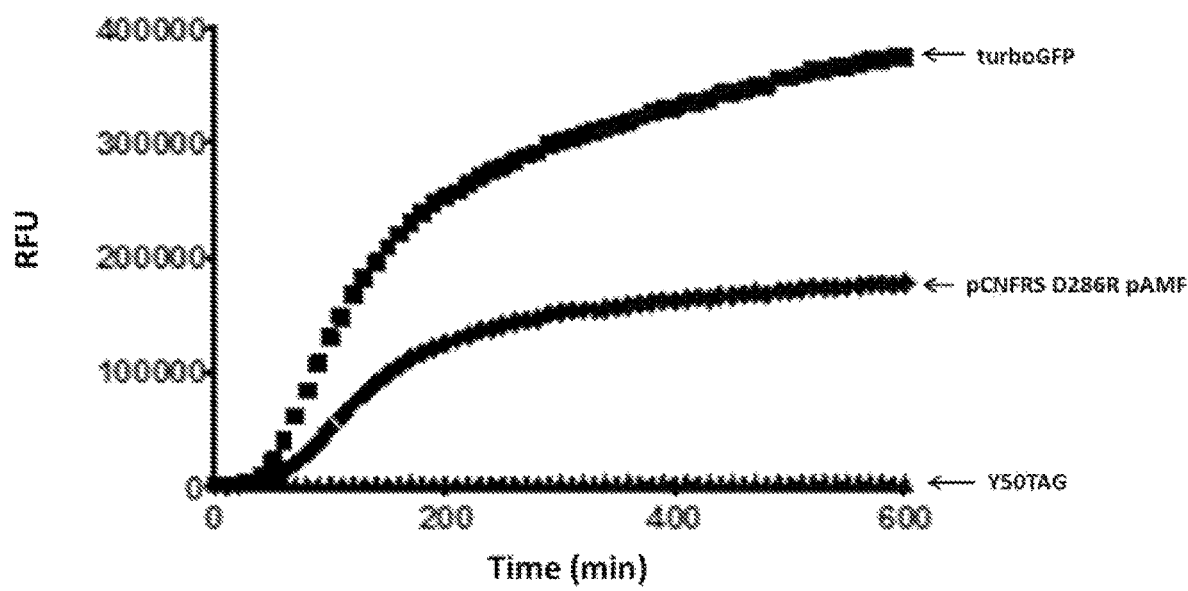
FIG. 3 provides a plot of a time course for pAMF incorporation at the Y50TAG site in GFP.

Reactions were incubated at 30° C. in a spectrophotometer (Molecular Devices, SpectraMaxM5) for five hours with an adhesive cover (VWR, 9503130) and fluorescence intensity measured at 10-minute intervals, $\lambda_{Ex}$=476 nm and $\lambda_{Em}$=51. OCFS reaction mix was immediately added to microplate for a 30 µL final reaction volume containing 30% S30 extract, 24 µg/mL T7 RNA polymerase, 1 mM L-tyrosine (Sigma, T8566), pre-mix*, 10 µM tRNA, 5 µM pCN-FRS D286R, 1 mM compound (30), and 3 nM turboGFP plasmid (Evrogen, Russia, subcloned into a PYD317 vector) in DEPC-treated water (G Biosciences, 786-109). A positive control reaction using turboGFP without the stop codon was used to ensure that the reactions proceeded with rates similar previously observed, while reactions containing turboGFP Y50TAG were also run without tRNA to ensure no fluorescence was detected (negative control) in the absence of the system responsible for incorporation of pAMF. Incorporation of pAMF into GFP achieves relatively high yields of protein in a site-specific manner. FIG. 3 shows a time course for pAMF incorporation at the Y50TAG site in GFP.

Example 8

Incorporation of Compound (30) into an Exemplary Polypeptide, GM-CSF

DNA encoding human GMCSF with amber codon was cloned into expression vector pYD317. The TAG codon was inserted by overlapping PCR mutagenesis at the nucleotides corresponding to the amino acid serine at the position 6.

Cell-free extracts containing tRNA CUA were thawed to room temperature and incubated with 50 µM iodoacetamide for 30 min. Cell-free reactions were run at 30 C for up to 10 h containing 30% (v/v) iodoacetamide-treated extract with 8 mM magnesium glutamate, 10 mM ammonium glutamate, 130 mM potassium glutamate, 35 mM sodium pyruvate, 1.2 mM AMP, 0.86 mM each of GMP, UMP, and CMP, 2 mM amino acids for all 18 amino acids except tyrosine and phenylalanine which were added at 0.5 mM, 4 mM sodium oxalate, 1 mM putrescine, 1.5 mM spermidine, 15 mM potassium phosphate, 100 nM T7 RNAP, 1.3 µM E. coli DsbC, 2 mM oxidized (GSSG) glutathione, 1 µM tRNA synthetase, and 1 mM compound (30). The concentrations of GMCSF TAG variant plasmid was 5 µg/mL. To label synthesized protein with 14C, 3.33% (v/v) 1-[U-14C]-leucine (300 mCi/mmole; GE Life Sciences, Piscataway, NJ) was added to reaction as well.

For reducing gel, 4 µL of sample, 1 µL of 1 M DTT, 7 µL of DI H$_2$O and 4 µL of 4×LDS buffer (Invitrogen, Carlsbad, CA) were mixed and heated in hot blot at 70 C for 5 minutes. Samples were analyzed by 4~12% Bis-Tris SDS-PAGE gels (Invitrogen, Carlsbad, CA) according to the manufacturer's recommendations. Gels were dried and analyzed by autoradiography using a Storm 840 PhosphoImager after about 16 hours exposure.

Autoradiography demonstrated that intact full length GMCSF containing compound (30) was made.

Example 9

Incorporation of Compound (30) into an Exemplary Polypeptide, IgG

To demonstrate the feasibility of incorporation of compound (30) into IgG, DNA encoding trastuzumab heavy chain containing an amber codon and DNA encoding trastuzumab light chain were cloned into expression vector pYD317. TAG codon was inserted by overlapping PCR mutagenesis at the nucleotides corresponding to the amino acid serine at the position 136 by EU index in CHI domain.

Cell-free extracts were thawed to room temperature and incubated with 50 µM iodoacetamide for 30 min. Cell-free reactions were run at 30 C for up to 10 h containing 30% (v/v) iodoacetamide-treated extract with 8 mM magnesium glutamate, 10 mM ammonium glutamate, 130 mM potassium glutamate, 35 mM sodium pyruvate, 1.2 mM AMP, 0.86 mM each of GMP, UMP, and CMP, 2 mM amino acids for all 18 amino acids except tyrosine and phenylalanine which were added at 0.5 mM, 4 mM sodium oxalate, 1 mM putrescine, 1.5 mM spermidine, 15 mM potassium phosphate, 100 nM T7 RNAP, 1.3 µM E. coli DsbC, 5 µM yeast PDI, 2 mM oxidized (GSSG) glutathione, 15 µM tRNA, 1 µM tRNA synthetase, and 1 mM compound (30). The concentrations of heavy chain TAG variant plasmid and wild type light chain plasmid were 7.5 µg/mL and 2.5 µg/mL respectively. To label synthesized protein with 14C, 3.33% (v/v) 1-[U-14C]-leucine (300 mCi/mmole; GE Life Sciences, Piscataway, NJ) was added to reaction as well.

For non reducing gel, 4 µL of sample, 8 µL of DI H$_2$O and 4 µL of 4×LDS buffer (Invitrogen, Carlsbad, CA) were mixed before being loaded on gel. For reducing gel, 4 µL of sample, 1 µL of 1 M DTT, 7 µL of DI H$_2$O and 4 µL of 4×LDS buffer (Invitrogen, Carlsbad, CA) were mixed and heated in hot blot at 70 C for 5 minutes. Samples were analyzed by 4~12% Bis-Tris SDS-PAGE gels (Invitrogen, Carlsbad, CA) according to the manufacturer's recommendations. Gels were dried and analyzed by autoradiography using a Storm 840 PhosphoImager after about 16 hours exposure.

Autoradiography demonstrated that the intact full length IgG containing compound (30) was made.

Example 10

Assessment of Reactivity of Compounds (30), (1) and (2)

This example provides an assessment of the reaction rate of compounds (30), (1) and (2) with DBCO-NH$_2$ (61) (shown below).

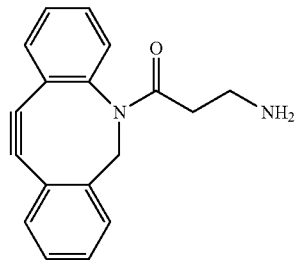

(61)

DBCO-NH$_2$ (61) was dissolved in pH 7.4 phosphate buffered saline to yield a 500 M solution. Amino acid analogs (30), (1), and (2) were dissolved in the same buffer to yield 5 mM clear solutions, and then diluted to a concentration of 500 µM using the same buffer. One hundred microliters of each amino acid analog was mixed with 100 µL of compound (61) and vortexed. The absorption of compound (61) was monitored at 310 nm using a NANODROP 1000 UV Spectrometer. Measurements were obtained at 0, 0.5, 2, 6, and 20 hours. The reduction in the absorption of compound (61) is indicative of its reaction with the amino acid analogs.

Figure 4:
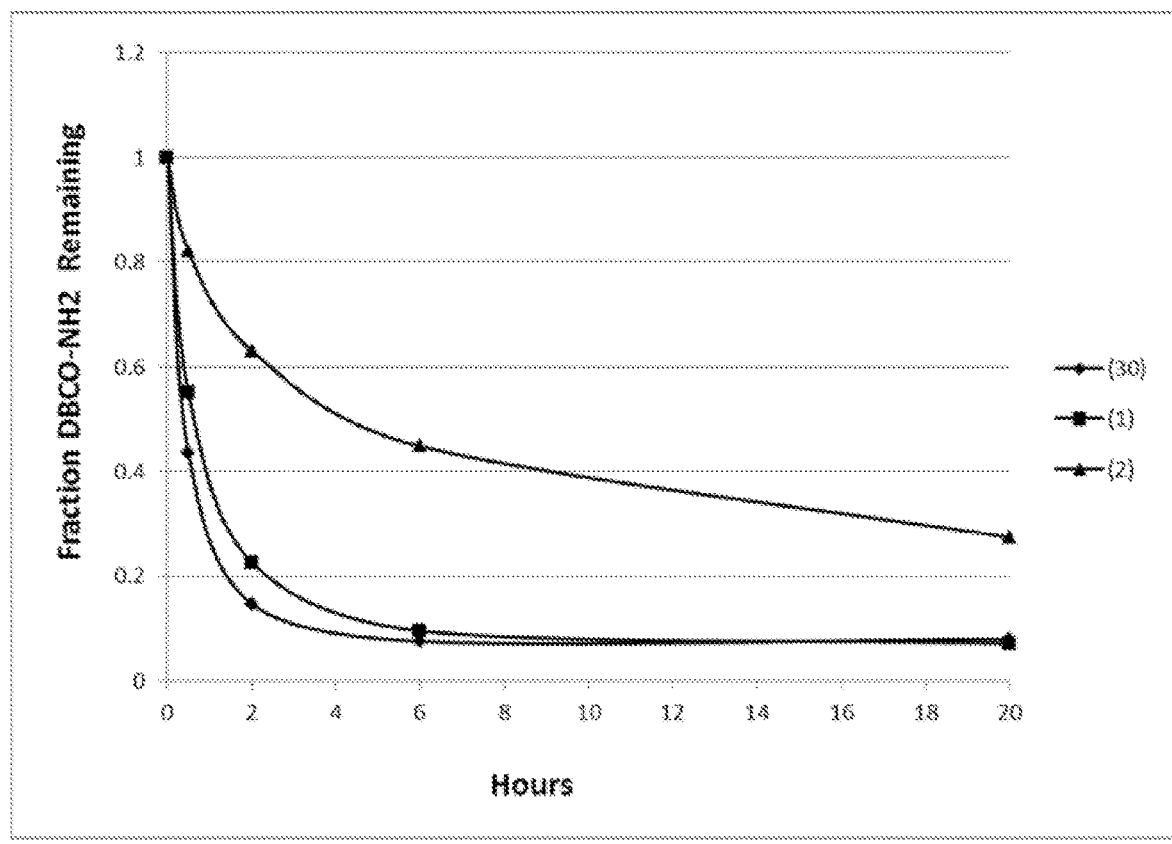
FIG. 4 provides a plot of the fraction of $DBCO-NH_2$ (61) remaining vs. time (hours) during a reaction with amino acid analogs (30), (1), and (2).

The results of the experiment are shown in FIG. 4. Compounds (1) and (30) reacted readily with compound (61) in 1:1 equivalence to produce almost quantitative yield in six hours. The reaction rate between compound (1) and compound (61) was comparable to the reaction rate between compound (30) and compound (61). The reaction rate between compound (2) and compound (61) was two- to four-fold slower than the reaction rate between the other two amino acid analogs and compound (61). However, the reaction rate of compound (2) should be faster than that of compound (50) of Example 6, based on compound (30) as a common comparator.

What is claimed is:

1. A compound according to the following formula:

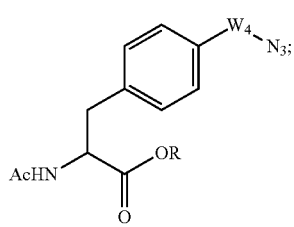

wherein $W_4$ is $C_1$-$C_{10}$ alkylene and R is hydrogen or methyl.

2. The compound of claim 1, wherein R is methyl.
3. The compound of claim 1, wherein R is hydrogen.
4. The compound of claim 2, wherein $W_4$ is $CH_2$.
5. The compound of claim 3, wherein $W_4$ is $CH_2$.
6. The compound of claim 4, wherein the compound is in the L-configuration.
7. The compound of claim 5, wherein the compound is in the L-configuration.
8. A method of preparing a compound according to the following formula:

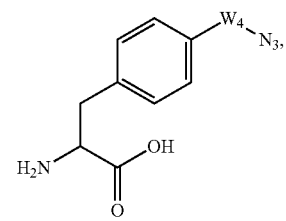

comprising treating a compound of the following formula

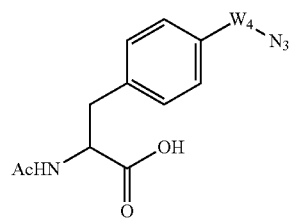

with an acylase
wherein $W_4$ is $C_1$-$C_{10}$ alkylene.

9. The method of claim 8, further comprising preparing the compound of formula:

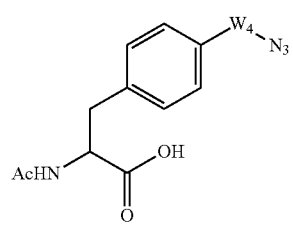

by treating a compound of the following formula:

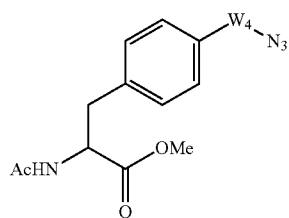

with LiOH.

10. The method of claim 8, wherein $W_4$ is $CH_2$.
11. The method of claim 9, wherein $W_4$ is $CH_2$.
12. The method of claim 10, wherein the compound is in the L-configuration.
13. The method of claim 11, wherein the compound is in the L-configuration.
14. A method of preparing a compound according to the following formula:

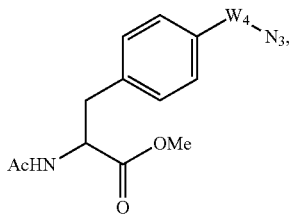

comprising treating a compound of the following formula

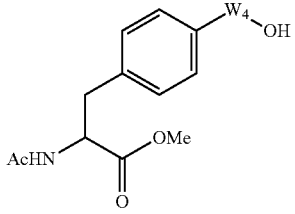

with $NaN_3$.

15. The method of claim 14, wherein $W_4$ is $CH_2$.
16. The method of claim 14, wherein the compound is in the L-configuration.
17. The method of claim 15, wherein the compound is in the L-configuration.

* * * * *